United States Patent [19]
Smith et al.

[11] Patent Number: 5,855,885
[45] Date of Patent: Jan. 5, 1999

[54] ISOLATION AND PRODUCTION OF CATALYTIC ANTIBODIES USING PHAGE TECHNOLOGY

[76] Inventors: Rodger Smith, 4660 Milford Ct., Jefferson, Md. 21755; John McCafferty, 32 Wakelin Ave., Sawston, Cambridgeshire CB2, United Kingdom; David Chiswell, 1 Sandhill House, Middle Cayston, Bucks MK8 2LD, United Kingdom; Michael J. Darsley, 5905 Halsey Rd., Rockville, Md. 20851; Kevin Fitzgerald, 3 Burnstable Close, Saffron, Walden, Essex CB11 3BX, United Kingdom; John H. Kenten, 1921 Windjammer Way, Gaithersburg, Md. 20879; Mark T. Martin, 9 Prairie Rose La., Gaithersburg, Md. 20878; Richard C. Titmas, 12905 Crookston La., Apt. 103, Rockville, Md. 20851; Richard O. Williams, 9408 Althea Ct., Potomac, Md. 20854

[21] Appl. No.: 273,146

[22] Filed: Jul. 14, 1994

Related U.S. Application Data

[63] Continuation of Ser. No. 7,684, Jan. 22, 1993, abandoned.

[51] Int. Cl.$^6$ .......................... A61K 39/395; A61K 38/43; A61K 9/00
[52] U.S. Cl. ...................................... 424/130.1; 435/188.5; 424/94.1; 424/141.1
[58] Field of Search ....................... 435/188.5; 424/130.1, 424/141.1, 94.1

[56] References Cited

PUBLICATIONS

"Phage antibodies: filamentous phage displaying antibody variable domains" by McCafferty et al., 348 *Nature* 552–54 (Dec. 1990).
"Primer–Directed Enzymatic Amplification of DNA with a Thermostable DNA Polymerase" by Saiki et al., 239 *Science* 487–491 (Jan. 1988).
"Protein engineering of antibody binding sites: Recovery of specific activity in an anti–digoxin single–chain Fv analogue produced in *Escherichia coli*" by Huston et al., 85 *Proc. Natl. Acad. Sci. USA* 5879–5883 (Aug. 1988).
"Binding activities of a repertoire of single immunoglubin variable domains secreted from *Escherichia coli*" by Ward et al., 341 *Nature* 544–546 (Oct. 1989).
"Single–Chain Antigen–Binding Proteins" by Bird et al., 242 *Science* 423–426 (Oct. 1988).
"Expression of Functional Antibody Fv and Fab Fragments in *Escherichia coli*" by Pluckthun and Skerra, 178 *Methods of Enzymology* 497–515 (1989).
"By–passing Immunization Human Antibodies from V–gene Libraries Displayed on Phage" by Marks et al., 222 *J. Mol. Biol.* 581–597 (1991).
"Making antibody fragments using phage display libraries" by Clackson et al., 352 *Nature* 624–628 (Aug. 1991).
"Multi–subunit proteins on the surface of filamentous phage: methodologies for displaying antibody (Fab) heavy and light chains" by Hoogenboom et al., 19 *Nucleic Acids Research* 4133–4137 (Jun. 1991).
"Genetic Approach To Facilitate Purification Of Recombinant Proteins With A Novel Metal Chelate Adsorbent" by Hochuli et al., *Bio/Technology* 1321–1325 (Nov. 1988).
"*Escherichia coli* Secretion of an Active Chimeric Antibody Fragment" by Better et al., 240 *Science* 1041–1043 (May 1988).
"By–Passing Immunization: Building High Affinity Human Antibodies By Chain Shuffling" by Marks et al., 10 *Biotechnology* 779–783 (1992).
*Molecular Cloning. A Laboratory Manual* by Maniatis et al., Cold Spring Harbor Laboratory (1982) pp. 68 to 73, 86 to 114, 151 to 170, 440 to 450.
"Ion–Exchange Chromatography" by Rossomanso, 182 *Methods in Enzymology–Guide to Protein Purification* 309–379 (1990).
"Determination of Purity" by Rhodes et al., 182 *Methods of Enzymology — Guide to Protein Purification* 555–565 (1990).
"The Croonian Lecture, 1989 — Antibodies: a paradigm for the biology of molecular recognition" by Milstien, 239 *Proc. R. Soc. Lond.* 1–16 (1990).
Hochuli, et al. (1988) Bio/Technology 1321–1325.
Huse, W. D., et al. (1989) Science 246, 1275–1281.
Kang, A. S., et al (1991) Proc. Natl. Acad. Sci., USA 88, 4363–4366.

*Primary Examiner*—Charles L. Patterson, Jr.
*Attorney, Agent, or Firm*—Whitman Breed Abbott & Morgan LLP

[57] ABSTRACT

Disclosed and claimed are methods for producing catalytic antibodies, including human catalytic antibodies, from bacteriophage. The methods require the cloning, selection, screening, and isolation of catalytic antibodies. Also disclosed and claimed are the products themselves, the catalytic antibodies, made from the phage technology. In addition, catalytic antibodies produced from the phage technology and useful in prodrug activation are disclosed and claimed. And finally, the invention also understands the production of catalytic antibodies to phosphonates.

26 Claims, 71 Drawing Sheets

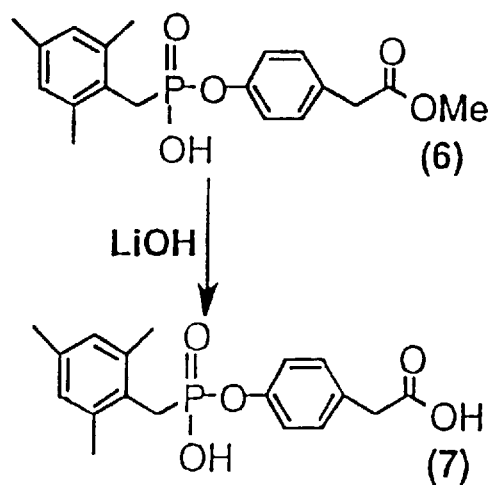
RT3 Phosphonate TSA
*FIG. IA*

L   N   G   A   A amber   (SEE SEQ ID NO:37)
aat ggg gcc gca tag-gene3 (SEE SEQ ID NO:36)

*FIG. 5B*

```
      gIII/pelB LEADER
   V   K   K   L   L   F   A   I   P   L   V   V   P   F   Y   A   A   Q   P   A
  GTG AAA AAA TTA TTA TTC GCA ATT CCT TTA GTT GTT CCT TTC TAT GCG GCC CAG CCG GCC
                                    SfiI  NcoI              PstI        XhoI      NotI
                                                                                      ┌─(SEE SEQ ID NO:41)
   H   H   H   H   H   H   G   A   A   E   Q   K   L   I   S   E   E   D   L   N   G   A   A   Amber
  cat cat cat cac cat cac ggg gcc gca gaa caa aaa ctc atc tca gaa gag gat ctg aat ggg gcc gca tag-gene3
   polyhistidine                          myc tag                                            └─(SEE SEQ ID NO:40)
```

*FIG. 7A*

```
        -1      POLYLINKER
    M  A  I  Q  V  Q  L  Q  E  L  E  I  K  R  A  A  A  A  (SEE SEQ. ID NO:43)
    ATG GCC CAG GTC CAA CTG CAG GAG CTC GAG ATC AAA CGG GCG GCC GCC GCA (SEE SEQ ID NO:42)
```

*FIG. 7C*

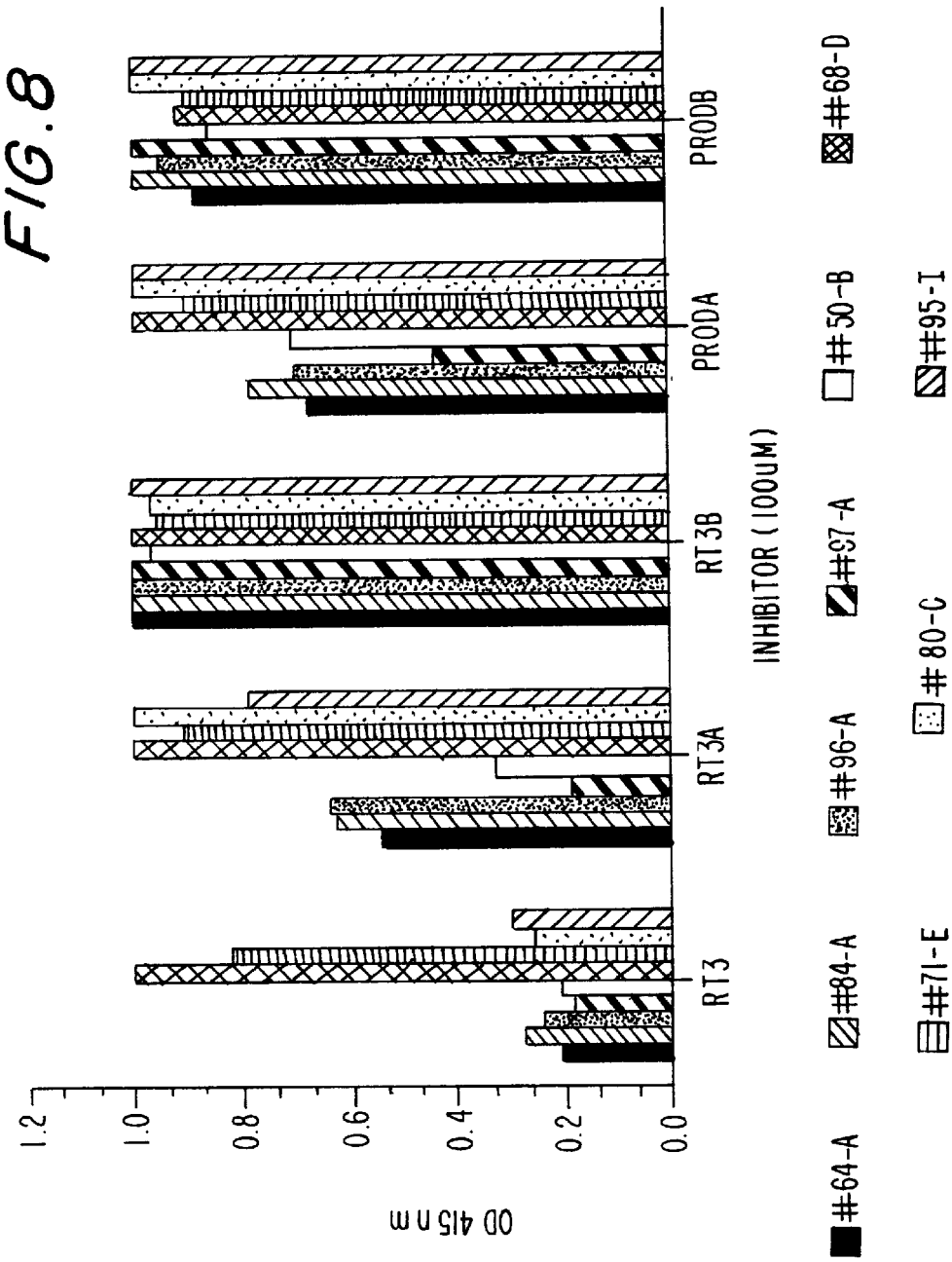

VKBACK  MJKEONX
PCR PATTERN A

```
            I                                    FR1
            S    S   L   S   A   S   L   G   G   E   R   V   S   L   T   C
                         *              *              *              *              *
                    10              20              30              40
D>
al    6,8        TCC TCC TTA TCT GCC TCT CTG GGA GAA AGA GTC AGT CTC ACT TGT
GAT   F                  2 or 4
all 9 18 AND 27---  --- --- --- --- --- --- --- --- --- --- --- --- --- ---
---   9=D, 27=A          9=2or4, 27=1
all13 AND 25---    --- --- --- --- --- --- --- --- --- --- --- --- --- ---
---   3=C, 25=E    3=1, 25=2 or 4
alv   64         --- --- --- --- --- --- --- --- --- --- --- --- --- --- ---
---   E                  1
av    24         --- --- --- --- --- --- --- --- --- --- --- --- --- --- ---
---   C                  2
avi   4          --- --- --- --- --C --- --- --- --- --- --- --- --- --- --C
---   A                  2 or 4
avii  97         --- --- --- --- --- --- --- --- --- --- --- --- --- --- ---
---   E                  1
aviii14,30,      --- --- --- --- --- --- --- --- --- --- --- --- --- --- ---
---   E                  4
36,84,96
```

PCR PATTERN C

| FIG.9A | FIG.9B |
|--------|--------|
| FIG.9C | FIG.9D |
| FIG.9E | FIG.9F |

```
         50              60              70              80              90
          *     CDR1      *              *               *    II    FR2   *
     1    R  A  S  Q  S  I  G  S  S  L   N  W  L  Q  Q  E  P
          CGG GCA AGT CAG AGT ATT GGT AGT AGC TTA AAC TGG CTT CAG CAG GAA CCA
          --- --- --- --- --- --- --- --- --- --- --- --- --- --- --- --- ---
          --- --t --- --- --- --- --- --t --- --- --- --- --- --- --- --- ---
          --- --- --- --- --- --- --- --- --- --- --- --- --- --- --- --- ---
          --- --- --- --- --- --- --- --- --- --- --- --- --- --- --- --- ---
          --- --- --- --- --- --- --- --- --- --- --- --- --- --- --- --- ---
          --- --- --- --- --- --- --- --t --- --- --- --- --- --- --- --- ---
          --- --- --- --- --- --- --- --- --- --- --- --- --- --- --- --- ---
                              E  S  G  Y  S                              K
          --- --a --- a-- g-- ta- -g- --- --- --- --- --- --- --- --a --- ---
```

FIG. 9D

```
       150            160            170            180            190
        *              *              *              *              *
                                     FR3
   G  V  P  K  R  F  S  G  S  R  S  G  S  D  Y  S  L
  GGT GTC CCC AAA AGG TTC AGT GGC AGT AGG TCT GGG TCA GAT TAT TCT CTC
   --- --- --- --- --- --- --- --- --- --- --- --- --- --- --- --- ---
   --- --- --- --- --- --- --- --- --- --- --- --- --- --- --- --- ---
   --- --- --- --- --- --- --- --- --- --- --- --- --- --- --- --- ---
   --- --- --- --- --- --- --- --- --- --- --- --- --- --- --- --- ---
   --- --- --- --- --- --- --- --- --- --- --- --- --- --- --- --- ---
   --- --- --- --- --- --- --- --- --- --- --- --- --- --- --F --- ---
   --- --- --- --- --- --- --- --- --- --- --- --- --- --- --- --- ---
   --- --- --- --- --- --- --- --- --- --- --- --- --- --- --- --- ---
   --a --- --- --- --- --- --- --- --- --- --- --- --- --- --t --- ---
```

FIG. 9E

PCR PATTERN C

|  | 200 | | 210 | | | | 220 | | | | 230 | | | 240 |
|---|---|---|---|---|---|---|---|---|---|---|---|---|---|---|
|  | I | S | S | L | E | S | E | D | F | V | D | Y | Y | C |
|  | ATC | AGC | AGC | CTT | GAG | TCT | GAA | GAT | TTT | GTA | GAC | TAT | TAC | TGT |
| 6, 8 | --- | --- | --- | --- | --- | --- | --- | --- | --- | --- | --- | --- | --- | --- |
| 9 AND 27 | --- | --- | --- | --- | --- | A-- | --- | --- | --- | --- | --- | --- | --- | --- |
| 3 AND 25 | --- | --- | --- | --- | --- | -g- | --- | --- | --- | --- | -t- | --- | --- | --- |
| 64 | --- | --- | --- | --- | --- | --- | --- | --- | --- | --- | V / -t- | --- | --- | --- |
| 24 | --- | --- | --- | --- | --- | --- | --- | --- | --- | --- | G / -g- | --- | --- | --- |
| 4 | --- | --- | --- | --- | --- | --- | --- | --- | --- | A / -c- | --- | --- | --- | --- |
| 97 | --- | --- | --- | --- | --- | --- | --- | --- | --- | A / -c- | --- | --- | --- | --- |
| 14, 30, 36, 84, 96 | --- | --- | --- | --- | --- | --- | --- | --- | --- | --- | --- | --- | --- | --- |
| 80 | --- | --- | --- | --- | --- | --- | --- | --- | --- | --- | --- | --- | --- | --- |

FIG. 9F

```
            250             260             270
             *               *               *
       |  CDR3                          |   | I | FR4 |
       | Q   Y   A   S   S   P   Y   T   F | G   G> (SEE SEQ ID NO:45)
       L                                                  (SEE SEQ ID NO:44)
       CTA CAA TAT GCT AGT TCT CCT TAC ACG TTC GGA GGG
       --- --- -t- --- --- --g --- --- --- --- --- ---
           F
       --- --- -t- --- --- --g --- --- --- --- --- ---
           F
       --- --- --- --- --- --g --- --- --- --- --- ---
                                   L                   A
       --- --- --- --- --- --- ct- --- --- --t --- -ct
       --- --- --- --- --- --g --- --- --- --- --- ---
                               Y   F
       --- --- --- --- -a- --a --t- --- --- --- --- ---
                                                       S
       --- --- --- --- --- --- --- --- --- --- --c tcg

--- --- --- --- --- --- --- --- --- --- --- ---
```

PCR PATTERN B

VKBACK — MJKFONX

```
              1                    10                    20                    30                  40
              S     S     S     M     Y     A     S     L     G     E     I     V     T     I     T
                                 FR1
              I                                                                                 I
         TCT TCC ATG TAT GCA TCT CTA GGA GAG ATA GTC ACT ATC ACT
G>                                                              A
69,50                                               R
GGG (a to G at pos 2)                        -g-

MUSIGKVF  --- --- --- --- --- --- --- --- --- --- --- --- ---

100                   110                   120                   130                 140
              *                     *                     *                     *                   *
              K     S     P     K     T     L     I     Y     R     A     N     R     L     V
                                                              I I                        CDR2
         AAA TCT CCT AAG ACC CTG ATC TAT CGT GCA AAC AGA TTG GTA
T>
69,50
ACC
MUSIGKVF  --- --- --- --- --- --- --- --- --- --- --- --- ---

200                   210                   220                   230                 240
              *                     *                     *                     *                   *
              I     S     S     L     E     Y     E     D     M     G     I     Y     Y     C
                                                                                              I
         ATC AGC AGC CTG GAG TAT GAA GAT ATG GGA ATT TAT TAT TGT
69,50
MUSIGKVF  --- --- --- --- --- --- --- --- --- --- --- --- ---
```

FIG.10A

| FIG.10A | FIG.10B |
|---------|---------|
| FIG.10C | FIG.10D |
| FIG.10E | FIG.10F |

```
           50              60              70              80              90
            *               ▲               *               ▲               ▲
       C    K    A    S    Q    D    I    N    S    Y    L    S    W    F    Q    Q    K    P    E    L
      I          CDR1                               I I         FR2                                        I
      TGC  AAG  GCG  AGT  CAG  GAC  ATT  AAT  AGC  TAT  TTA  AGC  TGG  TTC  CAG  CAG  AAA  CCA
      ---  ---  ---  ---  ---  ---  ---  ---  ---  ---  ---  ---  ---  ---  ---  ---  ---  ---

150             160             170             180             190
            *               *               *               *               *
                                                                                            I I
       D    G    V    P    S    R    F    S    G    S    G    S    G    Q    D    Y    S    L
                                                    I                  FR3
      GAT  GGG  GTC  CCA  TCA  CGG  TTC  AGT  GGC  AGT  GGA  TCT  GGG  CAA  GAT  TAT  TCT  CTC
      ---  ---  ---  ---  a--  ---  ---  ---  ---  ---  ---  ---  ---  ---  ---  ---  ---  ---

250             260             270
            *               *               *          I  I     FR4
       L    Q    Y    D    E    F    P    Y    T    F    G    G>            (SEE SEQ ID NO:47)
      I         CDR3                                                        (SEE SEQ ID NO:46)
      CTA  CAG  TAT  GAT  GAG  TTT  CCG  TAC  ACG  TTC  GGA  GGG
      ---  ---  ---  ---  ---  ---  ---  ---  ---  ---  ---  --t
```

FIG. 10D

```
                 50              60              70              80              90
                  *               *               *               *               *
           I                             CDR1                                  11     FR2
         C  R  A  S  E  N  V  D  S  Y  G  N  S  F  M  H  W  Y
         TGC AGA GCC AGT GAA AAT GTT GAT AGT TAT GGC AAT AGT TTT ATG CAC TGG
                                      S
         --- --- --- --- --- --- --- --- -g- --- --- --- --- --- --- --- --- ---

150             160             170             180             190
                  *               *               *               *               *
              11              FR3                                            11   FR4
         S  N  L  Q  S  G  V  P  A  R  F  S  G  S  G  S  R  T
         TCC AAC CTA CAA TCT GGG GTC CCT GCC AGG TTC AGT GGC AGC GGG TCT AGG
                          E
         --- --- g-- --- --- --- --- --- --- --- --- --- --- --- --- --- --t ---

250             260             270
                  *               *               *
              11    CDR3
         T  Y  Y  C  L  Q  N  T  E  D  P >  (SEE SEQ ID NO:49)
                     Q     N     N
         ACC TAT TAC TGT CTG CAA AAT ACT GAG GAT CCG         (SEE SEQ ID NO:48)
                          -a- --- -a- --- --- --- --t
```

PCR PATTERN I

```
        VKBACK        MJKFONX
                         FR1
         I       L   S   L   P   V   S   L   G   D   Q   A   S   I   S
                     10              20              30              40
                     *               *               *               *
     Y>                              I   I                           I  I
     95          CTC TCC CTG CCT GTC AGT CTT GGA GAT CAA GCC TCC ATC TCT
     TAC
     MUSIGKVD    --- --- --- --- --- --- --- --- --- --- --- --- --- ---
     ---

L   Q   K   P   G   Q   S   P   K   L   L   I   Y   K
                     100             110             120             130             140
                     *               *               *               *               *
                                                                     I  I                 CDR2
     T>  (SEE SEQ ID NO:51)
     95          CTG CAG AAG CCA GGC CAG TCT CCA AAG CTC CTG ATC TAC AAA
     ACA (SEE SEQ ID NO:50)
     MUSIGKVD    --- --- --- --- --- --- --- --- --- --- --- --- --- ---
     ---

D   F   T   L   K   I   S   R   V   E   A   E   D   L
                     200             210             220             230             240
                     *               *               *               *               *
     95          GAT TTC ACA CTC AAG ATC AGC AGA GTG GAG GCT GAG GAT CTG
     MUSIGKVD    --- --- --- --- --- --- --- --- --- --- --- --- --- ---
                     10              20              30              40
```

```
                    50                  60                  70                  80                  90
                     *                   *                   *                   *                   *
                                         CDR1                                          II____FR2
         C   R   S   S   Q   S   L   V   H   S   P   G   N   T   Y   L   H   W   A
         TGC AGA TCT AGT CAG AGC CTT GTA CAC AGT CCT GGA AAC ACC TAT TTA CAT TGG
                                                     N
         --- --- --- --- --- --- --- --- --- --- --- aa- --- --- --- --- --- ---

150                 160                 170                 180                 190
                     *                   *                   *                   *                   *
                   II_____FR3
         V   S   N   R   F   S   G   V   P   D   R   F   S   G   S   G   S   G
         GTT TCC AAC CGA TTT TCT GGG GTC CCA GAC AGG TTC AGT GGC AGT GGA TCA GGG
         --- --- --- --- --- --- --- --- --- --- --- --- --- --- --- --- --- ---

250                 260                 270
                     *                   *                   *
                    I I_____CDR3_____I I____FR4
         G   V   Y   F   C   S   Q   S   T   H   V   P>
         GGA GTT TAT TTC TGC TCT CAA AGT ACA CAT GTT CCG
         --- --- --- --- --- --- --- --- --- --- --t ---
                    50                  60                  70                  80                  90
```

FIG. 11

| FIG.11A | FIG.11B |
|---------|---------|
| FIG.11C | FIG.11D |

FIG. 11A

```
                              10              20           FR1    30                40
                               *               *                   *                  *
            I                                                                          I
            S  S  L  S  A  S  L  G  E  R  V  S  L  T  C
D>
6,8   (A)   TCC TCC TTA TCT GCC TCT CTG GGA GAA AGA GTC AGT CTC ACT TGT
GAT         --- --- --- --- --- --- --- --- --- --- --- --- --- --- ---

80    (C)
---                M  Y                       I     T     I
D
50,69 (B)   --t --- atg -a- --c --- --a --- --g -t- --- -c- a-- --- --c
-gg 95(1)       L   -   -   P   V   -   -   A   -   -   D   Q   A   -   I   S   -
G
10,43,68,83 (D) A   -   -   A   V   -   -   Q   -   -   A   T   I   S   S
s
```

FIG. 11B

```
          50             60               70                80             90
           *              *                *                 *              *
      |       I      |      CDR1     |                  II          |  FR2         |
        R  A  S  Q   D  I  G  S  S   L  N  W  L  Q   Q  E  P
       CGG GCA AGT CAG GAC ATT GGT AGT AGC TTA AAC TGG CTT CAG CAG GAA CCA
                        E           S  G  Y                                K
       --- --a --- --- --- a-- g-- a-- g-- ta- --- --- --- --- --- --- a--
                                    N  S  Y                    S           K
       --- --- --- --- --- --- --- --- --- tat --- --- --- --- --- --- a--
           K                                                   F
       aa- --g --- --- --- aa- --c tat --- -g- --- --- --- --- t-c --- a--
           S           V    II  SPGNTYL  H        Y  L        K
           S           V           II  SPGNTYL  H        Y     Y        K
               E  N  V  D       Y  GNSFM  II                            K
```

```
              100         110         120         130         140
                *           *           *           *           *
                                      I  I                   CDR2
                G   T   I   K   R   L   I   Y   A   T   S   S   L   D   S
T>
6,8  (A)       GGA ACT ATT AAA CGC CTG ATC TAC GCC ACA TCC AGT TTA GAT TCT
ACC
                                                A   T
80   (C)       --- --- --c --- --- --- --- --g --- --- --- --- --- --- ---
                                                              R   A   N   R   V   D
50,69 (B)      aa- t-- cc- --g ac- --- --- --t cgt --- --- --g aa- --a --g -ta ga-
                K   S   P       T
95(I)           Q   S       P       L       -       -       K   V   -   N   R   F   -
K
10,43,68,83 (D) G   P   P   -   L   -   -   -   -   L   A   -   N   -   Q
-   -

200         210         220         230         240
                *           *           *           *           *
                                                                      I   I   L
                I   S   S   L   E   S   E   D   F   V   D   Y   Y   C   L
6,8  (A)       ATC AGC AGC CTT GAG TCT GAA GAT TTT GTA GAC TAT TAC TGT CTA
                                                                A
80   (C)       --- --- --- --- --- --- --- --- --- --c --- --- --- --t ---
                                Y           M   G   I                     F   -   S
50,69 (B)      --- --- --- --g --- -a- --- --- a-g -g- at.l --- --- --- ---
                -   -   R   V   -   A   -   L   G   V   -   F   -
95(I)
10,43,68,83 (D) -   D   P   V   -   A   D   -   A   -   A   T   -   -   -
-   -
```

| FIG.12A | FIG.12B | FIG.12C |
|---------|---------|---------|
| FIG.12D | FIG.12E | FIG.12F |
| FIG.12G | FIG.12H | FIG.12I |
| FIG.12J | | |

FIG. 12

```
                                        10                  20
                                         *                   *
                                    G C A               G   T
              VH1BACK         CAG GTC AAG CTG CAG CAG TCA GG
              _____
                              Q   V   Q   L   Q   Q   S   G   P
         N>
         Ai   14,30,          CAG GTC CAG CTG CAG CAG TCA GGA CCT
         AAC
         36,84,96

Aii  3               _____
         ---

K
         Aiii 4               --- --g a-a --- --- --- --- --- ---
         ---

T
         Aiv  24              --- --- --a --- --- --- --t --- ---
         -c-
                                              K
         Av   9,18            --- --- a-- --- --- --- --- --- ---
         ---
                                              K
         T
         Avi  6,8             --- --g a-- --- --- --- --- --- ---
         -c-
                                              K
         Avii 64              --- --g a-- --- --- --- --t --- ---
         ---

T
         Aviii 97             _____
         -c-

Aix. 27              --- --- --- --- --- --- --t --- ---
         ---
                                              K
         Ax   25              --- --- a-- --- --- --- --t --- ---
         ---
```

FIG.12A
```
                              E
              MUSIGHVK2       g-- --- --- --t --- --- --- --- ---
                              ---
```

```
                    30              40              50              60
                     *               *               *               *

_____FR1_____
                         E    L    V    K    P    G    A    S    V    K    V

GAG  CTG  GTG  AAG  CCT  GGG  GCT  TCA  GTG  AAG  GTA

____11___CDR1___
                                 S   C   K   A   S   G   Y   A   F   T   N   Y

TCC TGC AAG GCT TCT GGT TAT GCA TTC ACT AAC TAC

T       D
                                --- --- --- --- --- --c a-- --- --- g-- ---
``` germline

```
                    100            110            120
                     *              *              *
                   __I I_____FR2_
                     I  Y  W   V   K   Q   S   H    G
G>
14,30,             ATA TAC TGG GTG AAG CAG AGC CAT GGA
GGC
36,84,96

M
3                  --t --- --- --- --- --- --- --- ---
---

M
4                  --g --- --- --- --- --- --- --- ---
---

M
24                 --g --- --- --- --- --- --- --- ---
---

9,18               --c --- --- --- --- --- --- --- ---
---

M
6,8                --g --- --- --- --- --- --- --- ---
---

64                 --- --- --- --- --a --- --- --- ---
---

97                 --g --- --- --- --- --- --- --- ---
---

M
27                 --g --- --- --- --- --- --- --- ---
---

25                 --- --- --- --- --- --- --- --- ---
---

M   H
S
MUSIGHVK2          --g c-- --- --- --- --- --- --- ---
a--
germline
```

AAG AGT CTT GAG TGG ATT GGA TAT ATC GAT CCT

--- --c --- --- --- --- --- --- --t --- ---

--- --c --- --- --- --- --- --- --t --- ---

--- --c --- --- --- --- --- --- --t --- ---

--- --c --- --- --- --- --- --- --t --- ---

--- --c --- --- --- --- --- --- --t --- ---

--- --c --- --- --- --- --- --- --t --- ---

P
   --- --c --- --- --- --- --- --- --t --- ---

I
   --- -tc --- --- --- --- --- nnn nnt --- ---

P
   --- --c -c- --- --- --- --n nnn nnn nn- ---
```

```
               170            180            190
                ▲              ▲              ▲
         CDR2
     _____
      Y    S    G    G    S    S    Y    N    Q    K    F    K

TAC  AGT  GGT  GGT  TCT  AGC  TAC  AAC  CAG  AAG  TTC  AAG

I
                        K   A   T   L   T   V   D   K   S   S
        G>
          14,30        AAG GCC ACA TTG ACT GTT GAC AAG TCC TCC
        GGC
          3            --- --- --- --- --- --- --- --- --- ---
        ---

4            --- --- --- --- --- --- --- --- --- ---
        ---

24           --- --- --- --- --- --- --- --- --- ---
        --t
          9,18         --- --- --- --- --- --- --- --- --- ---
        ---

6,8          --- --- --- --- --- --- --- --- --- ---
        ---

64           --- --- --- --- --- --- --- --- --- ---
        ---

97           --- --- --- --- --- --- --- --- --- ---
        ---

I
          27           --- --- -t- --- --- --- --- --- --- ---
        --g

25           --- --- --- --- --- --- --- --- --- ---
        ---

H
        MUSIGHVK2      --- --- --- --- --- --a --- --t --- ---
        ca- 300          310           320
                          *            *             *

FIG.12G                       ___CDR3_____I  l____FR4____
                        N   P   R   F   A   F   W   G   Q   G
          14,30,        AAT CCC CGT TTT GCT TTC TGG GGC CAA GG_
```

```
        230             240             250             260
         *               *               *               *

___FR3_____
  S    T    A    Y    M    H    L    N    S    L    T

AGC  ACA  GCC  TAC  ATG  CAT  CTC  AAC  AGC  CTG  ACA

---  ---  ---  ---  ---  ---  ---  ---  ---  ---  ---

S
 ---  ---  ---  ---  ---  ---  ---  -g-  ---  ---  ---

I    L
 ---  ---  ---  ---  --a  -t-  ---  ---  ---  ---  ---

---  ---  ---  ---  ---  ---  ---  ---  ---  ---  ---

I    L
 ---  ---  ---  ---  --a  -t-  ---  ---  ---  ---  ---

I
 ---  ---  ---  ---  ---  ---  ---  ---  ---  ---  -t-

L
 ---  ---  ---  ---  ---  -t-  ---  ---  ---  ---  ---

N                                       T
 -a-  ---  ---  ---  ---  ---  ---  -c-  ---  ---  ---

S
 ---  ---  ---  ---  ---  ---  ---  -g-  ---  ---  ---

E         S
 ---  ---  ---  ---  ---  g-g  ---  -g-  ---  ---  ---
```

┌─(SEE SEQ ID NO:55)

─────────────────────I─┘  FIG. 12H

T    T    V    T    V    S    S (SEE SEQ ID NO:54)

```
              270              280              290
               *                *                *

_____I1_____
          S   E   D   S   A   V   Y   Y   C   A   G

TCT GAG GAC TCT GCA GTC TAT TAC TGT GCG GGG
                             36,84,96
         --- --- --- --- --- --- --- --- --- --- ---

G
         --- --- --t --- --- --- --c --- --- -g- ---

V
         --- --- --- --- --- --- --- --- --- --- -t-

--- --- --- --- --- --- --- --- --- --- ---

V
         --- --- --- --- --- --- --- --- --- --- -t-

--- --n nnn nn- --- --- --- --- --- --- ---

V
         --- --- --- --- --g --- --- --- --- --- -t-

I
         --- --- --- --- --c --- --- --t --- --a att

```
36,84,96  ---  ---  ---  ---  ---  ---  ---  ---  ---
3
4         ---  ---  ---  ---  G    ---  ---  ---
24        ---  ---  ---  S    -g-  Y    ---  ---
9,18      ---  ---  ---  -c-  ---  -a-  ---  ---
          ---  ---  ---  ---  G    ---  ---  ---
6,8       ---  ---  ---  S    -g-  Y    ---  ---
          ---  ---  ---  -c-  ---  -a-  ---  ---
64        ---  ---  ---  ---  G    ---  ---  ---
97        ---  ---  ---  S    -g-  Y    ---  ---
          ---  Y    D    -c-  R    -a-  ---  ---
27        ---  ta-  gac  aga  G    ---  ---  ---
25        ---  ---  ---  ---  -g-  ---  ---  ---

MUSIGHVK2  ag-  S

VHFOR-2 (REV)   GG GGC CAA GGG ACC ACG GTC ACC GTC TCC TCA
```

—(SEE SEQ ID NO:15 AT PAGE 34, LINE 16 FOR THE REVERSE OF THIS SEQUENCE)

| FIG.13A | FIG.13B | FIG.13C |
|---------|---------|---------|
| FIG.13D | FIG.13E | FIG.13F |

FIG. 13

PCR PATTERN B

```
                              10                  20
                              *                   *
       I___CDR1___ _____
                    X   X   X   X   Q   Q   S   G   P
       V>
       49,50,69,90 _____ CAG CAG TCT GGT CCT
       GTT
       MUSIGHVJ2   _____ --- --a --- --a ---
       ta- 100                 110                 120
                              *                   *                   *
                              _____1 1_____FR2
       I_____CDR2_____
                    M   H   W   V   K   Q   K   P   G
       G>
       49,50,69,90 ATG CAC TGG GTG AAG CAG AAG CCT GGG
       GGC
       MUSIGHVJ2   --a --- --- --- --- --- -g- --- --a
       ---

200                 210                 220
                              *                   *                   *
                    I_____
       I__
                    K   A   T   L   T   S   D   K   S
       F>
       49,50,69,90 AAG GCC ACA CTG ACT TCA GAC AAA TCC
       TTT
       MUSIGHVJ2   --- --- --- --- --- g-- --- -c- ---
       ---
```

FIG. 13A

```
              _CDR3_I I_____FR4_____
               A   H   W   G   Q   G   T   T   V
       49,50,69,90 GCT CAC TGG GGC CAA GGG ACC ACG GTC
```

```
         30              40              50              60
          *               *               *               *
_____FR1_____

E    L    V    K    P    G    A    S    V    K    M

GAG  CTG  GTA  AAG  CCT  GGG  GCT  TCA  GTG  AAG  ATG

---  ---  --g  ---  ---  ---  ---  ---  ---  ---  --a 130             140             150             160
          *               *               *
                                      _____I
                              _____I
    Q    G    L    E    W    I    G    D    I    N    P

CAG  GGC  CTT  GAG  TGG  ATT  GGA  GAT  ATT  AAT  CCT

---  ---  ---  ---  ---  ---  ---  t--  ---  t--  ---

230             240             250
          *               *               *
_____FR3_____

S    N    T    A    Y    M    E    L    S    S    L

TCC  AAC  ACA  GCC  TAC  ATG  GAG  CTC  AGC  AGC  CTG

---  -g-  ---  ---  ---  ---  c--  ---  ---  ---  ---
```

┌─(SEE SEQ ID NO:57)
                I
_____
 T    V    S    S ◄─┐
ACC  GTC  TCC  TCA ◄─┐
       └─(SEE SEQ ID NO:56)

TCC TGC AAG GCT TCT GGA TAC ACA TTC ACA AGT TAT

--- --- --- --- --- --c --t --c --- --- --c --c 170             180             190
    *        *               *               *

Y   N   D   G   T   K   Y   N   E   K   F   K

TAC AAT GAT GGT ACT AAG TAC AAT GAG AAG TTC AAA aga g-- -g- a-- --- --t --- --- --- --- --- --g 260             270             280             290
    *               *               *               *
_____ I

T   S   E   D   S   A   V   Y   Y   C   A   G

ACC TCT GAG GAC TCT GCG GTC TAT TAC TGT GCG GGG

PCR PATTERN D

```
                            10              20
                             *               *
                         _____
       I___CDR1___
                        Q   V   Q   L   Q   Q   S   G   A
W>
10,26,43,68,83          CAG GTG CAG CTG CAG CAG TCT GGG
TAC TGG
MUSIGVH6                --- --c --- --- --- --- --- -ca ---
ac- 100             110             120
                            *               *               *
                         _____I I_____FR2
       I_____CDR2_____
                        M   H   W   V   K   Q   R   P   G
D>
10,26,43,68,83          ATG CAC TGG GTA AAA CAG AGG CCT
AAG GAC
MUSIGVH6                --- --- --- --- --- --- --- --- ---
---

200             210             220
                            *               *               *
                                I_____
       I__
                        K   A   T   L   T   A   D   K   S
T>
10,26,43,68,83          AAG GCC ACA TTG ACT GCA GAC AAA
AGA ACG
MUSIGVH6                --- a-- --- --- --- --- --- --- ---
cac 300             310             320
                            *               *               *
                         _____CDR3_____I I__
                        L   Y   Y   Y   A   M   D   Y   W
10,26,43,68             TTA TAT TAC TAT GCT ATG GAC TAC TGG
MUSIGVH6                agt gg- gca
```

FIG. 13D

VHFOR-2 (REV)                                              GG

```
       30              40              50              60
       *               *               *               *
_____FR1_____

E   L   A   K   P   G   A   S   V   K   M   S

GCT GAA CTG GCA AAA CCT GGG GCC TCA GTG AAG ATG

--- --- --- --- -g- --- --- --- --- --- --- ---

130             140             150             160
       *               *               *               *
_____I
_____I
  Q   G   L   E   W   I   G   Y   I   N   P   S

GGA CAG GGT CTG GAA TGG ATT GGA TAC ATT AAT CCT

--- --- --- --- --- --- --- --- --- --- --- ---

230             240             250             260
       *               *               *               *
_____FR3_____

S   S   T   A   Y   M   Q   L   S   S   L   T

TCC TCC AGC ACA GCC TAC ATG CAA CTG AGC AGC CTG

--- --- --- --- --- --- --- --- --- --- --- ---

330
       *
____FR4_____I
  G   Q   G   T   T   (SEE SEQ ID NO:59)
GGC CAA GGG ACC ACC GTC ACC GTC TCC TCA─┐
                         └─(SEE SEQ ID NO:58)

GGC CAA GGG ACC ACG GTC ACC GTC TCC TCA─┐      FIG.13E
└─(SEE SEQ ID NO:15, AT PAGE 34, LINE 16 FOR THE REVERSE OF THIS SEQUENCE)
```

```
                      70 .                80                  90
                        *                  *                   *
_____ I

C    K    A    S    G    Y    T    F    T    S    Y

TCC  TGC  AAG  GCT  TCT  GGC  TAC  ACC  TTT  ACT  AGC

---  ---  ---  ---  ---  ---  ---  ---  ---  ---  ---

170                 180                 190
                       *                   *                   *

T    G    Y    T    E    Y    N    Q    K    F    K

AGC  ACT  GGT  TAT  ACT  GAG  TAC  AAT  CAG  AAG  TTC

-g-  --a  ---  ---  ---  ---  ---  ---  ---  ---  ---

270                 280                 290
                       *                   *                   *
_____ I

S    E    D    S    A    V    Y    Y    C    A    R

ACA  TCT  GAG  GAC  TCT  GCA  GTC  TAT  TAC  TGT  GCA

| FIG.14A | FIG.14B | FIG.14C |
|---------|---------|---------|
| FIG.14D | FIG.14E | FIG.14F |

```
                       10              20              30
                        *               *               *
                  G C A         G     T
VH1BACK       CAG GTC AAG CTG CAG CAG TCA GG

I___CDR1___
          (PATTERN B)  X   X   X   X   Q   Q   S   G   P   E
         V>
         49,50,69,90                       CAG CAG TCT GGT CCT GAG
         GTT
                               K   L
         80 (C)            ___AAG CTG --- --- --- --a --- ---
         ---

95 (I)            ___         --- --- --- --a --- ---
         ---
                  Q   V   Q   L                           A
         W
         10,26,43,68,83 CAG GTG CAG CTG --- --- --- --g g--
         --c tgg
         (D)
         N
         14 (A)                         --- --- --a --a --- ---
         aac 100             110             120             130
                        *               *               *               *
                              I I_____FR2__
         I_____CDR2_____
                   M   H   W   V   K   Q   K   P   G   Q
         G>
         49,50,69,90 ATG CAC TGG GTG AAG CAG AAG CCT GGG CAG
         GGC
         (B)
         80 (C)    --- --- --- --- --- --- --- --- --- ---
         ---
         95 (I)    --- --- --- --- --- --- --- --- --- ---
         ---
                                                       R
         D
         10,26,43,68,83 --- --- --- --a --a --- -g- --- --a
         --g -a-
         (D)       I   H                       S   H   K
         14 (A)    --a t-- --- --- --- --- -gc -a- --a a--
         ---
```

CTG  GTA  AAG  CCT  GGG  GCT  TCA  GTG  AAG  ATG  TCC

---  ---  ---  ---  ---  ---  ---  ---  ---  ---  ---

---  ---  ---  ---  ---  ---  ---  ---  ---  ---  ---

A

--a  ---  -c-  --a  ---  ---  --c  ---  ---  ---  ---

V

---  --g  ---  ---  ---  ---  ---  ---  ---  g-a  ---

140             150             160
                 *               *               *
                _____l
                _____I
                G    L    E    W    I    G    D    I    N    P    Y

GGC  CTT  GAG  TGG  ATT  GGA  GAT  ATT  AAT  CCT  TAC

TGC AAG GCT TCT GGA TAC ACA TTC ACA AGT TAT

N
        --- --- --- --- --- --- --- --- --t -ac ---

AMB
        --- t-- --- --- --- --- --- --- --- --- ---

--- --- --- --- --- --c --- --c --t --t --c

D               A               N

--- --- -a- --- --t --t g-- --- --t -ac --c 170             180             190
                    *               *               *

N   D   G   T   K   Y   N   E   K   F   K

AAT GAT GGT ACT AAG TAC AAT GAG AAG TTC AAA

```
                    200              210              220
                     *                *                *
                  ]_____
]_
                  K    A    T    L    T    S    D    K    S    S
F>
49,50,69,90       AAG  GCC  ACA  CTG  ACT  TCA  GAC  AAA  TCC  TCC
                  TTT
(D)
80 (C)            ---  ---  ---  ---  ---  ---  ---  ---  ---  ---
                  ---
95 (I)            ---  ---  ---  ---  ---  ---  ---  ---  ---  ---
                  ---
                                                     A
                  T    L    Y    Y    Y    A    M
10,26,43,68,83    ---  ---  ---  t--  ---  g--  ---  ---  ---
                  a-a  acg  tta  tat  tac  tat  gct  atg
(D)                                                       V
                  G    N    P    R    F
14 (A)            ---  ---  ---  t--  ---  gtt  ---  --g  ---  ---
                  ggc  aat  ccc  cgt  ttt
                                 *                *                *

_CDR3_| |_____FR4_____
                  A    H    W    G    Q    G    T    T    V    T
49,50,69,90       GCT  CAC  TGG  GGC  CAA  GGG  ACC  ACG  GTC  ACC
                            Y
80 (C)            ---  t--  ---  ---  ---  ---  ---  ---  ---  ACC
95 (I)            ---  ---  ---  ---  ---  ---  ---  ---  GTC  ACC
                  D    Y
10,26,43,68,83    gac  t--  ---  ---  ---  ---  ---  ---  ---  GTC
(D)               A    F
14 (A)            gct  ttc  ---  --C  CAA  GGG  ACC  ACG  GTC  ACC

VHFOR-2(REV)                GG   GGC  CAA  GGG  ACC  ACG  GTC  ACC
```

AAC  ACA  GCC  TAC  ATG  GAG  CTC  AGC  AGC  CTG  ACC

S
        -g-  ---  ---  ---  ---  ---  ---  ---  ---  ---  ---

---  ---  ---  ---  ---  ---  ---  ---  ---  ---  ---

S              Q
        ---  -g-  ---  ---  ---  ---  c-a  --g  ---  ---  ---

S              H         N
        -g-  ---  ---  ---  ---  c-t  ---  -a-  ---  ---  --a

I
         V    S    S   (SEE SEQ ID NO:51 PREVIOUSLY APPEARING AT SHEET 39/71)
        GTC  TCC  TCA  (SEE SEQ ID NO:56 PREVIOUSLY APPEARING AT SHEET 39/71)

GTC  TCC  TCA
        GTC  TCC  TCA

ACC  GTC  TCC  TCA

GTC  TCC  TCA

GTC  TCC  TCA (SEE SEQ ID NO:15 AT PAGE 34, LINE 16 FOR THE REVERSE OF
                       THIS SEQUENCE)
```

TCT  GAG  GAC  TCT  GCG  GTC  TAT  TAC  TGT  GCG  GGG

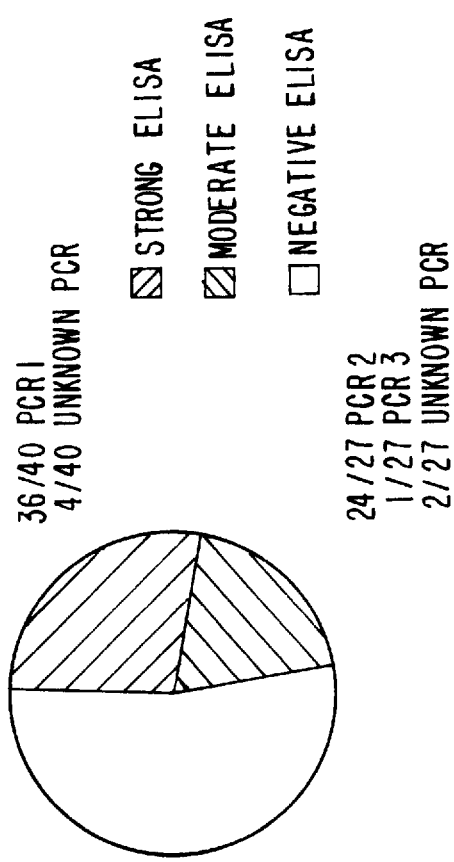

FIG. 20A

HEAVY CHAIN

```
FR 1                                                                    CDR 1                        FR 2
GAA GTC TCC TGC AAG GCT TCT GGA GGC ACC TTC AGC TAT GCT ATC AGC TGG
CTT CAG AGG ACG TTC CGA AGA CCT TGG AAG TCG ATA CGA TAG TCG ACC
Glu Val Ser Cys Lys Ala Ser Gly Gly Thr Phe Ser Tyr Ala Ile Ser Trp

CDR 2
GTG CGA CAG GCC CCT GGA CAA GGG CTT GAG TGG ATG GGA ATC AAC GCT GGC
CAC GCT GTC CGG GGA CCT GTT CCC GAA CTC ACC TAC CCT TAG TTG CGA CCG
Val Arg Gln Ala Pro Gly Gln Gly Leu Glu Trp Met Gly Ile Asn Ala Gly

FR 3
AAT GGT AAC ACA AAA TAT TCA CAG AAG TTC CAG GGC AGA GTC ACC ATT ACC AGG
TTA CCA TTG TGT TTT ATA AGT GTC TTC AAG GTC CCG TCT CAG TGG TAA TGG TCC
Asn Gly Asn Thr Lys Tyr Ser Gln Lys Phe Gln Gly Arg Val Thr Ile Thr Arg

GAC ACA TCC GCG AGC ACA GCC TAC ATG GAG CTG AGC AGC CTG AGA TCT GAA GAC
CTG TGT AGG CGC TCG TGT CGG ATG TAC CTC GAC TCG TCG GAC TCT AGA CTT CTG
Asp Thr Ser Ala Ser Thr Ala Tyr Met Glu Leu Ser Ser Leu Arg Ser Glu Asp

ACA GCT GTG TAT TAC TGT (SEE SEQ ID NO:60)
TGT CGA CAC ATA ATG ACA
Thr Ala Val Tyr Tyr Cys (SEE SEQ ID NO:61)
```

FIG. 20B

LIGHT CHAIN

```
........                                                              CDR 1
     FR 1
CAC CCT CAG CGT CTG GAC CCC GGG CAG AGG GTC ACC ATC TCT TGT TCT GGA AGC
His Pro Gln Arg Leu Asp Pro Gly Gln Arg Val Thr Ile Ser Cys Ser Gly Ser

GTG GGA GTC GCA GAC CTG GGG CCC GTC TCC CAG TGG TAG ACA AGA CCT TCG
Val Gly Val Ala Asp Leu Gly Pro Val Ser Gln Trp * Thr Arg Pro Ser

FR 2
AGC TCC AAC ATC GGA AGA AGT ACT GTA AGC TGG TAC CAG CAG CTC CCA GGC ACG
Ser Ser Asn Ile Gly Arg Ser Thr Val Ser Trp Tyr Gln Gln Leu Pro Gly Thr

TCG AGG TTG TAG TCT CCT TCA TGA CAT TCG ACC ATG GTC GTC GAG GGT CCG TGC
Ser Arg Leu * Ser Pro Ser * His Ser Thr Met Val Val Glu Gly Pro Cys

FR 3
       CDR 2
GCC CCC AAA CTC GTC ATG TAT AGT CAC AAT CAG CGG TCC TCA GGG GTC CCT GAC
Ala Pro Lys Leu Val Met Tyr Ser His Asn Gln Arg Ser Ser Gly Val Pro Asp

CGG GGG TTT GAG CAG TAC ATA TCA GTG TTA GTC GCC AGG AGT CCC CAG GGA CTG
Arg Gly Phe Glu Gln Tyr Ile Ser Val Leu Val Ala Arg Ser Pro Gln Gly Leu

CGA TTC TCT GGC TCC AAG TCT GGC AAC TCA GCC TCC AGG GAC ATC AGT GGG CTC
Arg Phe Ser Gly Ser Lys Ser Gly Asn Ser Ala Ser Arg Asp Ile Ser Gly Leu

GCT AAG AGA CCG AGG TTC AGA CCG TTG AGT CGG AGG TCC CTG TAG TCA CCC GAG
Ala Lys Arg Pro Arg Phe Arg Pro Leu Ser Arg Arg Ser Leu * Ser Pro Glu

CDR 3
Arg Phe Ser Gly Ser Lys Ser Gly Asn Ser Ala Ser Leu Asp Ile Ser Gly Leu

CAG TCT GAG GAT GAG GCT GAT TAT TAC TGT GCA TGG GAT GAC AGC CTG AGT
Gln Ser Glu Asp Glu Ala Asp Tyr Tyr Cys Ala Trp Asp Asp Ser Leu Ser

CTC AGA CTC CTA CTC CGA CTA ATA ATG ACA CGT CGT ACC CTA CTG TCG GAC TCA
Leu Arg Leu Leu Leu Arg Leu Ile Met Thr Arg Arg Thr Leu Leu Ser Asp Ser

GTC AGT GAC ACT GTA CAG ACG TAC AGG GCA GTA CGC AGC ATG GGA CTC AGA GTC
Gln Ser Asp Thr Val Gln Thr Tyr Arg Ala Val Arg Ser Met Gly Leu Arg Val
Gln Ser Glu Asp Glu Ala Asp Tyr Tyr Cys Ala Trp Asp Asp Ser Leu Ser

CTC AGA CTC CTA CTC CGA CTA ATA ATG ACA CGT CGT ACC CTA CTG TCG GAC TCA
Leu Arg Leu Leu Leu Arg Leu Ile Met Thr Arg Arg Thr Leu Leu Ser Asp Ser

FR 4
GAA TTT CTC TTC GGA ACT GGG ACC AAG GTC ACC GTC CTA GGT  (SEE SEQ ID NO:62)
Glu Phe Leu Phe Gly Thr Gly Thr Lys Val Thr Val Leu Gly  (SEE SEQ ID NO:63)
CTT AAA GAG AAG CCT TGA CCC TGG TTC CAG CAG GAT CCA
```

FIG. 20C

HEAVY CHAIN

...FR 1

TCC CTG AGA CTC TCC TGT GCA GCC TCT GGA TTC ACC   CDR 1
AGG GAC TCT GAG AGG ACA CGT CGG AGA CCT AAG TGG AAA TCG ATA CGG TAC
Ser Leu Arg Leu Ser Cys Ala Ala Ser Gly Phe Thr Phe Ser Ser Tyr Ala Met

FR 2

AGC GTC CGC CAG GCT CCA GGG AAG GGG CTG GAG TGG GTC TCA   CDR 2
TCG ACC CAG GTC CGA GGT CCC TTC CCC GAC CTC ACC CAG AGT AGG TAA TCA
Ser Trp Val Arg Gln Ala Pro Gly Lys Gly Leu Glu Trp Val Ser Ser Ile Ser

AGT AGT GAC ACA TAC TAC GCA GAC TCA GTG AAG GGC   FR 3
TCA TCA CTG CGT ATG ATG CGT CTG AGT CAC TTC CCG CGA TTC ACC ATC
Ser Ser Gly Asp Thr Tyr Tyr Ala Asp Ser Val Lys Gly Arg Phe Thr Ile

TCC AGA GAC AAC GCC CAG AAC TCA CTG TAT CTG CAA ATG AAC AGC CTG AGA GTC
AGG TCT CTG TTG CGG GTC TTG AGT GAC ATA GAC GTT TAC TTG TCG GAC TCT CAG
Ser Arg Asp Asn Ala Gln Asn Ser Leu Tyr Leu Gln Met Asn Ser Leu Arg Val

GAG GAC ACG GCT GTT TAT TAC TGT GCG AGA   CDR 3
CTC CTG TGC CGA CAA ATA ATG ACA CGC TCT CAG TCC CAA ATG TCG CGG ACC
Glu Asp Thr Ala Val Tyr Tyr Cys Ala Arg Val Arg Val Tyr Ser Ser Ala Trp

FR 4

GAC TAC TGG GGC CAG GGA ACC CTG GTC ACC GTC TCC (SEE SEQ ID NO:64)
CTG ATG ACC CCG GTC CCT TGG GAC CAG CAG AGG
Asp Tyr Trp Gly Gln Gly Thr Leu Val Thr Val Ser (SEE SEQ ID NO:65)

FIG. 20D

LIGHT CHAIN

..FR 2

| | | | | | CDR 2 | | | | | | FR 3 | | | | | |
|---|---|---|---|---|---|---|---|---|---|---|---|---|---|---|---|---|
| GTA | CTT | GTC | ATC | TAT | GGT | AAA | AAC | AAC | CGG | CCC | TCA | GGG | ATC | CCA | GAC | CGA | TTC |
| CAT | GAA | CAG | TAG | ATA | CCA | TTT | TTG | TTG | GCC | GGG | AGT | CCC | TAG | GGT | CTG | GCT | AAG |
| Val | Leu | Val | Ile | Tyr | Gly | Lys | Asn | Asn | Arg | Pro | Ser | Gly | Ile | Pro | Asp | Arg | Phe |

| TCT | GGC | TCC | AGC | TCA | GGA | AAC | ACA | GCT | TCC | TTG | ACC | ATC | ACT | GGG | GCT | CAG | GCG |
|---|---|---|---|---|---|---|---|---|---|---|---|---|---|---|---|---|---|
| AGA | CCG | AGG | TCG | AGT | CCT | TTG | TGT | CGA | AGG | AAC | TGG | TAG | TGA | CCC | CGA | GTC | CGC |
| Ser | Gly | Ser | Ser | Gly | Asn | Thr | Ala | Ser | Leu | Thr | Ile | Thr | Gly | Ala | Gln | Ala |

| | | | | | | | | | | CDR 3 | | | | | | | |
|---|---|---|---|---|---|---|---|---|---|---|---|---|---|---|---|---|---|
| GAA | GAT | GAG | GCT | GAC | TAT | TAC | TGT | AAC | TCC | CGG | GAC | AGC | AGT | AAC | CAT | AGA |
| CTT | CTA | CTC | CGA | CTG | ATA | ATG | ACA | TTG | AGG | GCC | CTG | TCG | TCA | TTG | GTA | TCT |
| Glu | Asp | Glu | Ala | Asp | Tyr | Tyr | Cys | Asn | Ser | Arg | Asp | Ser | Ser | Gly | Asn | His | Arg |

FR 4

| GTT | GTT | ACG | GCC | GGA | GGG | ACC | AAG | CTG | ACC | GTC | CTA | GGT | (SEE SEQ ID NO:66) |
|---|---|---|---|---|---|---|---|---|---|---|---|---|---|
| CAA | CAA | TGC | CGG | CCT | CCC | TGG | TTC | GAC | TGG | CAG | GAT | CCA | |
| Val | Val | Thr | Ala | Gly | Gly | Thr | Lys | Leu | Thr | Val | Leu | Gly | (SEE SEQ ID NO:67) |

HEAVY CHAIN

..FR 1

| | | | | | | | | | | | | | | | | CDR 1 | |
|---|---|---|---|---|---|---|---|---|---|---|---|---|---|---|---|---|---|
| CTC | GAG | ACC | CTG | TCG | CTC | ACC | TGC | GCT | GTC | TCT | GGT | TAC | TCC | ACA | CGG | TTA | CTA |
| GAG | CTC | TGG | GAC | AGC | GAG | TGG | ACG | CGA | CAG | AGA | CCA | ATG | AGG | TGT | GCC | AAT | GAT |
| Leu | Glu | Thr | Leu | Ser | Leu | Thr | Cys | Ala | Val | Ser | Gly | Tyr | Ser | Thr | Arg | Leu | Leu |

FR 2

| | | | | | | | | | | | CDR 2 | |
|---|---|---|---|---|---|---|---|---|---|---|---|---|
| CTG | GCC | TGG | GTC | CGG | CAC | CTC | CCA | GGG | AAG | GGG | CTG | GAG | TGG | ATT | GGG | AGT | ATA |

FIG. 20E

GAC CGG ACC CAG GCC GTG GAG GGT CCC TTC CCC GAC CTC ACC TAA CCC TCA TAT
Leu Ala Trp Val Arg His Leu Pro Gly Leu Lys Gly Leu Glu Trp Ile Gly Ser Ile

FR 3

CAT CAT AGT GGG CCC ACC TAC TAC AAC CCG TCC CTC AAG AGT CGA GTC ACC ATG
GTA GTA TCA CCC GGG TGG ATG ATG TTG GGC GAG TTC TCA GCT CAG TGG TAC
His His Ser Gly Pro Thr Tyr Tyr Asn Pro Ser Leu Lys Ser Arg Val Thr Met

TCA CCT GAC ACG TCC AGG AAC CAG TTC TCC CTG AAG ATG ACC TCT GTG ACC GCC
AGT GGA CTG TGC AGG TCC TTG GTC AAG AGG GAC TTC TAC TGG AGA CAC TGG CGG
Ser Pro Asp Thr Ser Arg Asn Gln Phe Ser Leu Lys Met Thr Ser Val Thr Ala

CDR 3

GCG GAC ACG GCC ATG TAT TAC TGT GCG AGG GAC CGA TAT GGT TAC TTT GAC TCC
CGC CTG TGC CGG TAC ATA ATG ACA CGC TCC CTG GCT ATA CCA ATG AAA CTG AGG
Ala Asp Thr Ala Met Tyr Tyr Cys Ala Arg Asp Arg Tyr Gly Tyr Phe Asp Ser

FR 4

TGG GGC CAG GGA ACC CTG GCC ACC GTC TC (SEE SEQ ID NO:68)
ACC CCG GTC CCT TGG GAC CGG TGG CAG AG
Trp Gly Gln Gly Thr Leu Ala Thr Val Ser (SEE SEQ ID NO:69)

LIGHT CHAIN

FR 1                                                            CDR 1

CCT GCT TGG TTG CTT GTG GCC TTG GGA CAG ACA GTC AGG ATC ACA TGC CAA GGA
GGA CGA ACC AAC GAA CAC CGG AAC CCT GTC TGT CAG TCC TAG TGT ACG GTT CCT
Pro Ala Trp Leu Leu Val Ala Leu Gly Gln Thr Val Arg Ile Thr Cys Gln Gly

*                                FR 2

GAC AGC CTC AGA AGT TAT TAT GCA AGT TGG TAT CAG CAG AAG CCA GGA CAG GCC
CTG TCG GAG TCT TCA ATA ATA CGT TCA ACC ATA GTC GTC TTC GGT CCT GTC CGG
Asp Ser Leu Arg Ser Tyr Tyr Ala Ser Trp Tyr Gln Gln Lys Pro Gly Gln Ala

FIG. 20F

CDR 2      FR 3

```
CCT GTA CTT GTC ATC TCT  GGT AAA AAC AAC  CGG CCC TCA GGG ATC CCA GAC CGA
GGA CAT GAA CAG TAG AGA  CCA TTT TTG TTG  GCC GGG AGT CCC TAG GGT CTG GCT
Pro Val Leu Val Ile Ser  Gly Lys Asn Asn  Arg Pro Ser Gly Ile Pro Asp Arg

TTC TCT GCC TCC AGC TCA GGA AAC ACA GCT TCC TTG ACC ATC ACT GGG GCT CAG
AAG AGA CGG AGG TCG AGT CCT TTG TGT CGA AGG AAC TGG TAG TGA CCC CGA GTC
Phe Ser Ala Ser Ser Ser Gly Asn Thr Ala Ser Leu Thr Ile Thr Gly Ala Gln
```

CDR 3

```
GCG GAA GAT GAG GCT GAC TAT TAC TGT  CTC TCT CGG GAC AGC GGA AGT AAC CAA
CGC CTT CTA CTC CGA CTG ATA ATG ACA  GAG AGA GCC CTG TCG CCT TCA TTG GTT
Ala Glu Asp Glu Ala Asp Tyr Tyr Cys  Leu Ser Arg Asp Ser Gly Ser Asn Gln
```

FR 4

```
CTG GTA TTC GGC GGA GGG ACC AAG CTG ACC GTC CTA GGT  (SEE SEQ ID NO:70)
GAC CAT AAG CCG CCT CCC TGG TTC GAC TGG CAG GAT CCA
Leu Val Phe Gly Gly Gly Thr Lys Leu Thr Val Leu Gly  (SEE SEQ ID NO:71)
```

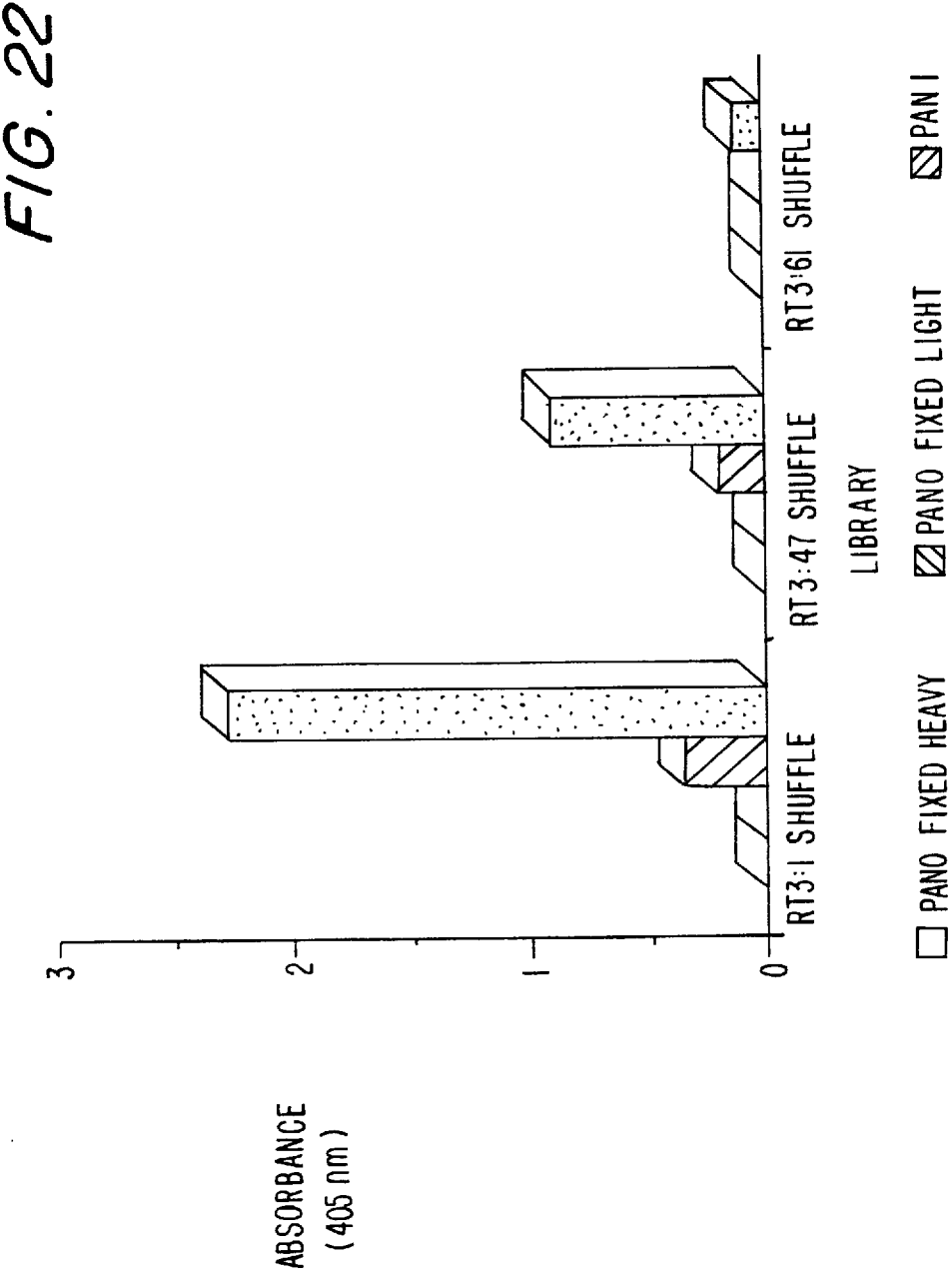

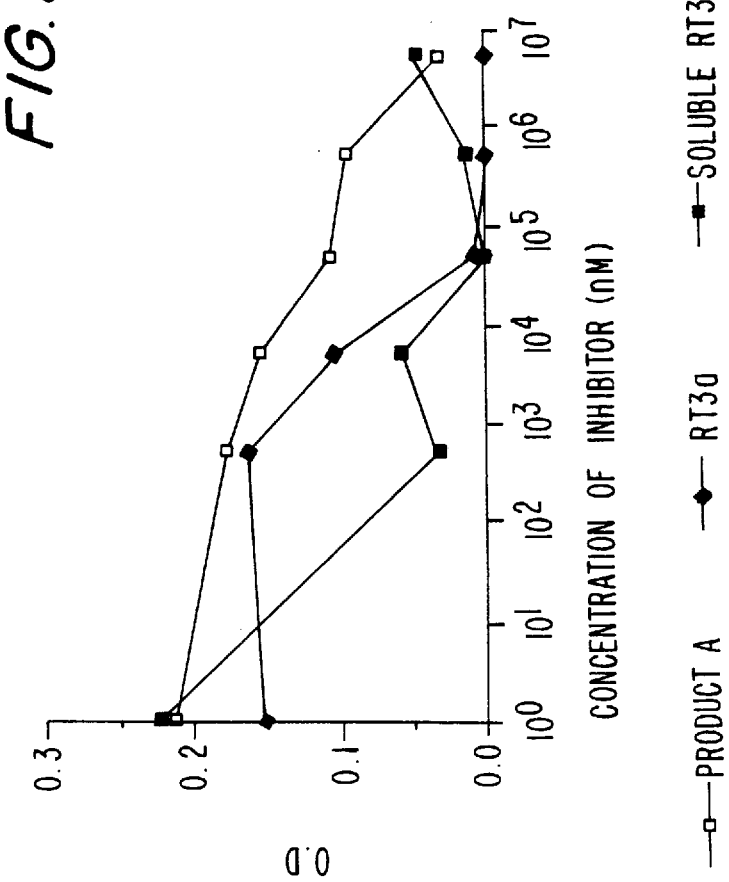

SEQUENCE LISTING ( 1 ) GENERAL INFORMATION:

( i i i ) NUMBER OF SEQUENCES: 71

( 2 ) INFORMATION FOR SEQ ID NO:1:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:1:

GGCCGCACAT CATCATCACC ATCACTA 27

( 2 ) INFORMATION FOR SEQ ID NO:2:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:2:

GGCCTAGTGA TGGTGATGAT GATGTGC 27

( 2 ) INFORMATION FOR SEQ ID NO:3:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:3:

GGCCGCACAT CATCATCACC ATCACGG 27

( 2 ) INFORMATION FOR SEQ ID NO:4:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:4:

GGCCCCGTGA TGGTGATGAT GATGTGC 27

( 2 ) INFORMATION FOR SEQ ID NO:5:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:5:

GATGTTTTGA TGACCCAAAC TCCA 24

( 2 ) INFORMATION FOR SEQ ID NO:6:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:6:

GATATTGTGA TAACCCAGGA TGAA                                                                              2 4

( 2 ) INFORMATION FOR SEQ ID NO:7:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i x ) FEATURE:
            ( A ) NAME/KEY: misc_feature
            ( B ) LOCATION: 12
            ( D ) OTHER INFORMATION: /note= "A or G at position 12"

( x i ) SEQUENCE DESCRIPTION: SEQ ID NO:7:

GACATTGTGC TNACCCAGTC TCCA                                                                              2 4

( 2 ) INFORMATION FOR SEQ ID NO:8:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:8:

GACATCCAGA TGACNCAGTC TCCA                                                                              2 4

( 2 ) INFORMATION FOR SEQ ID NO:9:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:9:

CAAATTGTTC TCACCCAGTC TCCA                                                                              2 4

( 2 ) INFORMATION FOR SEQ ID NO:10:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:10:

GAAAATGTGC TCACCCAGTC TCCA                                                                              2 4

( 2 ) INFORMATION FOR SEQ ID NO:11:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:11:

CCGTTTGATT TCCAGCTTGG TGCC                                                                              2 4

( 2 ) INFORMATION FOR SEQ ID NO:12:

( i ) SEQUENCE CHARACTERISTICS:
            ( A ) LENGTH: 24 base pairs (B) TYPE: nucleic acid
(C) STRANDEDNESS: single
(D) TOPOLOGY: linear (xi) SEQUENCE DESCRIPTION: SEQ ID NO:12:

CCGTTTTATT TCCAGCTTGG TCCC                                                 24

(2) INFORMATION FOR SEQ ID NO:13:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:13:

CCGTTTTATT TCCAACTTTG TCCC                                                 24

(2) INFORMATION FOR SEQ ID NO:14:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:14:

CCGTTTCAGC TCCAGCTTGG TCCC                                                 24

(2) INFORMATION FOR SEQ ID NO:15:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:15:

TGAGGAGACG GTGACCGTGG TCCCTTGGCC CC                                        32

(2) INFORMATION FOR SEQ ID NO:16:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:16:

AGGTSMARCT GCAGSAGTCW GG                                                   22

(2) INFORMATION FOR SEQ ID NO:17:

(i) SEQUENCE CHARACTERISTICS:
(A) LENGTH: 45 base pairs
(B) TYPE: nucleic acid
(C) STRANDEDNESS: single
(D) TOPOLOGY: linear (xi) SEQUENCE DESCRIPTION: SEQ ID NO:17:

TGGAGTTTGG GTCATCAAAA CATCCGATCC GCCACCGCCA GAGCC                          45

(2) INFORMATION FOR SEQ ID NO:18:

(i) SEQUENCE CHARACTERISTICS:
(A) LENGTH: 45 base pairs
(B) TYPE: nucleic acid
(C) STRANDEDNESS: single (D) TOPOLOGY: linear (xi) SEQUENCE DESCRIPTION: SEQ ID NO:18:

TTCATCCTGG GTTATCACAA TATCCGATCC GCCACCGCCA GAGCC    45

(2) INFORMATION FOR SEQ ID NO:19:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 13
        (D) OTHER INFORMATION: /note= "T or C at position 13"

(xi) SEQUENCE DESCRIPTION: SEQ ID NO:19:

TGGAGACTGG GTNAGCACAA TGTCCGATCC GCCACCGCCA GAGCC    45

(2) INFORMATION FOR SEQ ID NO:20:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:20:

TGGAGACTGN GTCATCTGGA TGTCCGATCC GCCACCGCCA GAGCC    45

(2) INFORMATION FOR SEQ ID NO:21:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:21:

TGGAGACTGG GTGAGAACAA TTTGCGATCC GCCACCGCCA GAGCC    45

(2) INFORMATION FOR SEQ ID NO:22:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:22:

TGGAGACTGG GTGAGCACAT TTTCCGATCC GCCACCGCCA GAGCC    45

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:23:

GGGACCACGG TCACCGTCTC CTCA    24

(2) INFORMATION FOR SEQ ID NO:24:

(i) SEQUENCE CHARACTERISTICS:

(A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:24:

CATGACCACA GTGCACAGGT SMARCTGCAG SAGTCWGG 38

(2) INFORMATION FOR SEQ ID NO:25:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:25:

GAGTCATTCT GCGGCCGCCC GTTTGATTTC CAGCTTGGTG CC 42

(2) INFORMATION FOR SEQ ID NO:26:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:26:

GAGTCATTCT GCGGCCGCCC GTTTTATTTC CAGCTTGGTC CC 42

(2) INFORMATION FOR SEQ ID NO:27:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:27:

GAGTCATTCT GCGGCCGCCC GTTTTATTTC CAACTTTGTC CC 42

(2) INFORMATION FOR SEQ ID NO:28:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:28:

GAGTCATTCT GCGGCCGCCC GTTTCAGCTC CAGCTTGGTC CC 42

(2) INFORMATION FOR SEQ ID NO:29:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:29:

GTCATTGTCG GCGCAACTAT CGGTATC 27

(2) INFORMATION FOR SEQ ID NO:30:

(i) SEQUENCE CHARACTERISTICS:
        (A) LENGTH: 21 base pairs
        (B) TYPE: nucleic acid (C) STRANDEDNESS: single
(D) TOPOLOGY: linear (xi) SEQUENCE DESCRIPTION: SEQ ID NO:30:

GTCGTCTTTC CAGACGTTAG T                                    21

(2) INFORMATION FOR SEQ ID NO:31:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO:31:

CAGGAAACAG CTATGAC                                          17

(2) INFORMATION FOR SEQ ID NO:32:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (xi) SEQUENCE DESCRIPTION: SEQ ID NO:32:

ACCGCCAGAG CCACCTCCGC C                                    21

(2) INFORMATION FOR SEQ ID NO:33:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (xi) SEQUENCE DESCRIPTION: SEQ ID NO:33:

GGCGGAGGTG GCTCTGGCGG T                                    21

(2) INFORMATION FOR SEQ ID NO:34:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ix) FEATURE:
      (A) NAME/KEY: misc_feature
      (B) LOCATION: 9
      (D) OTHER INFORMATION: /note= "T or C at position 9"

(ix) FEATURE:
      (A) NAME/KEY: misc_feature
      (B) LOCATION: 12
      (D) OTHER INFORMATION: /note= "A or G at position 12"

(xi) SEQUENCE DESCRIPTION: SEQ ID NO:34:

GACACGGTNG TNTATTACTG T                                    21

(2) INFORMATION FOR SEQ ID NO:35:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ix) FEATURE:
      (A) NAME/KEY: misc_feature (B) LOCATION: 10
(D) OTHER INFORMATION: /note= "C or T at position 10"

(ix) FEATURE:
(A) NAME/KEY: misc_feature
(B) LOCATION: 13
(D) OTHER INFORMATION: /note= "G or A at position 13"

(xi) SEQUENCE DESCRIPTION: SEQ ID NO:35:

ACAGTAATAN AGNGCCGTGT C   21

(2) INFORMATION FOR SEQ ID NO:36:

(i) SEQUENCE CHARACTERISTICS:
(A) LENGTH: 72 base pairs
(B) TYPE: nucleic acid
(C) STRANDEDNESS: single
(D) TOPOLOGY: linear (ix) FEATURE:
(A) NAME/KEY: CDS
(B) LOCATION: 1..69

(xi) SEQUENCE DESCRIPTION: SEQ ID NO:36:

```
CAT CAT CAT CAC CAT CAC GGG GCC GCA GAA CAA AAA CTC ATC TCA GAA   48
His His His His His His Gly Ala Ala Glu Gln Lys Leu Ile Ser Glu
 1               5                  10                  15

GAG GAT CTG AAT GGG GCC GCA TAG                                   72
Glu Asp Leu Asn Gly Ala Ala
             20
```

(2) INFORMATION FOR SEQ ID NO:37:

(i) SEQUENCE CHARACTERISTICS:
(A) LENGTH: 23 amino acids
(B) TYPE: amino acid
(D) TOPOLOGY: linear (ii) MOLECULE TYPE: protein (xi) SEQUENCE DESCRIPTION: SEQ ID NO:37:

```
His His His His His His Gly Ala Ala Glu Gln Lys Leu Ile Ser Glu
 1               5                  10                  15

Glu Asp Leu Asn Gly Ala Ala
             20
```

(2) INFORMATION FOR SEQ ID NO:38:

(i) SEQUENCE CHARACTERISTICS:
(A) LENGTH: 123 base pairs
(B) TYPE: nucleic acid
(C) STRANDEDNESS: single
(D) TOPOLOGY: linear (ix) FEATURE:
(A) NAME/KEY: CDS
(B) LOCATION: 1..120

(xi) SEQUENCE DESCRIPTION: SEQ ID NO:38:

```
CAC AGT GCA CAG GTC CAA CTG CAG GAG CTC GAG ATC AAA CGG GCG GCC   48
His Ser Ala Gln Val Gln Leu Gln Glu Leu Glu Ile Lys Arg Ala Ala
 1               5                  10                  15

GCA CAT CAT CAT CAC CAT CAC GGG GCC GCA GAA CAA AAA CTC ATC TCA   96
Ala His His His His His His Gly Ala Ala Glu Gln Lys Leu Ile Ser
                 20                  25                  30

GAA GAG GAT CTG AAT GGG GCC GCA TAG                              123
Glu Glu Asp Leu Asn Gly Ala Ala
         35                  40
```

(2) INFORMATION FOR SEQ ID NO:39:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO:39:

```
His Ser Ala Gln Val Gln Leu Gln Glu Leu Glu Ile Lys Arg Ala Ala
 1               5                  10                  15
Ala His His His His His His Gly Ala Ala Glu Gln Lys Leu Ile Ser
            20                  25                  30
Glu Glu Asp Leu Asn Gly Ala Ala
        35                  40
```

(2) INFORMATION FOR SEQ ID NO:40:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..129

(xi) SEQUENCE DESCRIPTION: SEQ ID NO:40:

```
GTG AAA AAA TTA TTA TTC GCA ATT CCT TTA GTT GTT CCT TTC TAT GCG      48
Val Lys Lys Leu Leu Phe Ala Ile Pro Leu Val Val Pro Phe Tyr Ala
 1               5                  10                  15

GCC CAG CCG GCC CAT CAT CAT CAC CAT CAC GGG GCC GCA GAA CAA AAA      96
Ala Gln Pro Ala His His His His His His Gly Ala Ala Glu Gln Lys
            20                  25                  30

CTC ATC TCA GAA GAG GAT CTG AAT GGG GCC GCA TAG                     132
Leu Ile Ser Glu Glu Asp Leu Asn Gly Ala Ala
        35                  40
```

(2) INFORMATION FOR SEQ ID NO:41:

(i) SEQUENCE CHARACTERISTICS:
        (A) LENGTH: 43 amino acids
        (B) TYPE: amino acid
        (D) TOPOLOGY: linear (ii) MOLECULE TYPE: protein (xi) SEQUENCE DESCRIPTION: SEQ ID NO:41:

```
Val Lys Lys Leu Leu Phe Ala Ile Pro Leu Val Val Pro Phe Tyr Ala
 1               5                  10                  15
Ala Gln Pro Ala His His His His His His Gly Ala Ala Glu Gln Lys
            20                  25                  30
Leu Ile Ser Glu Glu Asp Leu Asn Gly Ala Ala
        35                  40
```

(2) INFORMATION FOR SEQ ID NO:42:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ix) FEATURE:
        (A) NAME/KEY: CDS ( B ) LOCATION: 1..48

( x i ) SEQUENCE DESCRIPTION: SEQ ID NO:42:

| ATG | GCC | CAG | GTC | CAA | CTG | CAG | GAG | CTC | GAG | ATC | AAA | CGG | GCG | GCC | GCA | 48 |
|-----|-----|-----|-----|-----|-----|-----|-----|-----|-----|-----|-----|-----|-----|-----|-----|-----|
| Met | Ala | Gln | Val | Gln | Leu | Gln | Glu | Leu | Glu | Ile | Lys | Arg | Ala | Ala | Ala | |
| 1 | | | | 5 | | | | | 10 | | | | | 15 | | |

( 2 ) INFORMATION FOR SEQ ID NO:43:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( x i ) SEQUENCE DESCRIPTION: SEQ ID NO:43:

| Met | Ala | Gln | Val | Gln | Leu | Gln | Glu | Leu | Glu | Ile | Lys | Arg | Ala | Ala | Ala |
|-----|-----|-----|-----|-----|-----|-----|-----|-----|-----|-----|-----|-----|-----|-----|-----|
| 1 | | | | 5 | | | | | 10 | | | | | 15 | |

( 2 ) INFORMATION FOR SEQ ID NO:44:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..276

( x i ) SEQUENCE DESCRIPTION: SEQ ID NO:44:

| TCC | TCC | TTA | TCT | GCC | TCT | CTG | GGA | GAA | AGA | GTC | AGT | CTC | ACT | TGT | CGG | 48 |
|-----|-----|-----|-----|-----|-----|-----|-----|-----|-----|-----|-----|-----|-----|-----|-----|-----|
| Ser | Ser | Leu | Ser | Ala | Ser | Leu | Gly | Glu | Arg | Val | Ser | Leu | Thr | Cys | Arg | |
| 1 | | | | 5 | | | | | 10 | | | | | 15 | | |
| GCA | AGT | CAG | GAC | ATT | GGT | AGT | AGC | TTA | AAC | TGG | CTT | CAG | CAG | GAA | CCA | 96 |
| Ala | Ser | Gln | Asp | Ile | Gly | Ser | Ser | Leu | Asn | Trp | Leu | Gln | Gln | Glu | Pro | |
| | | | | 20 | | | | | 25 | | | | | 30 | | |
| GAT | GGA | ACT | ATT | AAA | CGC | CTG | ATC | TAC | GCC | ACA | TCC | AGT | TTA | GAT | TCT | 144 |
| Asp | Gly | Thr | Ile | Lys | Arg | Leu | Ile | Tyr | Ala | Thr | Ser | Ser | Leu | Asp | Ser | |
| | | 35 | | | | | 40 | | | | | 45 | | | | |
| GGT | GTC | CCC | AAA | AGG | TTC | AGT | GGC | AGT | AGG | TCT | GGG | TCA | GAT | TAT | TCT | 192 |
| Gly | Val | Pro | Lys | Arg | Phe | Ser | Gly | Ser | Arg | Ser | Gly | Ser | Asp | Tyr | Ser | |
| | 50 | | | | | 55 | | | | | 60 | | | | | |
| CTC | ACC | ATC | AGC | AGC | CTT | GAG | TCT | GAA | GAT | TTT | GTA | GAC | TAT | TAC | TGT | 240 |
| Leu | Thr | Ile | Ser | Ser | Leu | Glu | Ser | Glu | Asp | Phe | Val | Asp | Tyr | Tyr | Cys | |
| 65 | | | | | 70 | | | | | 75 | | | | | 80 | |
| CTA | CAA | TAT | GCT | AGT | TCT | CCT | TAC | ACG | TTC | GAA | GGG | | | | | 276 |
| Leu | Gln | Tyr | Ala | Ser | Ser | Pro | Tyr | Thr | Phe | Glu | Gly | | | | | |
| | | | | 85 | | | | | 90 | | | | | | | |

( 2 ) INFORMATION FOR SEQ ID NO:45:

( i ) SEQUENCE CHARACTERISTICS:
        ( A ) LENGTH: 92 amino acids
        ( B ) TYPE: amino acid
        ( D ) TOPOLOGY: linear ( i i ) MOLECULE TYPE: protein ( x i ) SEQUENCE DESCRIPTION: SEQ ID NO:45:

| Ser | Ser | Leu | Ser | Ala | Ser | Leu | Gly | Glu | Arg | Val | Ser | Leu | Thr | Cys | Arg |
|-----|-----|-----|-----|-----|-----|-----|-----|-----|-----|-----|-----|-----|-----|-----|-----|
| 1 | | | | 5 | | | | | 10 | | | | | 15 | |
| Ala | Ser | Gln | Asp | Ile | Gly | Ser | Ser | Leu | Asn | Trp | Leu | Gln | Gln | Glu | Pro |
| | | | | 20 | | | | | 25 | | | | | 30 | |

```
Asp Gly Thr Ile Lys Arg Leu Ile Tyr Ala Thr Ser Ser Leu Asp Ser
         35                  40                  45

Gly Val Pro Lys Arg Phe Ser Gly Ser Arg Ser Gly Ser Asp Tyr Ser
         50                  55                  60

Leu Thr Ile Ser Ser Leu Glu Ser Glu Asp Phe Val Asp Tyr Tyr Cys
 65                  70                  75                  80

Leu Gln Tyr Ala Ser Ser Pro Tyr Thr Phe Glu Gly
             85                  90
```

(2) INFORMATION FOR SEQ ID NO:46:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..276

(xi) SEQUENCE DESCRIPTION: SEQ ID NO:46:

```
TCT TCC ATG TAT GCA TCT CTA GGA GAG ATA GTC ACT ATC ACT TGC AAG    48
Ser Ser Met Tyr Ala Ser Leu Gly Glu Ile Val Thr Ile Thr Cys Lys
 1               5                  10                  15

GCG AGT CAG GAC ATT AAT AGC TAT TTA AGC TGG TTC CAG CAG AAA CCA    96
Ala Ser Gln Asp Ile Asn Ser Tyr Leu Ser Trp Phe Gln Gln Lys Pro
             20                  25                  30

GGG AAA TCT CCT AAG ACC CTG ATC TAT CGT GCA AAC AGA TTG GTA GAT   144
Gly Lys Ser Pro Lys Thr Leu Ile Tyr Arg Ala Asn Arg Leu Val Asp
         35                  40                  45

GGG GTC CCA TCA CGG TTC AGT GGC AGT GGA TCT GGG CAA GAT TAT TCT   192
Gly Val Pro Ser Arg Phe Ser Gly Ser Gly Ser Gly Gln Asp Tyr Ser
         50                  55                  60

CTC ACC ATC AGC AGC CTG GAG TAT GAA GAT ATG GGA ATT TAT TAT TGT   240
Leu Thr Ile Ser Ser Leu Glu Tyr Glu Asp Met Gly Ile Tyr Tyr Cys
 65                  70                  75                  80

CTA CAG TAT GAT GAG TTT CCG TAC ACG TTC GGA GGG                   276
Leu Gln Tyr Asp Glu Phe Pro Tyr Thr Phe Gly Gly
             85                  90
```

(2) INFORMATION FOR SEQ ID NO:47:

(i) SEQUENCE CHARACTERISTICS:
        (A) LENGTH: 92 amino acids
        (B) TYPE: amino acid
        (D) TOPOLOGY: linear (ii) MOLECULE TYPE: protein (xi) SEQUENCE DESCRIPTION: SEQ ID NO:47:

```
Ser Ser Met Tyr Ala Ser Leu Gly Glu Ile Val Thr Ile Thr Cys Lys
 1               5                  10                  15

Ala Ser Gln Asp Ile Asn Ser Tyr Leu Ser Trp Phe Gln Gln Lys Pro
             20                  25                  30

Gly Lys Ser Pro Lys Thr Leu Ile Tyr Arg Ala Asn Arg Leu Val Asp
         35                  40                  45

Gly Val Pro Ser Arg Phe Ser Gly Ser Gly Ser Gly Gln Asp Tyr Ser
         50                  55                  60

Leu Thr Ile Ser Ser Leu Glu Tyr Glu Asp Met Gly Ile Tyr Tyr Cys
 65                  70                  75                  80

Leu Gln Tyr Asp Glu Phe Pro Tyr Thr Phe Gly Gly
             85                  90
```

( 2 ) INFORMATION FOR SEQ ID NO:48:

( i ) SEQUENCE CHARACTERISTICS:
        ( A ) LENGTH: 273 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..273

( x i ) SEQUENCE DESCRIPTION: SEQ ID NO:48:

```
GCT  TCT  TTG  GCT  GTG  TCT  CTG  GGA  CAG  AGG  GCC  ACC  ATA  TCC  TGC  AGA      48
Ala  Ser  Leu  Ala  Val  Ser  Leu  Gly  Gln  Arg  Ala  Thr  Ile  Ser  Cys  Arg
 1              5                        10                       15

GCC  AGT  GAA  AAT  GGT  GAT  AGT  TAT  GGC  AAT  AGT  TTT  ATG  CAC  TGG  TAC      96
Ala  Ser  Glu  Asn  Gly  Asp  Ser  Tyr  Gly  Asn  Ser  Phe  Met  His  Trp  Tyr
               20                        25                       30

CAG  CAG  AAA  TCA  GGA  CAG  CCA  CCC  AAA  CTC  CTC  ATC  TAT  CTT  GCA  TCC     144
Gln  Gln  Lys  Ser  Gly  Gln  Pro  Pro  Lys  Leu  Leu  Ile  Tyr  Leu  Ala  Ser
          35                        40                       45

AAC  CTA  CAA  TCT  GGG  GTC  CCT  GCC  AGG  TTC  AGT  GGC  AGC  GGG  TCT  AGG     192
Asn  Leu  Gln  Ser  Gly  Val  Pro  Ala  Arg  Phe  Ser  Gly  Ser  Gly  Ser  Arg
     50                        55                       60

ACA  GAC  TTC  ACC  CTC  ACC  ATT  GAT  CCT  GTG  GAG  GCT  GAT  GAT  GCT  GCA     240
Thr  Asp  Phe  Thr  Leu  Thr  Ile  Asp  Pro  Val  Glu  Ala  Asp  Asp  Ala  Ala
 65                       70                        75                       80

ACC  TAT  TAC  TGT  CTG  CAA  AAT  ACT  GAG  GAT  CCG                              273
Thr  Tyr  Tyr  Cys  Leu  Gln  Asn  Thr  Glu  Asp  Pro
                    85                        90
```

( 2 ) INFORMATION FOR SEQ ID NO:49:

( i ) SEQUENCE CHARACTERISTICS:
        ( A ) LENGTH: 91 amino acids
        ( B ) TYPE: amino acid
        ( D ) TOPOLOGY: linear ( i i ) MOLECULE TYPE: protein ( x i ) SEQUENCE DESCRIPTION: SEQ ID NO:49:

```
Ala  Ser  Leu  Ala  Val  Ser  Leu  Gly  Gln  Arg  Ala  Thr  Ile  Ser  Cys  Arg
 1              5                        10                       15

Ala  Ser  Glu  Asn  Gly  Asp  Ser  Tyr  Gly  Asn  Ser  Phe  Met  His  Trp  Tyr
               20                        25                       30

Gln  Gln  Lys  Ser  Gly  Gln  Pro  Pro  Lys  Leu  Leu  Ile  Tyr  Leu  Ala  Ser
          35                        40                       45

Asn  Leu  Gln  Ser  Gly  Val  Pro  Ala  Arg  Phe  Ser  Gly  Ser  Gly  Ser  Arg
     50                        55                       60

Thr  Asp  Phe  Thr  Leu  Thr  Ile  Asp  Pro  Val  Glu  Ala  Asp  Asp  Ala  Ala
 65                       70                        75                       80

Thr  Tyr  Tyr  Cys  Leu  Gln  Asn  Thr  Glu  Asp  Pro
                    85                        90
```

( 2 ) INFORMATION FOR SEQ ID NO:50:

( i ) SEQUENCE CHARACTERISTICS:
        ( A ) LENGTH: 195 base pairs
        ( B ) TYPE: nucleic acid
        ( C ) STRANDEDNESS: single
        ( D ) TOPOLOGY: linear ( i x ) FEATURE:

(A) NAME/KEY: CDS
(B) LOCATION: 1..195

(xi) SEQUENCE DESCRIPTION: SEQ ID NO:50:

| CTC | TCC | CTG | CCT | GTC | AGT | CTT | GGA | GAT | CAA | GCC | TCC | ATC | TCT | TGC | AGA | 48 |
| Leu | Ser | Leu | Pro | Val | Ser | Leu | Gly | Asp | Gln | Ala | Ser | Ile | Ser | Cys | Arg | |
| 1 | | | | 5 | | | | | 10 | | | | | 15 | | |

| TCT | AGT | CAG | AGC | CTT | GTA | CAC | AGT | CCT | GGA | AAC | ACC | TAT | TTA | CAT | TGG | 96 |
| Ser | Ser | Gln | Ser | Leu | Val | His | Ser | Pro | Gly | Asn | Thr | Tyr | Leu | His | Trp | |
| | | | 20 | | | | | 25 | | | | | 30 | | | |

| CTG | CAG | AAG | CCA | GGC | CAG | TCT | CCA | AAG | CTC | CTG | ATC | TAC | AAA | GTT | TCC | 144 |
| Leu | Gln | Lys | Pro | Gly | Gln | Ser | Pro | Lys | Leu | Leu | Ile | Tyr | Lys | Val | Ser | |
| | | | 35 | | | | | 40 | | | | | 45 | | | |

| AAC | CGA | TTT | TCT | GGG | GTC | CCA | GAC | AGG | TTC | AGT | GGC | AGT | GGA | TCA | GGG | 192 |
| Asn | Arg | Phe | Ser | Gly | Val | Pro | Asp | Arg | Phe | Ser | Gly | Ser | Gly | Ser | Gly | |
| | | 50 | | | | | 55 | | | | | 60 | | | | |

ACA          195
Thr
65

(2) INFORMATION FOR SEQ ID NO:51:

(i) SEQUENCE CHARACTERISTICS:
       (A) LENGTH: 65 amino acids
       (B) TYPE: amino acid
       (D) TOPOLOGY: linear (ii) MOLECULE TYPE: protein (xi) SEQUENCE DESCRIPTION: SEQ ID NO:51:

| Leu | Ser | Leu | Pro | Val | Ser | Leu | Gly | Asp | Gln | Ala | Ser | Ile | Ser | Cys | Arg |
| 1 | | | | 5 | | | | | 10 | | | | | 15 | |

| Ser | Ser | Gln | Ser | Leu | Val | His | Ser | Pro | Gly | Asn | Thr | Tyr | Leu | His | Trp |
| | | | 20 | | | | | 25 | | | | | 30 | | |

| Leu | Gln | Lys | Pro | Gly | Gln | Ser | Pro | Lys | Leu | Leu | Ile | Tyr | Lys | Val | Ser |
| | | | 35 | | | | | 40 | | | | | 45 | | |

| Asn | Arg | Phe | Ser | Gly | Val | Pro | Asp | Arg | Phe | Ser | Gly | Ser | Gly | Ser | Gly |
| | | 50 | | | | | 55 | | | | | 60 | | | |

Thr
65

(2) INFORMATION FOR SEQ ID NO:52:

(i) SEQUENCE CHARACTERISTICS:
       (A) LENGTH: 276 base pairs
       (B) TYPE: nucleic acid
       (C) STRANDEDNESS: single
       (D) TOPOLOGY: linear (ix) FEATURE:
       (A) NAME/KEY: CDS
       (B) LOCATION: 1..276

(xi) SEQUENCE DESCRIPTION: SEQ ID NO:52:

| TCC | TCC | TTA | TCT | GCC | TCT | CTG | GGA | GAA | AGA | GTC | AGT | CTC | ACT | TGT | CGG | 48 |
| Ser | Ser | Leu | Ser | Ala | Ser | Leu | Gly | Glu | Arg | Val | Ser | Leu | Thr | Cys | Arg | |
| 1 | | | | 5 | | | | | 10 | | | | | 15 | | |

| GCA | AGT | CAG | GAC | ATT | GGT | AGT | AGC | TTA | AAC | TGG | CTT | CAG | CAG | GAA | CCA | 96 |
| Ala | Ser | Gln | Asp | Ile | Gly | Ser | Ser | Leu | Asn | Trp | Leu | Gln | Gln | Glu | Pro | |
| | | | 20 | | | | | 25 | | | | | 30 | | | |

| GAT | GGA | ACT | ATT | AAA | CGC | CTG | ATC | TAC | GCC | ACA | TCC | AGT | TTA | GAT | TCT | 144 |
| Asp | Gly | Thr | Ile | Lys | Arg | Leu | Ile | Tyr | Ala | Thr | Ser | Ser | Leu | Asp | Ser | |
| | | | 35 | | | | | 40 | | | | | 45 | | | |

| GGT | GTC | CCC | AAA | AGG | TTC | AGT | GGC | AGT | AGG | TCT | GGG | TCA | GAT | TAT | TCT | 192 |

```
Gly  Val  Pro  Lys  Arg  Phe  Ser  Gly  Ser  Arg  Ser  Gly  Ser  Asp  Tyr  Ser
          50                       55                      60

CTC  ACC  ATC  AGC  AGC  CTT  GAG  TCT  GAA  GAT  TTT  GTA  GAC  TAT  TAC  TGT         240
Leu  Thr  Ile  Ser  Ser  Leu  Glu  Ser  Glu  Asp  Phe  Val  Asp  Tyr  Tyr  Cys
 65                       70                      75                       80

CTA  CAA  TAT  GCT  AGT  TCT  CCT  TAC  ACG  TTC  GGA  GGG                             276
Leu  Gln  Tyr  Ala  Ser  Ser  Pro  Tyr  Thr  Phe  Gly  Gly
                    85                       90
```

( 2 ) INFORMATION FOR SEQ ID NO:53:

( i ) SEQUENCE CHARACTERISTICS:
        ( A ) LENGTH: 92 amino acids
        ( B ) TYPE: amino acid
        ( D ) TOPOLOGY: linear ( i i ) MOLECULE TYPE: protein ( x i ) SEQUENCE DESCRIPTION: SEQ ID NO:53:

```
Ser  Ser  Leu  Ser  Ala  Ser  Leu  Gly  Glu  Arg  Val  Ser  Leu  Thr  Cys  Arg
 1                    5                      10                       15

Ala  Ser  Gln  Asp  Ile  Gly  Ser  Ser  Leu  Asn  Trp  Leu  Gln  Gln  Glu  Pro
          20                      25                       30

Asp  Gly  Thr  Ile  Lys  Arg  Leu  Ile  Tyr  Ala  Thr  Ser  Ser  Leu  Asp  Ser
          35                      40                       45

Gly  Val  Pro  Lys  Arg  Phe  Ser  Gly  Ser  Arg  Ser  Gly  Ser  Asp  Tyr  Ser
          50                      55                       60

Leu  Thr  Ile  Ser  Ser  Leu  Glu  Ser  Glu  Asp  Phe  Val  Asp  Tyr  Tyr  Cys
 65                   70                      75                        80

Leu  Gln  Tyr  Ala  Ser  Ser  Pro  Tyr  Thr  Phe  Gly  Gly
                    85                      90
```

( 2 ) INFORMATION FOR SEQ ID NO:54:

( i ) SEQUENCE CHARACTERISTICS:
        ( A ) LENGTH: 348 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..348

( x i ) SEQUENCE DESCRIPTION: SEQ ID NO:54:

```
CAG  GTC  CAG  CTG  CAG  CAG  TCA  GGA  CCT  GAG  CTG  GTG  AAG  CCT  GGG  GCT          48
Gln  Val  Gln  Leu  Gln  Gln  Ser  Gly  Pro  Glu  Leu  Val  Lys  Pro  Gly  Ala
 1                    5                      10                       15

TCA  GTG  AAG  GTA  TCC  TGC  AAG  GCT  TCT  GGT  TAT  GCA  TTC  ACT  AAC  TAC          96
Ser  Val  Lys  Val  Ser  Cys  Lys  Ala  Ser  Gly  Tyr  Ala  Phe  Thr  Asn  Tyr
          20                      25                       30

AAC  ATA  TAC  TGG  GTG  AAG  CAG  AGC  CAT  GGA  AAG  AGT  CTT  GAG  TGG  ATT         144
Asn  Ile  Tyr  Trp  Val  Lys  Gln  Ser  His  Gly  Lys  Ser  Leu  Glu  Trp  Ile
          35                      40                       45

GGA  TAT  ATC  GAT  CCT  TAC  AGT  GGT  GGT  TCT  AGC  TAC  AAC  CAG  AAG  TTC         192
Gly  Tyr  Ile  Asp  Pro  Tyr  Ser  Gly  Gly  Ser  Ser  Tyr  Asn  Gln  Lys  Phe
          50                      55                       60

AAG  GGC  AAG  GCC  ACA  TTG  ACT  GTT  GAC  AAG  TCC  TCC  AGC  ACA  GCC  TAC         240
Lys  Gly  Lys  Ala  Thr  Leu  Thr  Val  Asp  Lys  Ser  Ser  Ser  Thr  Ala  Tyr
 65                   70                      75                        80

ATG  CAT  CTC  AAC  AGC  CTG  ACA  TCT  GAG  GAC  TCT  GCA  GTC  TAT  TAC  TGT         288
Met  His  Leu  Asn  Ser  Leu  Thr  Ser  Glu  Asp  Ser  Ala  Val  Tyr  Tyr  Cys
                    85                      90                       95
```

| GCG | GGG | GGC | AAT | CCC | CGT | TTT | GCT | TTC | TGG | GGC | CAA | GGG | ACC | ACG | GTC | 336 |
| Ala | Gly | Gly | Asn | Pro | Arg | Phe | Ala | Phe | Trp | Gly | Gln | Gly | Thr | Thr | Val | |
|     |     |     | 100 |     |     |     | 105 |     |     |     |     |     | 110 |     |     | |

| ACC | GTC | TCC | TCA | 348 |
| Thr | Val | Ser | Ser | |
|     |     | 115 |     | |

( 2 ) INFORMATION FOR SEQ ID NO:55:

( i ) SEQUENCE CHARACTERISTICS:
        ( A ) LENGTH: 116 amino acids
        ( B ) TYPE: amino acid
        ( D ) TOPOLOGY: linear ( i i ) MOLECULE TYPE: protein ( x i ) SEQUENCE DESCRIPTION: SEQ ID NO:55:

| Gln | Val | Gln | Leu | Gln | Gln | Ser | Gly | Pro | Glu | Leu | Val | Lys | Pro | Gly | Ala |
| 1   |     |     |     | 5   |     |     |     |     | 10  |     |     |     |     | 15  |     |

| Ser | Val | Lys | Val | Ser | Cys | Lys | Ala | Ser | Gly | Tyr | Ala | Phe | Thr | Asn | Tyr |
|     |     |     | 20  |     |     |     |     | 25  |     |     |     |     | 30  |     |     |

| Asn | Ile | Tyr | Trp | Val | Lys | Gln | Ser | His | Gly | Lys | Ser | Leu | Glu | Trp | Ile |
|     |     | 35  |     |     |     |     | 40  |     |     |     |     | 45  |     |     |     |

| Gly | Tyr | Ile | Asp | Pro | Tyr | Ser | Gly | Gly | Ser | Ser | Tyr | Asn | Gln | Lys | Phe |
|     | 50  |     |     |     |     | 55  |     |     |     |     | 60  |     |     |     |     |

| Lys | Gly | Lys | Ala | Thr | Leu | Thr | Val | Asp | Lys | Ser | Ser | Ser | Thr | Ala | Tyr |
| 65  |     |     |     |     | 70  |     |     |     |     | 75  |     |     |     |     | 80  |

| Met | His | Leu | Asn | Ser | Leu | Thr | Ser | Glu | Asp | Ser | Ala | Val | Tyr | Tyr | Cys |
|     |     |     |     | 85  |     |     |     |     | 90  |     |     |     |     | 95  |     |

| Ala | Gly | Gly | Asn | Pro | Arg | Phe | Ala | Phe | Trp | Gly | Gln | Gly | Thr | Thr | Val |
|     |     |     | 100 |     |     |     | 105 |     |     |     |     |     | 110 |     |     |

| Thr | Val | Ser | Ser |
|     |     | 115 |     |

( 2 ) INFORMATION FOR SEQ ID NO:56:

( i ) SEQUENCE CHARACTERISTICS:
        ( A ) LENGTH: 324 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..324

( x i ) SEQUENCE DESCRIPTION: SEQ ID NO:56:

| CAG | CAG | TCT | GGT | CCT | GAG | CTG | GTA | AAG | CCT | GGG | GCT | TCA | GTG | AAG | ATG | 48 |
| Gln | Gln | Ser | Gly | Pro | Glu | Leu | Val | Lys | Pro | Gly | Ala | Ser | Val | Lys | Met | |
| 1   |     |     |     | 5   |     |     |     |     | 10  |     |     |     |     | 15  |     | |

| TCC | TGC | AAG | GCT | TCT | GGA | TAC | ACA | TTC | ACA | AGT | TAT | GTT | ATG | CAC | TGG | 96 |
| Ser | Cys | Lys | Ala | Ser | Gly | Tyr | Thr | Phe | Thr | Ser | Tyr | Val | Met | His | Trp | |
|     |     |     |     | 20  |     |     |     |     | 25  |     |     |     |     | 30  |     | |

| GTG | AAG | CAG | AAG | CCT | GGG | CAG | GGC | CTT | GAG | TGG | ATT | GGA | GAT | ATT | AAT | 144 |
| Val | Lys | Gln | Lys | Pro | Gly | Gln | Gly | Leu | Glu | Trp | Ile | Gly | Asp | Ile | Asn | |
|     |     |     | 35  |     |     |     |     | 40  |     |     |     |     | 45  |     |     | |

| CCT | TAC | AAT | GAT | GGT | ACT | AAG | TAC | AAT | GAG | AAG | TTC | AAA | GGC | AAG | GCC | 192 |
| Pro | Tyr | Asn | Asp | Gly | Thr | Lys | Tyr | Asn | Glu | Lys | Phe | Lys | Gly | Lys | Ala | |
|     | 50  |     |     |     |     | 55  |     |     |     |     | 60  |     |     |     |     | |

| ACA | CTG | ACT | TCA | GAC | AAA | TCC | TCC | AAC | ACA | GCC | TAC | ATG | GAG | CTC | AGC | 240 |
| Thr | Leu | Thr | Ser | Asp | Lys | Ser | Ser | Asn | Thr | Ala | Tyr | Met | Glu | Leu | Ser | |
| 65  |     |     |     |     | 70  |     |     |     |     | 75  |     |     |     |     | 80  | |

| AGC | CTG | ACC | TCT | GAG | GAC | TCT | GCG | GTC | TAT | TAC | TGT | GCG | GGG | TTT | GCT | 288 |

```
Ser  Leu  Thr  Ser  Glu  Asp  Ser  Ala  Val  Tyr  Tyr  Cys  Ala  Gly  Phe  Ala
               85                      90                         95

CAC  TGG  GGC  CAA  GGG  ACC  ACG  GTC  ACC  GTC  TCC  TCA                          324
His  Trp  Gly  Gln  Gly  Thr  Thr  Val  Thr  Val  Ser  Ser
               100                     105
```

( 2 ) INFORMATION FOR SEQ ID NO:57:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:57:

```
Gln  Gln  Ser  Gly  Pro  Glu  Leu  Val  Lys  Pro  Gly  Ala  Ser  Val  Lys  Met
1                    5                     10                         15

Ser  Cys  Lys  Ala  Ser  Gly  Tyr  Thr  Phe  Thr  Ser  Tyr  Val  Met  His  Trp
               20                     25                         30

Val  Lys  Gln  Lys  Pro  Gly  Gln  Gly  Leu  Glu  Trp  Ile  Gly  Asp  Ile  Asn
               35                     40                         45

Pro  Tyr  Asn  Asp  Gly  Thr  Lys  Tyr  Asn  Glu  Lys  Phe  Lys  Gly  Lys  Ala
     50                       55                         60

Thr  Leu  Thr  Ser  Asp  Lys  Ser  Ser  Asn  Thr  Ala  Tyr  Met  Glu  Leu  Ser
65                       70                         75                       80

Ser  Leu  Thr  Ser  Glu  Asp  Ser  Ala  Val  Tyr  Tyr  Cys  Ala  Gly  Phe  Ala
               85                      90                         95

His  Trp  Gly  Gln  Gly  Thr  Thr  Val  Thr  Val  Ser  Ser
               100                     105
```

( 2 ) INFORMATION FOR SEQ ID NO:58:

( i ) SEQUENCE CHARACTERISTICS:
        ( A ) LENGTH: 354 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..339

( x i ) SEQUENCE DESCRIPTION: SEQ ID NO:58:

```
CAG  GTG  CAG  CTG  CAG  CAG  TCT  GGG  GCT  GAA  CTG  GCA  AAA  CCT  GGG  GCC      48
Gln  Val  Gln  Leu  Gln  Gln  Ser  Gly  Ala  Glu  Leu  Ala  Lys  Pro  Gly  Ala
1                    5                     10                         15

TCA  GTG  AAG  ATG  TCC  TGC  AAG  GCT  TCT  GGC  TAC  ACC  TTT  ACT  AGC  TAC      96
Ser  Val  Lys  Met  Ser  Cys  Lys  Ala  Ser  Gly  Tyr  Thr  Phe  Thr  Ser  Tyr
               20                     25                         30

TGG  ATG  CAC  TGG  GTA  AAA  CAG  AGG  CCT  GGA  CAG  GGT  CTG  GAA  TGG  ATT     144
Trp  Met  His  Trp  Val  Lys  Gln  Arg  Pro  Gly  Gln  Gly  Leu  Glu  Trp  Ile
               35                     40                         45

GGA  TAC  ATT  AAT  CCT  AGC  ACT  GGT  TAT  ACT  GAG  TAC  AAT  CAG  AAG  TTC     192
Gly  Tyr  Ile  Asn  Pro  Ser  Thr  Gly  Tyr  Thr  Glu  Tyr  Asn  Gln  Lys  Phe
     50                       55                         60

AAG  GAC  AAG  GCC  ACA  TTG  ACT  GCA  GAC  AAA  TCC  TCC  AGC  ACA  GCC  TAC     240
Lys  Asp  Lys  Ala  Thr  Leu  Thr  Ala  Asp  Lys  Ser  Ser  Ser  Thr  Ala  Tyr
65                       70                         75                       80

ATG  CAA  CTG  AGC  AGC  CTG  ACA  TCT  GAG  GAC  TCT  GCA  GTC  TAT  TAC  TGT     288
Met  Gln  Leu  Ser  Ser  Leu  Thr  Ser  Glu  Asp  Ser  Ala  Val  Tyr  Tyr  Cys
               85                      90                         95

GCA  AGA  ACG  TTA  TAT  TAC  TAT  GCT  ATG  GAC  TAC  TGG  GGC  CAA  GGG  ACC     336
```

| Ala | Arg | Thr | Leu | Tyr | Tyr | Tyr | Ala | Met | Asp | Tyr | Trp | Gly | Gln | Gly | Thr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

```
ACC GTCACCGTCT CCTCA                                                         354
Thr
```

( 2 ) INFORMATION FOR SEQ ID NO:59:

( i ) SEQUENCE CHARACTERISTICS:
    ( A ) LENGTH: 113 amino acids
    ( B ) TYPE: amino acid
    ( D ) TOPOLOGY: linear ( i i ) MOLECULE TYPE: protein ( x i ) SEQUENCE DESCRIPTION: SEQ ID NO:59:

| Gln | Val | Gln | Leu | Gln | Gln | Ser | Gly | Ala | Glu | Leu | Ala | Lys | Pro | Gly | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Val | Lys | Met | Ser | Cys | Lys | Ala | Ser | Gly | Tyr | Thr | Phe | Thr | Ser | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Trp | Met | His | Trp | Val | Lys | Gln | Arg | Pro | Gly | Gln | Gly | Leu | Glu | Trp | Ile |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Gly | Tyr | Ile | Asn | Pro | Ser | Thr | Gly | Tyr | Thr | Glu | Tyr | Asn | Gln | Lys | Phe |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Lys | Asp | Lys | Ala | Thr | Leu | Thr | Ala | Asp | Lys | Ser | Ser | Ser | Thr | Ala | Tyr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Met | Gln | Leu | Ser | Ser | Leu | Thr | Ser | Glu | Asp | Ser | Ala | Val | Tyr | Tyr | Cys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ala | Arg | Thr | Leu | Tyr | Tyr | Tyr | Ala | Met | Asp | Tyr | Trp | Gly | Gln | Gly | Thr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

Thr ( 2 ) INFORMATION FOR SEQ ID NO:60:

( i ) SEQUENCE CHARACTERISTICS:
    ( A ) LENGTH: 234 base pairs
    ( B ) TYPE: nucleic acid
    ( C ) STRANDEDNESS: double
    ( D ) TOPOLOGY: linear ( i x ) FEATURE:
    ( A ) NAME/KEY: CDS
    ( B ) LOCATION: 1..234

( x i ) SEQUENCE DESCRIPTION: SEQ ID NO:60:

| GAA | GTC | TCC | TGC | AAG | GCT | TCT | GGA | GGC | ACC | TTC | AGC | AGC | TAT | GCT | ATC | 48 |
|-----|-----|-----|-----|-----|-----|-----|-----|-----|-----|-----|-----|-----|-----|-----|-----|-----|
| Glu | Val | Ser | Cys | Lys | Ala | Ser | Gly | Gly | Thr | Phe | Ser | Ser | Tyr | Ala | Ile |    |
| 1   |     |     |     | 5   |     |     |     |     | 10  |     |     |     |     | 15  |     |    |

| AGC | TGG | GTG | CGA | CAG | GCC | CCT | GGA | CAA | GGG | CTT | GAG | TGG | ATG | GGA | GGG | 96 |
|-----|-----|-----|-----|-----|-----|-----|-----|-----|-----|-----|-----|-----|-----|-----|-----|-----|
| Ser | Trp | Val | Arg | Gln | Ala | Pro | Gly | Gln | Gly | Leu | Glu | Trp | Met | Gly | Gly |    |
|     |     |     | 20  |     |     |     |     | 25  |     |     |     |     | 30  |     |     |    |

| ATC | AAC | GCT | GGC | AAT | GGT | AAC | ACA | AAA | TAT | TCA | CAG | AAG | TTC | CAG | GGC | 144 |
|-----|-----|-----|-----|-----|-----|-----|-----|-----|-----|-----|-----|-----|-----|-----|-----|-----|
| Ile | Asn | Ala | Gly | Asn | Gly | Asn | Thr | Lys | Tyr | Ser | Gln | Lys | Phe | Gln | Gly |    |
|     |     |     | 35  |     |     |     |     | 40  |     |     |     |     | 45  |     |     |    |

| AGA | GTC | ACC | ATT | ACC | AGG | GAC | ACA | TCC | GCG | AGC | ACA | GCC | TAC | ATG | GAG | 192 |
|-----|-----|-----|-----|-----|-----|-----|-----|-----|-----|-----|-----|-----|-----|-----|-----|-----|
| Arg | Val | Thr | Ile | Thr | Arg | Asp | Thr | Ser | Ala | Ser | Thr | Ala | Tyr | Met | Glu |    |
|     |     | 50  |     |     |     |     | 55  |     |     |     |     | 60  |     |     |     |    |

| CTG | AGC | AGC | CTG | AGA | TCT | GAA | GAC | ACA | GCT | GTG | TAT | TAC | TGT |     |     | 234 |
|-----|-----|-----|-----|-----|-----|-----|-----|-----|-----|-----|-----|-----|-----|-----|-----|-----|
| Leu | Ser | Ser | Leu | Arg | Ser | Glu | Asp | Thr | Ala | Val | Tyr | Tyr | Cys |     |     |     |
| 65  |     |     |     |     | 70  |     |     |     |     | 75  |     |     |     |     |     |     |

( 2 ) INFORMATION FOR SEQ ID NO:61:

( i ) SEQUENCE CHARACTERISTICS:

(A) LENGTH: 78 amino acids
(B) TYPE: amino acid
(D) TOPOLOGY: linear (i i) MOLECULE TYPE: protein (x i) SEQUENCE DESCRIPTION: SEQ ID NO:61:

| Glu | Val | Ser | Cys | Lys | Ala | Ser | Gly | Gly | Thr | Phe | Ser | Ser | Tyr | Ala | Ile |
|---|---|---|---|---|---|---|---|---|---|---|---|---|---|---|---|
| 1 | | | | 5 | | | | | 10 | | | | | 15 | |

| Ser | Trp | Val | Arg | Gln | Ala | Pro | Gly | Gln | Gly | Leu | Glu | Trp | Met | Gly | Gly |
|---|---|---|---|---|---|---|---|---|---|---|---|---|---|---|---|
| | | | 20 | | | | | 25 | | | | | 30 | | |

| Ile | Asn | Ala | Gly | Asn | Gly | Asn | Thr | Lys | Tyr | Ser | Gln | Lys | Phe | Gln | Gly |
|---|---|---|---|---|---|---|---|---|---|---|---|---|---|---|---|
| | | | 35 | | | | 40 | | | | | 45 | | | |

| Arg | Val | Thr | Ile | Thr | Arg | Asp | Thr | Ser | Ala | Ser | Thr | Ala | Tyr | Met | Glu |
|---|---|---|---|---|---|---|---|---|---|---|---|---|---|---|---|
| | | 50 | | | | | 55 | | | | | 60 | | | |

| Leu | Ser | Ser | Leu | Arg | Ser | Glu | Asp | Thr | Ala | Val | Tyr | Tyr | Cys |
|---|---|---|---|---|---|---|---|---|---|---|---|---|---|
| 65 | | | | | 70 | | | | | 75 | | | |

(2) INFORMATION FOR SEQ ID NO:62:

(i) SEQUENCE CHARACTERISTICS:
(A) LENGTH: 312 base pairs
(B) TYPE: nucleic acid
(C) STRANDEDNESS: double
(D) TOPOLOGY: linear (i x) FEATURE:
(A) NAME/KEY: CDS
(B) LOCATION: 1..312

(x i) SEQUENCE DESCRIPTION: SEQ ID NO:62:

| CAC | CCT | CAG | CGT | CTG | GAC | CCC | GGG | CAG | AGG | GTC | ACC | ATC | TCT | TGT | TCT | 48 |
|---|---|---|---|---|---|---|---|---|---|---|---|---|---|---|---|---|
| His | Pro | Gln | Arg | Leu | Asp | Pro | Gly | Gln | Arg | Val | Thr | Ile | Ser | Cys | Ser | |
| 1 | | | | 5 | | | | | 10 | | | | | 15 | | |

| GGA | AGC | AGC | TCC | AAC | ATC | GGA | AGA | AGT | ACT | GTA | AGC | TGG | TAC | CAG | CAG | 96 |
|---|---|---|---|---|---|---|---|---|---|---|---|---|---|---|---|---|
| Gly | Ser | Ser | Ser | Asn | Ile | Gly | Arg | Ser | Thr | Val | Ser | Trp | Tyr | Gln | Gln | |
| | | | 20 | | | | | 25 | | | | | 30 | | | |

| CTC | CCA | GGC | ACG | GCC | CCC | AAA | CTC | GTC | ATG | TAT | AGT | CAC | AAT | CAG | CGG | 144 |
|---|---|---|---|---|---|---|---|---|---|---|---|---|---|---|---|---|
| Leu | Pro | Gly | Thr | Ala | Pro | Lys | Leu | Val | Met | Tyr | Ser | His | Asn | Gln | Arg | |
| | | | 35 | | | | | 40 | | | | | 45 | | | |

| TCC | TCA | GGG | GTC | CCT | GAC | CGA | TTC | TCT | GGC | TCC | AAG | TCT | GGC | AAC | TCA | 192 |
|---|---|---|---|---|---|---|---|---|---|---|---|---|---|---|---|---|
| Ser | Ser | Gly | Val | Pro | Asp | Arg | Phe | Ser | Gly | Ser | Lys | Ser | Gly | Asn | Ser | |
| | | 50 | | | | | 55 | | | | | 60 | | | | |

| GCC | TCC | CTG | GAC | ATC | AGT | GGG | CTC | CAG | TCT | GAG | GAT | GAG | GCT | GAT | TAT | 240 |
|---|---|---|---|---|---|---|---|---|---|---|---|---|---|---|---|---|
| Ala | Ser | Leu | Asp | Ile | Ser | Gly | Leu | Gln | Ser | Glu | Asp | Glu | Ala | Asp | Tyr | |
| 65 | | | | | 70 | | | | | 75 | | | | | 80 | |

| TAC | TGT | GCA | GCA | TGG | GAT | GAC | AGC | CTG | AGT | GAA | TTT | CTC | TTC | GGA | ACT | 288 |
|---|---|---|---|---|---|---|---|---|---|---|---|---|---|---|---|---|
| Tyr | Cys | Ala | Ala | Trp | Asp | Asp | Ser | Leu | Ser | Glu | Phe | Leu | Phe | Gly | Thr | |
| | | | | 85 | | | | | 90 | | | | | 95 | | |

| GGG | ACC | AAG | GTC | ACC | GTC | CTA | GGT | | | | | | | | | 312 |
|---|---|---|---|---|---|---|---|---|---|---|---|---|---|---|---|---|
| Gly | Thr | Lys | Val | Thr | Val | Leu | Gly | | | | | | | | | |
| | | | 100 | | | | | | | | | | | | | |

(2) INFORMATION FOR SEQ ID NO:63:

(i) SEQUENCE CHARACTERISTICS:
(A) LENGTH: 104 amino acids
(B) TYPE: amino acid
(D) TOPOLOGY: linear (i i) MOLECULE TYPE: protein (x i) SEQUENCE DESCRIPTION: SEQ ID NO:63:

| His | Pro | Gln | Arg | Leu | Asp | Pro | Gly | Gln | Arg | Val | Thr | Ile | Ser | Cys | Ser |
|---|---|---|---|---|---|---|---|---|---|---|---|---|---|---|---|
| 1 | | | | 5 | | | | | 10 | | | | | 15 | |

| | | | | | | | | | | | | | | |
|---|---|---|---|---|---|---|---|---|---|---|---|---|---|---|
|Gly|Ser|Ser|Ser|Asn|Ile|Gly|Arg|Ser|Thr|Val|Ser|Trp|Tyr|Gln|Gln|
| | | |20| | | |25| | | | |30| | |

| | | | | | | | | | | | | |
|---|---|---|---|---|---|---|---|---|---|---|---|---|
|Leu|Pro|Gly|Thr|Ala|Pro|Lys|Leu|Val|Met|Tyr|Ser|His|Asn|Gln|Arg|
| | |35| | | |40| | | | |45| | | |

| | | | | | | | | | | | | | | |
|---|---|---|---|---|---|---|---|---|---|---|---|---|---|---|
|Ser|Ser|Gly|Val|Pro|Asp|Arg|Phe|Ser|Gly|Ser|Lys|Ser|Gly|Asn|Ser|
| |50| | | | |55| | | | |60| | | |

|Ala|Ser|Leu|Asp|Ile|Ser|Gly|Leu|Gln|Ser|Glu|Asp|Glu|Ala|Asp|Tyr|
|---|---|---|---|---|---|---|---|---|---|---|---|---|---|---|---|
|65| | | | |70| | | | |75| | | | |80|

|Tyr|Cys|Ala|Ala|Trp|Asp|Asp|Ser|Leu|Ser|Glu|Phe|Leu|Phe|Gly|Thr|
|---|---|---|---|---|---|---|---|---|---|---|---|---|---|---|---|
| | | | |85| | | | |90| | | | |95| |

|Gly|Thr|Lys|Val|Thr|Val|Leu|Gly|
|---|---|---|---|---|---|---|---|
| | | |100| | | | |

(2) INFORMATION FOR SEQ ID NO:64:

(i) SEQUENCE CHARACTERISTICS:
        (A) LENGTH: 306 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..306

(xi) SEQUENCE DESCRIPTION: SEQ ID NO:64:

| | | | | | | | | | | | | | | | | |
|---|---|---|---|---|---|---|---|---|---|---|---|---|---|---|---|---|
|TCC|CTG|AGA|CTC|TCC|TGT|GCA|GCC|TCT|GGA|TTC|ACC|TTT|AGC|AGC|TAT|48|
|Ser|Leu|Arg|Leu|Ser|Cys|Ala|Ala|Ser|Gly|Phe|Thr|Phe|Ser|Ser|Tyr| |
|1| | | |5| | | | |10| | | | |15| | |

| | | | | | | | | | | | | | | | | |
|---|---|---|---|---|---|---|---|---|---|---|---|---|---|---|---|---|
|GCC|ATG|AGC|TGG|GTC|CGC|CAG|GCT|CCA|GGG|AAG|GGG|CTG|GAG|TGG|GTC|96|
|Ala|Met|Ser|Trp|Val|Arg|Gln|Ala|Pro|Gly|Lys|Gly|Leu|Glu|Trp|Val| |
| | |20| | | | |25| | | | |30| | | | |

| | | | | | | | | | | | | | | | | |
|---|---|---|---|---|---|---|---|---|---|---|---|---|---|---|---|---|
|TCA|TCC|ATT|AGT|AGT|AGT|AGT|GGT|GAC|ACA|TAC|TAC|GCA|GAC|TCA|GTG|144|
|Ser|Ser|Ile|Ser|Ser|Ser|Ser|Gly|Asp|Thr|Tyr|Tyr|Ala|Asp|Ser|Val| |
| | |35| | | | |40| | | | |45| | | | |

| | | | | | | | | | | | | | | | | |
|---|---|---|---|---|---|---|---|---|---|---|---|---|---|---|---|---|
|AAG|GGC|CGA|TTC|ACC|ATC|TCC|AGA|GAC|AAC|GCC|CAG|AAC|TCA|CTG|TAT|192|
|Lys|Gly|Arg|Phe|Thr|Ile|Ser|Arg|Asp|Asn|Ala|Gln|Asn|Ser|Leu|Tyr| |
| |50| | | | |55| | | | |60| | | | | |

| | | | | | | | | | | | | | | | | |
|---|---|---|---|---|---|---|---|---|---|---|---|---|---|---|---|---|
|CTG|CAA|ATG|AAC|AGC|CTG|AGA|GTC|GAG|GAC|ACG|GCT|GTT|TAT|TAC|TGT|240|
|Leu|Gln|Met|Asn|Ser|Leu|Arg|Val|Glu|Asp|Thr|Ala|Val|Tyr|Tyr|Cys| |
|65| | | | |70| | | | |75| | | | |80| |

| | | | | | | | | | | | | | | | | |
|---|---|---|---|---|---|---|---|---|---|---|---|---|---|---|---|---|
|GCG|AGA|GTC|AGG|GTT|TAC|AGC|AGT|GCC|TGG|GAC|TAC|TGG|GGC|CAG|GGA|288|
|Ala|Arg|Val|Arg|Val|Tyr|Ser|Ser|Ala|Trp|Asp|Tyr|Trp|Gly|Gln|Gly| |
| | | | |85| | | | |90| | | | |95| | |

| | | | | |
|---|---|---|---|---|---|
|ACC|CTG|GTC|ACC|GTC|TCC|306|
|Thr|Leu|Val|Thr|Val|Ser| |
| | | |100| | | |

(2) INFORMATION FOR SEQ ID NO:65:

(i) SEQUENCE CHARACTERISTICS:
        (A) LENGTH: 102 amino acids
        (B) TYPE: amino acid
        (D) TOPOLOGY: linear (ii) MOLECULE TYPE: protein (xi) SEQUENCE DESCRIPTION: SEQ ID NO:65:

|Ser|Leu|Arg|Leu|Ser|Cys|Ala|Ala|Ser|Gly|Phe|Thr|Phe|Ser|Ser|Tyr|
|---|---|---|---|---|---|---|---|---|---|---|---|---|---|---|---|
|1| | | |5| | | | |10| | | | |15| |

|Ala|Met|Ser|Trp|Val|Arg|Gln|Ala|Pro|Gly|Lys|Gly|Leu|Glu|Trp|Val|
|---|---|---|---|---|---|---|---|---|---|---|---|---|---|---|---|
| | |20| | | | |25| | | | |30| | | |

| Ser | Ser | Ile | Ser | Ser | Ser | Ser | Gly | Asp | Thr | Tyr | Tyr | Ala | Asp | Ser | Val |
|---|---|---|---|---|---|---|---|---|---|---|---|---|---|---|---|
|   |   | 35  |     |     |     |     | 40  |     |     |     |     | 45  |     |     |     |

| Lys | Gly | Arg | Phe | Thr | Ile | Ser | Arg | Asp | Asn | Ala | Gln | Asn | Ser | Leu | Tyr |
|---|---|---|---|---|---|---|---|---|---|---|---|---|---|---|---|
|   | 50  |     |     |     |     | 55  |     |     |     |     | 60  |     |     |     |     |

| Leu | Gln | Met | Asn | Ser | Leu | Arg | Val | Glu | Asp | Thr | Ala | Val | Tyr | Tyr | Cys |
|---|---|---|---|---|---|---|---|---|---|---|---|---|---|---|---|
| 65  |     |     |     |     | 70  |     |     |     |     | 75  |     |     |     |     | 80  |

| Ala | Arg | Val | Arg | Val | Tyr | Ser | Ser | Ala | Trp | Asp | Tyr | Trp | Gly | Gln | Gly |
|---|---|---|---|---|---|---|---|---|---|---|---|---|---|---|---|
|   |   |   |   | 85  |     |     |     |     | 90  |     |     |     |     | 95  |     |

| Thr | Leu | Val | Thr | Val | Ser |
|---|---|---|---|---|---|
|   |   |   | 100 |     |     |

( 2 ) INFORMATION FOR SEQ ID NO:66:

( i ) SEQUENCE CHARACTERISTICS:
    ( A ) LENGTH: 201 base pairs
    ( B ) TYPE: nucleic acid
    ( C ) STRANDEDNESS: double
    ( D ) TOPOLOGY: linear ( i x ) FEATURE:
    ( A ) NAME/KEY: CDS
    ( B ) LOCATION: 1..201

( x i ) SEQUENCE DESCRIPTION: SEQ ID NO:66:

| GTA | CTT | GTC | ATC | TAT | GGT | AAA | AAC | AAC | CGG | CCC | TCA | GGG | ATC | CCA | GAC | 48 |
|---|---|---|---|---|---|---|---|---|---|---|---|---|---|---|---|---|
| Val | Leu | Val | Ile | Tyr | Gly | Lys | Asn | Asn | Arg | Pro | Ser | Gly | Ile | Pro | Asp |   |
| 1   |     |     |     | 5   |     |     |     |     | 10  |     |     |     |     | 15  |     |   |

| CGA | TTC | TCT | GGC | TCC | AGC | TCA | GGA | AAC | ACA | GCT | TCC | TTG | ACC | ATC | ACT | 96 |
|---|---|---|---|---|---|---|---|---|---|---|---|---|---|---|---|---|
| Arg | Phe | Ser | Gly | Ser | Ser | Ser | Gly | Asn | Thr | Ala | Ser | Leu | Thr | Ile | Thr |   |
|   |   |   | 20  |     |     |     |     | 25  |     |     |     |     | 30  |     |     |   |

| GGG | GCT | CAG | GCG | GAA | GAT | GAG | GCT | GAC | TAT | TAC | TGT | AAC | TCC | CGG | GAC | 144 |
|---|---|---|---|---|---|---|---|---|---|---|---|---|---|---|---|---|
| Gly | Ala | Gln | Ala | Glu | Asp | Glu | Ala | Asp | Tyr | Tyr | Cys | Asn | Ser | Arg | Asp |   |
|   |   | 35  |     |     |     |     | 40  |     |     |     |     | 45  |     |     |     |   |

| AGC | AGT | GGT | AAC | CAT | AGA | GTT | GTT | ACG | GCC | GGA | GGG | ACC | AAG | CTG | ACC | 192 |
|---|---|---|---|---|---|---|---|---|---|---|---|---|---|---|---|---|
| Ser | Ser | Gly | Asn | His | Arg | Val | Val | Thr | Ala | Gly | Gly | Thr | Lys | Leu | Thr |   |
|   | 50  |     |     |     |     | 55  |     |     |     |     | 60  |     |     |     |     |   |

| GTC | CTA | GGT | 201 |
|---|---|---|---|
| Val | Leu | Gly |   |
| 65  |     |     |   |

( 2 ) INFORMATION FOR SEQ ID NO:67:

( i ) SEQUENCE CHARACTERISTICS:
    ( A ) LENGTH: 67 amino acids
    ( B ) TYPE: amino acid
    ( D ) TOPOLOGY: linear ( i i ) MOLECULE TYPE: protein ( x i ) SEQUENCE DESCRIPTION: SEQ ID NO:67:

| Val | Leu | Val | Ile | Tyr | Gly | Lys | Asn | Asn | Arg | Pro | Ser | Gly | Ile | Pro | Asp |
|---|---|---|---|---|---|---|---|---|---|---|---|---|---|---|---|
| 1   |     |     |     | 5   |     |     |     |     | 10  |     |     |     |     | 15  |     |

| Arg | Phe | Ser | Gly | Ser | Ser | Ser | Gly | Asn | Thr | Ala | Ser | Leu | Thr | Ile | Thr |
|---|---|---|---|---|---|---|---|---|---|---|---|---|---|---|---|
|   |   |   | 20  |     |     |     |     | 25  |     |     |     |     | 30  |     |     |

| Gly | Ala | Gln | Ala | Glu | Asp | Glu | Ala | Asp | Tyr | Tyr | Cys | Asn | Ser | Arg | Asp |
|---|---|---|---|---|---|---|---|---|---|---|---|---|---|---|---|
|   |   | 35  |     |     |     |     | 40  |     |     |     |     | 45  |     |     |     |

| Ser | Ser | Gly | Asn | His | Arg | Val | Val | Thr | Ala | Gly | Gly | Thr | Lys | Leu | Thr |
|---|---|---|---|---|---|---|---|---|---|---|---|---|---|---|---|
|   | 50  |     |     |     |     | 55  |     |     |     |     | 60  |     |     |     |     |

| Val | Leu | Gly |
|---|---|---|
| 65  |     |     |

( 2 ) INFORMATION FOR SEQ ID NO:68:

( i ) SEQUENCE CHARACTERISTICS:
   ( A ) LENGTH: 300 base pairs
   ( B ) TYPE: nucleic acid
   ( C ) STRANDEDNESS: double
   ( D ) TOPOLOGY: linear ( i x ) FEATURE:
   ( A ) NAME/KEY: CDS
   ( B ) LOCATION: 1..300

( x i ) SEQUENCE DESCRIPTION: SEQ ID NO:68:

```
CTC  GAG  ACC  CTG  TCG  CTC  ACC  TGC  GCT  GTC  TCT  GGT  TAC  TCC  ACA  CGG     48
Leu  Glu  Thr  Leu  Ser  Leu  Thr  Cys  Ala  Val  Ser  Gly  Tyr  Ser  Thr  Arg
 1              5                        10                       15

TTA  CTA  CTG  GCC  TGG  GTC  CGG  CAC  CTC  CCA  GGG  AAG  GGG  CTG  GAG  TGG     96
Leu  Leu  Leu  Ala  Trp  Val  Arg  His  Leu  Pro  Gly  Lys  Gly  Leu  Glu  Trp
              20                        25                       30

ATT  GGG  AGT  ATA  CAT  CAT  AGT  GGG  CCC  ACC  TAC  TAC  AAC  CCG  TCC  CTC    144
Ile  Gly  Ser  Ile  His  His  Ser  Gly  Pro  Thr  Tyr  Tyr  Asn  Pro  Ser  Leu
              35                        40                       45

AAG  AGT  CGA  GTC  ACC  ATG  TCA  CCT  GAC  ACG  TCC  AGG  AAC  CAG  TTC  TCC    192
Lys  Ser  Arg  Val  Thr  Met  Ser  Pro  Asp  Thr  Ser  Arg  Asn  Gln  Phe  Ser
 50                                 55                       60

CTG  AAG  ATG  ACC  TCT  GTG  ACC  GCC  GCG  GAC  ACG  GCC  ATG  TAT  TAC  TGT    240
Leu  Lys  Met  Thr  Ser  Val  Thr  Ala  Ala  Asp  Thr  Ala  Met  Tyr  Tyr  Cys
 65                       70                       75                       80

GCG  AGG  GAC  CGA  TAT  GGT  TAC  TTT  GAC  TCC  TGG  GGC  CAG  GGA  ACC  CTG    288
Ala  Arg  Asp  Arg  Tyr  Gly  Tyr  Phe  Asp  Ser  Trp  Gly  Gln  Gly  Thr  Leu
                        85                       90                       95

GCC  ACC  GTC  TCN                                                                 300
Ala  Thr  Val  Ser
              100
```

( 2 ) INFORMATION FOR SEQ ID NO:69:

( i ) SEQUENCE CHARACTERISTICS:
      ( A ) LENGTH: 100 amino acids
      ( B ) TYPE: amino acid
      ( D ) TOPOLOGY: linear ( i i ) MOLECULE TYPE: protein ( x i ) SEQUENCE DESCRIPTION: SEQ ID NO:69:

```
Leu  Glu  Thr  Leu  Ser  Leu  Thr  Cys  Ala  Val  Ser  Gly  Tyr  Ser  Thr  Arg
 1              5                        10                       15

Leu  Leu  Leu  Ala  Trp  Val  Arg  His  Leu  Pro  Gly  Lys  Gly  Leu  Glu  Trp
              20                        25                       30

Ile  Gly  Ser  Ile  His  His  Ser  Gly  Pro  Thr  Tyr  Tyr  Asn  Pro  Ser  Leu
              35                        40                       45

Lys  Ser  Arg  Val  Thr  Met  Ser  Pro  Asp  Thr  Ser  Arg  Asn  Gln  Phe  Ser
 50                       55                       60

Leu  Lys  Met  Thr  Ser  Val  Thr  Ala  Ala  Asp  Thr  Ala  Met  Tyr  Tyr  Cys
 65                       70                       75                       80

Ala  Arg  Asp  Arg  Tyr  Gly  Tyr  Phe  Asp  Ser  Trp  Gly  Gln  Gly  Thr  Leu
                        85                       90                       95

Ala  Thr  Val  Ser
              100
```

( 2 ) INFORMATION FOR SEQ ID NO:70:

( i ) SEQUENCE CHARACTERISTICS:
      ( A ) LENGTH: 309 base pairs
      ( B ) TYPE: nucleic acid
      ( C ) STRANDEDNESS: double ( D ) TOPOLOGY: linear ( i x ) FEATURE:
    ( A ) NAME/KEY: CDS
    ( B ) LOCATION: 1..309

( x i ) SEQUENCE DESCRIPTION: SEQ ID NO:70:

| CCT | GCT | TGG | TTG | CTT | GTG | GCC | TTG | GGA | CAG | ACA | GTC | AGG | ATC | ACA | TGC | 48 |
|---|---|---|---|---|---|---|---|---|---|---|---|---|---|---|---|---|
| Pro | Ala | Trp | Leu | Leu | Val | Ala | Leu | Gly | Gln | Thr | Val | Arg | Ile | Thr | Cys | |
| 1 | | | | 5 | | | | | 10 | | | | | 15 | | |

| CAA | GGA | GAC | AGC | CTC | AGA | AGT | TAT | TAT | GCA | AGT | TGG | TAT | CAG | CAG | AAG | 96 |
|---|---|---|---|---|---|---|---|---|---|---|---|---|---|---|---|---|
| Gln | Gly | Asp | Ser | Leu | Arg | Ser | Tyr | Tyr | Ala | Ser | Trp | Tyr | Gln | Gln | Lys | |
| | | | 20 | | | | | 25 | | | | | 30 | | | |

| CCA | GGA | CAG | GCC | CCT | GTA | CTT | GTC | ATC | TCT | GGT | AAA | AAC | AAC | CGG | CCC | 144 |
|---|---|---|---|---|---|---|---|---|---|---|---|---|---|---|---|---|
| Pro | Gly | Gln | Ala | Pro | Val | Leu | Val | Ile | Ser | Gly | Lys | Asn | Asn | Arg | Pro | |
| | | 35 | | | | | 40 | | | | | 45 | | | | |

| TCA | GGG | ATC | CCA | GAC | CGA | TTC | TCT | GCC | TCC | AGC | TCA | GGA | AAC | ACA | GCT | 192 |
|---|---|---|---|---|---|---|---|---|---|---|---|---|---|---|---|---|
| Ser | Gly | Ile | Pro | Asp | Arg | Phe | Ser | Ala | Ser | Ser | Ser | Gly | Asn | Thr | Ala | |
| | 50 | | | | | 55 | | | | | 60 | | | | | |

| TCC | TTG | ACC | ATC | ACT | GGG | GCT | CAG | GCG | GAA | GAT | GAG | GCT | GAC | TAT | TAC | 240 |
|---|---|---|---|---|---|---|---|---|---|---|---|---|---|---|---|---|
| Ser | Leu | Thr | Ile | Thr | Gly | Ala | Gln | Ala | Glu | Asp | Glu | Ala | Asp | Tyr | Tyr | |
| 65 | | | | | 70 | | | | | 75 | | | | | 80 | |

| TGT | CTC | TCT | CGG | GAC | AGC | GGA | AGT | AAC | CAA | CTG | GTA | TTC | GGC | GGA | GGG | 288 |
|---|---|---|---|---|---|---|---|---|---|---|---|---|---|---|---|---|
| Cys | Leu | Ser | Arg | Asp | Ser | Gly | Ser | Asn | Gln | Leu | Val | Phe | Gly | Gly | Gly | |
| | | | | 85 | | | | | 90 | | | | | 95 | | |

| ACC | AAG | CTG | ACC | GTC | CTA | GGT | | | | | | | | | | 309 |
|---|---|---|---|---|---|---|---|---|---|---|---|---|---|---|---|---|
| Thr | Lys | Leu | Thr | Val | Leu | Gly | | | | | | | | | | |
| | | | 100 | | | | | | | | | | | | | |

( 2 ) INFORMATION FOR SEQ ID NO:71:

( i ) SEQUENCE CHARACTERISTICS:
        ( A ) LENGTH: 103 amino acids
        ( B ) TYPE: amino acid
        ( D ) TOPOLOGY: linear ( i i ) MOLECULE TYPE: protein ( x i ) SEQUENCE DESCRIPTION: SEQ ID NO:71:

| Pro | Ala | Trp | Leu | Leu | Val | Ala | Leu | Gly | Gln | Thr | Val | Arg | Ile | Thr | Cys |
|---|---|---|---|---|---|---|---|---|---|---|---|---|---|---|---|
| 1 | | | | 5 | | | | | 10 | | | | | 15 | |

| Gln | Gly | Asp | Ser | Leu | Arg | Ser | Tyr | Tyr | Ala | Ser | Trp | Tyr | Gln | Gln | Lys |
|---|---|---|---|---|---|---|---|---|---|---|---|---|---|---|---|
| | | | 20 | | | | | 25 | | | | | 30 | | |

| Pro | Gly | Gln | Ala | Pro | Val | Leu | Val | Ile | Ser | Gly | Lys | Asn | Asn | Arg | Pro |
|---|---|---|---|---|---|---|---|---|---|---|---|---|---|---|---|
| | | 35 | | | | | 40 | | | | | 45 | | | |

| Ser | Gly | Ile | Pro | Asp | Arg | Phe | Ser | Ala | Ser | Ser | Ser | Gly | Asn | Thr | Ala |
|---|---|---|---|---|---|---|---|---|---|---|---|---|---|---|---|
| | 50 | | | | | 55 | | | | | 60 | | | | |

| Ser | Leu | Thr | Ile | Thr | Gly | Ala | Gln | Ala | Glu | Asp | Glu | Ala | Asp | Tyr | Tyr |
|---|---|---|---|---|---|---|---|---|---|---|---|---|---|---|---|
| 65 | | | | | 70 | | | | | 75 | | | | | 80 |

| Cys | Leu | Ser | Arg | Asp | Ser | Gly | Ser | Asn | Gln | Leu | Val | Phe | Gly | Gly | Gly |
|---|---|---|---|---|---|---|---|---|---|---|---|---|---|---|---|
| | | | | 85 | | | | | 90 | | | | | 95 | |

| Thr | Lys | Leu | Thr | Val | Leu | Gly |
|---|---|---|---|---|---|---|
| | | | 100 | | | |

ISOLATION AND PRODUCTION OF CATALYTIC ANTIBODIES USING PHAGE TECHNOLOGY

REFERENCE TO RELATED APPLICATIONS

This application is continuation of Ser. No. 08/007,684, filed Jan. 22, 1993, now abandoned, which is a continuation-in-part of International Application WO 92/01047 (PCT/GB91/01134) having an International filing date of Jul. 10, 1991, a publication date of Jan. 23, 1992, and wherein the U.S. is a designated State, said International Application WO 92/01047 (PCT/GB91/01134) being hereby incorporated by reference.

FIELD OF THE INVENTION

The present invention relates to the isolation and production of catalytic antibodies displayed on bacteriophage and, more particularly, the isolation and production of human catalytic antibodies. This invention also relates to the isolation and production of catalytic antibodies for use in prodrug activation. This invention further relates to production of catalytic antibodies that bind to transitional state analogs.

BACKGROUND OF THE INVENTION

Monoclonal antibodies are traditionally made by establishing an immortal mammalian cell line which is derived from a single immunoglobulin producing cell secreting one form of a biologically functional antibody molecule with a particular specificity. Because the antibody-secreting mammalian cell line is immortal, the characteristics of the antibody are reproducible from batch to batch. The key proprieties of monoclonal antibodies are their specificity for a particular antigen and the reproducibility with which they can be manufactured.

Structurally, the simplest antibody (IgG) comprises four polypeptide chains, two heavy (H) chains and two light (L) chains connected by disulfide bonds. The light chains exist in two distinct forms called K (kappa) and λ (lambda). Each chain has a constant region (C) and a variable region (V). Each chain is organized into a series of domains. The light chains have two domains, corresponding to the C region and the other to the V Region. The heavy chains have four domains, one corresponding to the V region and three domains (1, 2, and 3) in the C region. The antibody has two arms (each arm being a Fab region), each of which has a VL and a VH region associated with each other. It is this pair of V regions (VL and VH) that differ from one antibody to another (owing to amino acid sequence variations), and which together are responsible for recognizing the antigen and providing an antigen binding site (ABS). In even more detail, each V region is made up from three complementarily determining regions (CDR) separated by four framework regions (FR). The CDRs are the most variable part of the variable regions, and they perform the critical antigen binding function. The CDR regions are derived from many potential germ line sequences via a complex process involving recombination, mutation, and selection.

It has been shown that the function of binding antigens can be performed by fragments of a whole antibody. Example binding fragments are (i) the Fab fragment consisting of the VL, VH, CL and CH1 domains; (ii) the Fd fragment consisting of the VH and CH1 domains; (iii) the Fv fragment consisting of the VL and VH domains of a single arm of an antibody; (iv) the dAb fragment (Ward et al., *Nature* 341 (1989): 544–546) which consists of a VH domain; (v) isolated CDR regions; and (vi) F(ab')$_2$ fragments, a bivalent fragment comprising two Fab fragments linked by a disulfide bridge at the hinge region.

Although the two domains of the Fv fragment are coded for by separate genes, it has proved possible to make a synthetic linker that enables them to be made as a single protein chain (known as single chain Fv (scFv); Bird et al., *Science* 242 (1988):423–426; Huston et al., *Proc. Natl. Acad. Sci.*, USA 85 (1988):5879–5883); by recombinant methods. These scFv fragments were assembled from genes from monoclonals that had been previously isolated. In our earlier application, WO 92/01047, we described a process to assemble scFv fragments from VH and VL domains that were not part of a previously isolated antibody.

Although monoclonal antibodies, their fragments and derivatives have been enormously advantageous, there are nevertheless a number of limitations associated with them. First, the therapeutic applications of monoclonal antibodies produced by human immortal cell lines holds great promise for the treatment of a wide range of diseases (Lennox, *Clinical Applications of Monoclonal Antibodies,* British Medical Bulletin 1984). Unfortunately, immortal antibody-producing human cell lines are very difficult to establish and they give low yields of antibody (approximately 1 μg/ml). In contrast, equivalent rodent cell lines yield high amounts of antibody (approximately 100 μg/ml). However, the repeated administration of these foreign rodent proteins to humans can lead to harmful hypersensitivity reactions. As a result, these rodent-derived monoclonal antibodies have limited therapeutic use.

Second, a key aspect in the isolation of monoclonal antibodies is how many different clones of antibody producing cells with different specificities, can be practically established and sampled compared to how many theoretically need to be sampled in order to isolate a cell producing antibody with the desired specificity characteristics (Milstein, Royal Soc. Croonian Lecture, *Proc. R. Soc. London B.* 239 (1990):1–16). For example, the number of different specificities expressed at any one time by lymphocytes of the murine immune system is thought to be approximately $10^7$ and this is only a small proportion of the potential repertoire of specificities. However, during the isolation of a typical antibody producing cell with a desired specificity, the investigator is only able to sample $10^3$ to $10^4$ individual specificities. The problem is worse in the human, where one has approximately $10^{12}$ lymphocyte specificities with the limitation on sampling of $10^3$ or $10^4$ remaining.

This problem has been alleviated to some extent in laboratory animals by the use of immunization regimes. Thus, where one wants to produce monoclonal antibodies having a specificity against a particular epitope, an animal is immunized with an immunogen expressing that epitope. The animal will then mount an immune response against the immunogen and there will be a proliferation of lymphocytes which have specificity against the epitope. Owing to this proliferation of lymphocytes with the desired specificity, it becomes easier to detect them in the sampling procedure. However, this approach is not successful in all cases as a suitable immunogen may not be available. Furthermore, where one wants to produce human monoclonal antibodies (e.g., for therapeutic administration), such an approach is not practically or ethically feasible.

In our earlier application, WO 92/01047, we described methods of constructing a bacteriophage that expresses and displays at its surface a large biologically functional binding molecule (e.g., antibody fragments, enzymes, and receptors) and which remains intact and infectious. We called the structure which comprises a virus particle and a binding molecule displayed at the viral surface a "package". Where the binding molecule is an antibody, an antibody derivative or fragment, or a domain that is homologous to an immunoglobulin domain, we called the package a "phage antibody" (pAb). However, except where the context demanded otherwise, where the term phage antibody is used generally, it was also interpreted as referring to any package comprising a virus particle and a biologically functional binding molecule displayed at the viral surface. Since the original filing of WO 92/01047, a number of examples of functional antibody and other protein domains expressed on the surface of bacteriophage have been reported in both the literature and additional patent applications.

This simple substitution of immortalized cells with bacterial cells as the "factory", considerably simplifies procedures for preparing large amounts of binding molecules expressed on the surface of the bacteriophage. Furthermore, the use of polymerase chain reaction (PCR) amplification (Saiki et al., *Science* 239 (1988):487–491) to isolate antibody producing sequences from cells (e.g., hybridomas and B cells) has great potential for speeding up the timescale under which binding specificities can be isolated. Phage antibody expression libraries can be easily generated by cloning the amplified VH and VL genes directly into bacteriophage expression vectors. Furthermore, a bacteriophage based recombinant production system allows scope for producing tailor-made antibodies and fragments thereof. For example, it is possible to produce chimeric molecules with new combinations of binding and effector functions, humanized antibodies (e.g., murine variable regions combined with human constant domains or murine-antibody CDRs grafted onto a human FR) and novel antigen-binding molecules. The key advantage of the phage based system being the ability to directly screen the recombinant antibodies directly for the desired binding specificities.

In creating recombinant VH and VL phage libraries several problems need to be addressed. For example, in a mouse there are approximately $10^7$ possible H chains and $10^7$ possible L chains. Therefore, there are $10^{14}$ possible combinations of H and L chains, and to test for anything like this number of combinations, one would have to create and screen a library of about $10^{14}$ clones. This had not previously been a practical possibility. PCT/GB92/00883 and PCT/GB92/01755 applications, which are herein incorporated by reference, disclose a number of approaches which ameliorate this problem. Each of these applications is a continuation-in-part of our International Application WO 92/01047.

In addition, a number of molecular biological techniques which have previously been developed for engineering of antibody active sites can be applied in combination with the phage antibody library approaches described previously. These techniques include site-directed mutagenesis of residues within a CDR, replacement of all or portions of CDR (s) with random amino acid sequence, CDR shuffling in which a CDR region is essentially replaced with a library of CDR regions. The use of pAbs may also allow the construction of entirely synthetic antibodies. Furthermore, antibodies may be made which have some synthetic sequences, for example, CDRs, and some naturally derived sequences (see for example PCT/BG92/06372). For example, V-gene repertoires could be made in vitro by combining un-rearranged V genes, with D and J segments. Libraries of pAbs could then be selected by binding to antigen, hypermutated in vitro in the antigen-binding loops or V domain framework regions, and subjected to further rounds of selection and mutagenesis.

pAbs have a range of applications in selecting antibody genes encoding antigen binding activities. One particularly exciting area of application is in the development of antibodies with catalytic properties (catalytic antibodies). Catalytic antibodies have been described in U.S. Pat. Nos. 4,888,281 to Schochetman et al.; 4,963,355 to Kim et al.; and 5,037,750 to Schochetman et al., all hereby incorporated by reference. As disclosed therein, catalytic antibodies combine the catalytic abilities of enzymes with the binding capabilities of antibodies.

All catalytic antibodies described to date have been generated using monoclonal antibody technology. The details of that process are well known to those of ordinary skill in the art. A typical methodology first involves immunizing mice with an appropriate antigen. The antigen may be the desired reactant; the desired reactant bound to a peptide or other carrier molecule; a reaction intermediate or an analog of the reactant; or the product or a reaction intermediate.

"Analog" as the term is used here can encompass isomers, homologs, transition state analogs or other compounds sufficiently resembling the reactant in terms of chemical structure such that an antibody raised against the analog may participate in an immunological reaction with the reactant but will not necessarily catalyze a reaction of the analog.

Although a number of different types of antibody catalysts have been developed with this technology, the time required to establish and then screen the hybridomas for the desired specificity is of considerable importance.

If the desired specificity is sufficiently rare, it may be impractical or impossible to sample enough hybridomas cell lines to recover the desired specificity.

Additionally, there is currently no suitable hybridoma based technology for generating entirely human catalytic antibodies.

The methods of the invention can also be used to effect a cleavage that leads to the activation of some biological function.

Such reactions include the cleavage of peptide bonds, but may also include ester bonds or glycosidic bonds or other types of bonds.

One example of the cleavage of a biomolecule which leads to the activation of a biological function is the treatment of insulin-dependent diabetes. Patients self-administer insulin by injection. Prior attempts to develop a formulation of insulin whose release into the circulation mimics the pharmacokinetics of the release of natural pancreatic insulin have not proved successful. Insulin exists in the pancreas in a pro-form, proinsulin, whose activity is many orders of magnitude lower than insulin itself. An antibody protease specific for the peptide bond that leads to conversion of proinsulin to insulin can be designed so that its kinetic characteristics allow release of insulin in vivo after an injection of proinsulin plus antibody protease. This is an example of prodrug activation where the drug in this instance is a natural protein hormone. Prodrugs may include many therapeutically active molecules which lead to the activation or deactivation of a biological function. The pro-form may either take advantage of a natural modification of the drug or any suitable synthetic modification thereof. Suitable drug derivatives with low activity (therapeutically beneficial or toxic), which, on modification with a suitable catalytic antibody, are converted to an active form. A particular example of this process is given in PCT/US89/01951 filed May 4, 1989, which is hereby incorporated by reference.

SUMMARY OF THE INVENTION

One object of the present invention is to provide a method for producing and isolating a catalytic antibody displayed on phage which is capable of catalytically increasing the rate of a chemical reaction.

Another object of the present invention is to produce human catalytic antibodies by one of several different methods outlined hereafter.

A further object of the present invention is to isolate phage displaying antibody epitopes that bind to transition state analogs, phosphonates, and RT3.

Still another object of the present invention is to produce a catalytic antibody from antibodies (either mouse or human-derived) that bind transition state analogs, phosphonates, and RT3 by one of several different methods including mutagenesis, chain shuffling, and CDR shuffling or various combinations of these procedures.

And finally, yet another object of the present invention is to produce catalytic antibodies for use in prodrug activation.

Accordingly, the present invention provides a method for producing catalytic antibodies displayed on phage comprising the steps of:

(a) generating a gene library of antibody-derived domains;
(b) inserting coding for said domains into a phage expression vector; and
(c) isolating said catalytic antibodies.

The invention further provides a method for isolating catalytic antibodies displayed on phage comprising the following steps:

(a) preparing an antigen;
(b) immunizing with said antigen;
(c) generating a library of VH and VL domains from said immunized animal;
(d) cloning said VH and VL domains into a phage expression vector to generate phage display antibodies;
(e) selecting phage display antibodies which bind specifically to said antigen;
(f) screening said selected phage display antibodies for catalytic activity to substrate; and
(g) isolating said catalytic antibodies.

The invention further provides a method for isolating catalytic human antibodies displayed on phage comprising the following steps:

(a) preparing an antigen;
(b) generating a library of VH and VL domains;
(c) cloning said VH and VL domains into a phage expression vector to generate phage display antibodies;
(d) selecting phage display antibodies which bind specifically to said antigen;
(e) screening said selected phage display antibodies for catalytic activity to substrate; and
(f) isolating said catalytic antibodies.

The invention further provides a method for producing catalytic antibodies displayed on phage through chain shuffling comprising the following steps:

(a) combining a library of VL genes with VH genes to form a chain shuffled library;
(b) cloning the shuffled chain;
(c) expressing said catalytic antibody on phage;
(d) selecting against an antigen; and
(e) screening for catalytic activity.

The invention further provides a method for producing catalytic antibodies displayed on phage through CDR shuffling comprising the following steps:

(a) isolating VL and VH genes;
(b) isolating a library of CDR regions;
(c) recombining said VL and VH genes with said library of CDR regions to produce a CDR shuffled library; and
(d) cloning the CDR shuffled library;
(e) expressing said CDR shuffled library on phage;
(f) selecting against an antigen; and
(g) screening for catalytic activity.

The invention further provides a method for producing catalytic antibodies displayed on phage through imprinting comprising the following steps:

(a) selecting a set of antibodies;
(b) isolating a set of VH and a set of VL genes from said antibodies;
(c) combining said set of VH with a library of VL and combining said set of VL with a library of VH to form two combination libraries;
(d) cloning said combination libraries;
(e) expressing said libraries on phage;
(f) selecting against an antigen;
(g) isolating selected libraries of VH and VL genes;
(h) combining said libraries of VH and VL genes;
(i) cloning said combined libraries;
(j) expressing said combined libraries on phage;
(k) reselecting against an antigen; and
(l) screening for catalytic activity.

The invention further provides a method for enhancing the rate of cleavage or formation of a specific bond within a molecule in vivo which comprises introducing into an animal an effective amount of a phage-derived catalytic antibody.

The invention further provides a method for in vivo activation of a prodrug comprising:

(a) introducing a prodrug into a patient, said prodrug having a chemical bond therein which upon cleavage releases the active form of said drug; and
(b) introducing into said patient an effective amount of a phage-derived catalytic antibody capable of cleaving said bond in said prodrug.

BRIEF DESCRIPTION OF THE DRAWINGS

The present invention as defined in the claims can be better understood with reference to the text and to the drawings.

FIGS. 1A, 1B, 2, 3, and 4 show the reaction schemes for the synthesis of Compounds 7 (RT3 hapten), 8, 12, and 15, respectively, and intermediates thereof.

FIGS. 5A and 5B shows the plasmid construct resulting from the insertion of His-6 oligo into pHEN-OX16 to give pHEN-OX16his11.

(a) total periplasmic proteins from 1 ml of cells.
(b) unbound fraction from 1 ml of cells, after addition of binding matrix.

(c) fraction bound and eluted from matrix, equivalent to 1 ml of cells.

(d–f) are purified fractions equivalent to 5 mils of cells.

(d) pOX16-his-11 antibody fragment eluted with PBS+ 1M Nac1, 250 mM imidazole.

(e) pOX16-his-11 antibody fragment eluted with PBS, 250 mM imidazole.

(f) pSCFv4his-6 antibody fragment eluted with PBS+1M NaC1, 250 mM imidazole.

Figure 7B:
Figure 9C:
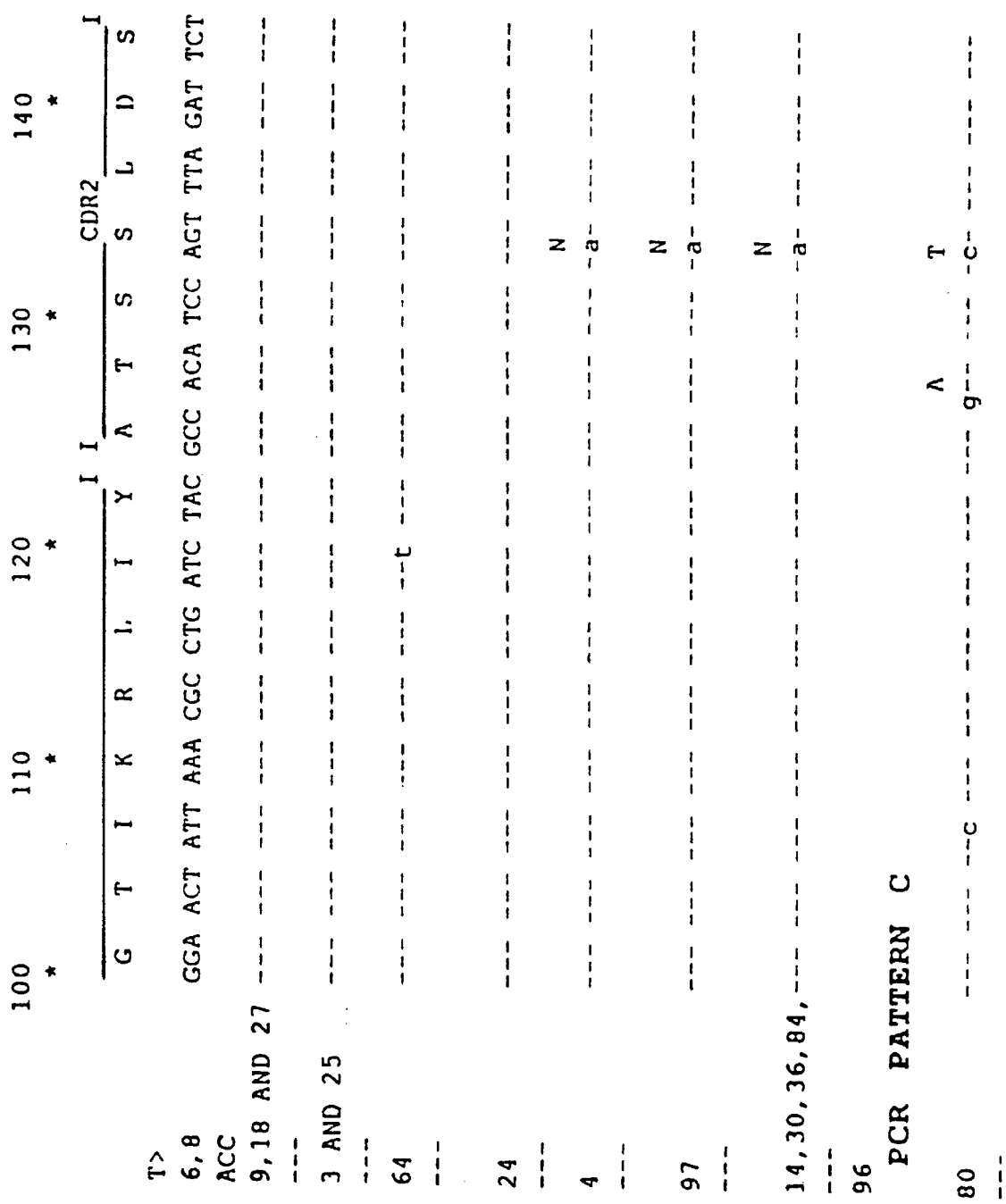
Figure 10C:
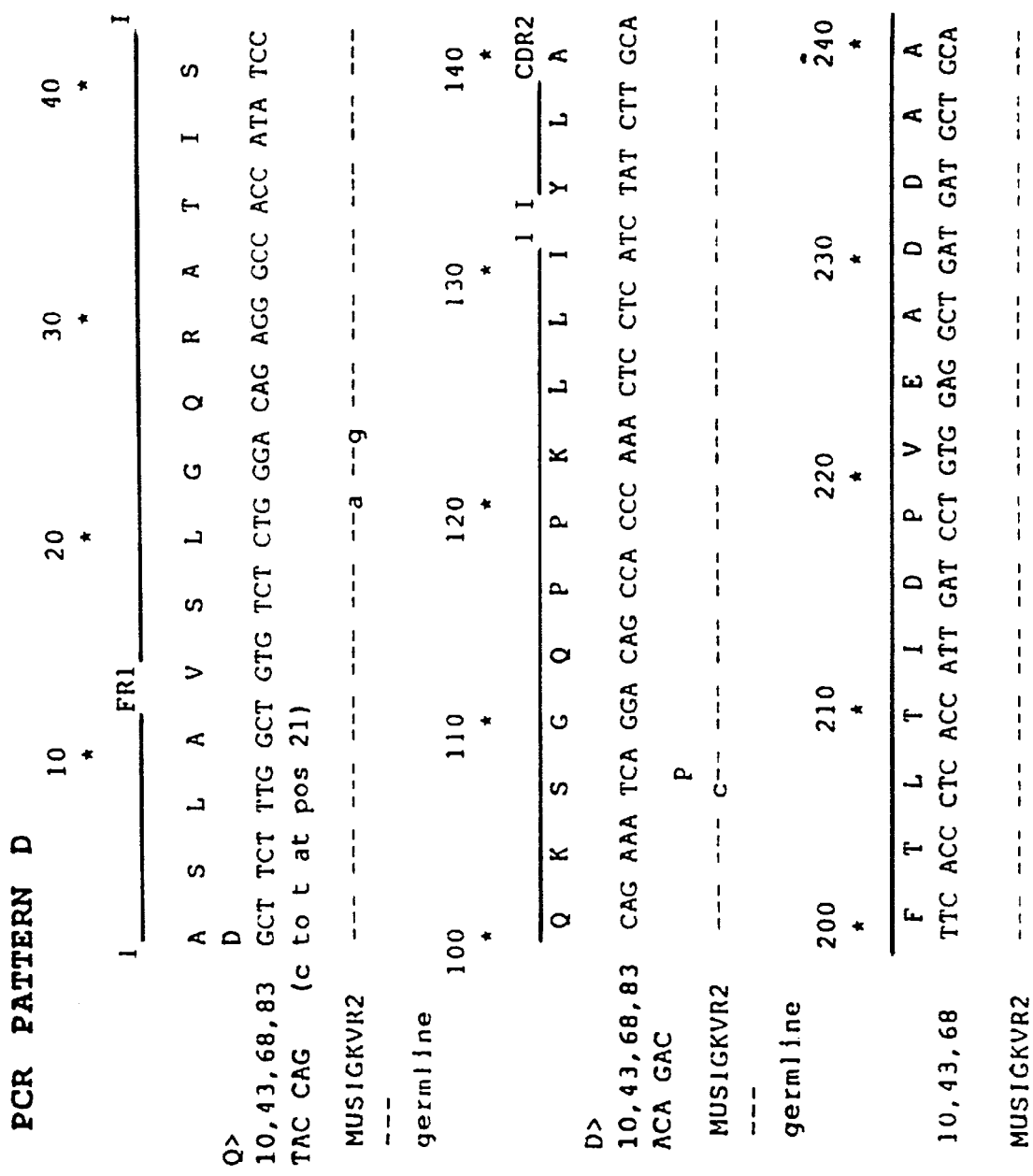

FIGS. 7A, 7B and 7C shows pCANTAB vectors encoding C terminal his-6 peptides.

FIG. 8 shows the competitive assay results for selected mouse RT3 phage antibodies with haptens (RT3) portions of the haptens (RT3A and RT3B) or portions of the product (Prod A and Prod B).

FIGS. 9A through 9F shows the genetic sequence of light chain pattern A and light chain pattern C from mouse-derived RT3 phage antibodies.

FIG. 10A through 10F shows the alignment of the mouse germline to the genetic sequence of light chain patterns B, D, and I from mouse-derived RT3 phage antibodies.

Figure 11D:
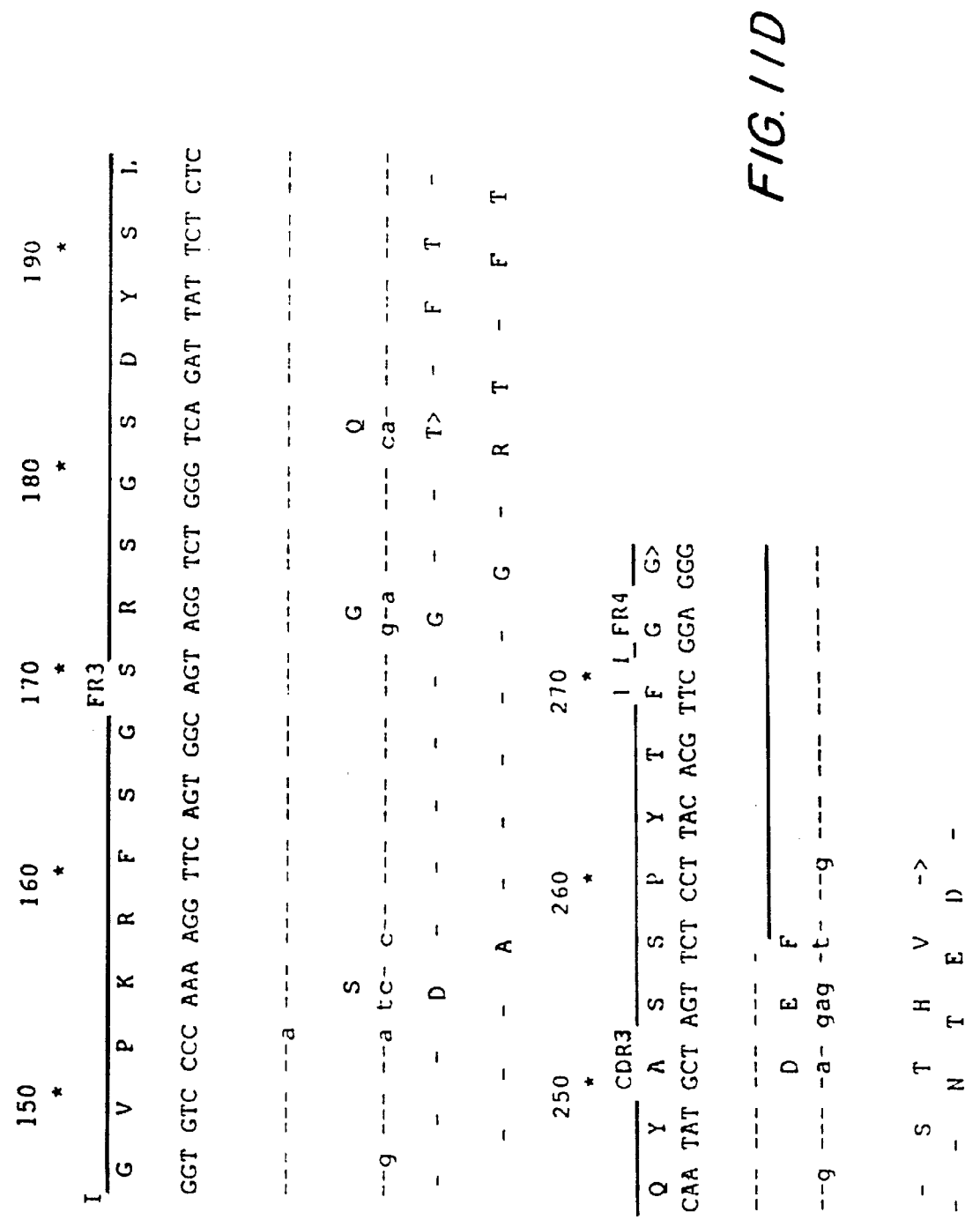

FIGS. 11A through 11D shows the comparison of genetic sequences of light chain patterns A, B, C, D, and I from mouse-derived RT3 phage antibodies.

FIGS. 12A through 12J shows the genetic sequence of heavy chain pattern A from mouse-derived RT3 phage antibodies.

FIGS. 13A through 13F shows the alignment of the mouse germline to the genetic sequence of heavy chain patterns B and D from mouse-derived RT3 phage antibodies.

FIGS. 14A through 14F shows the comparison of genetic sequences of heavy chain patterns A, B, C, D, and I from mouse-derived RT3 phage antibodies.

Figure 15A:
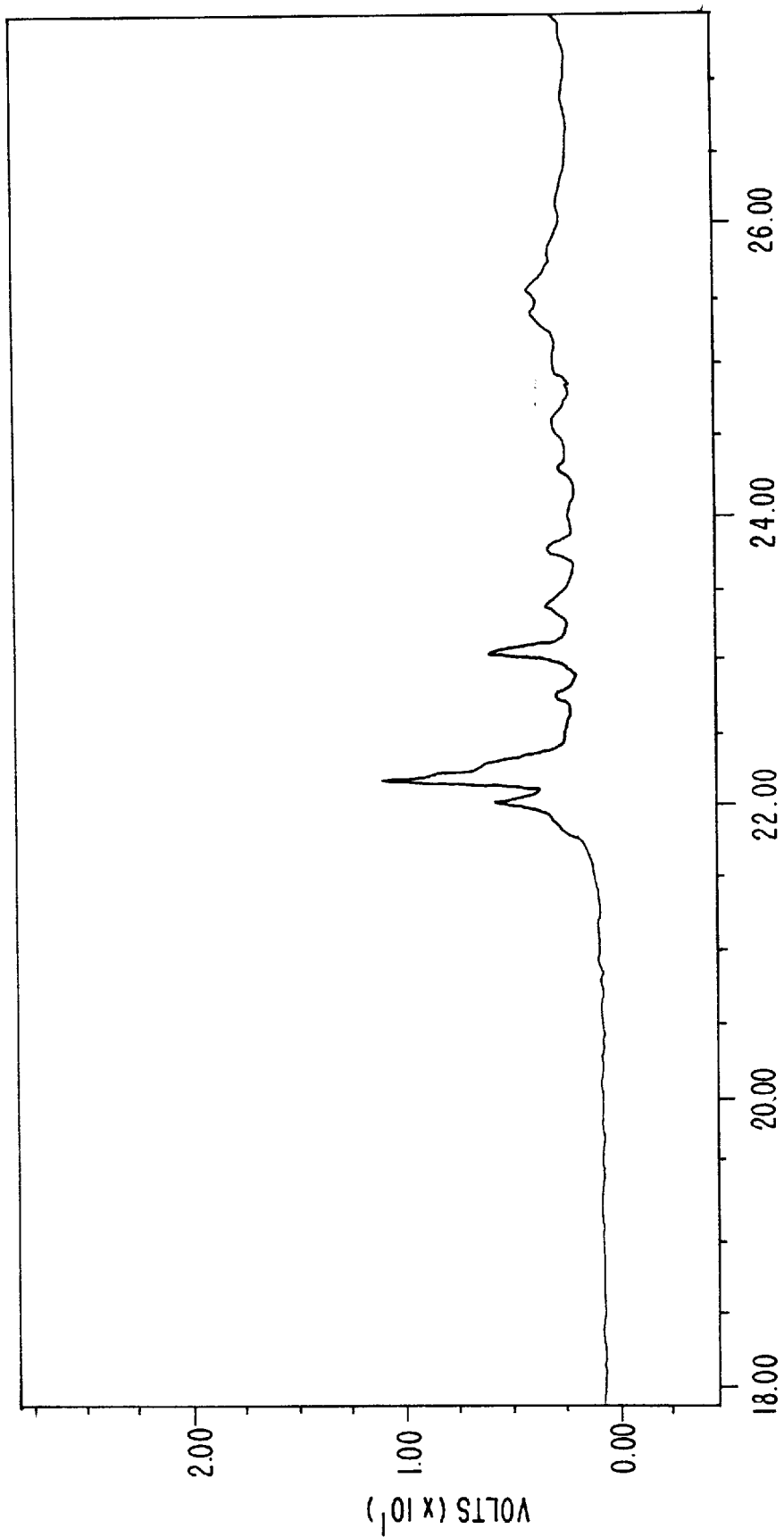

FIG. 15A shows an HPLC chromatogram of a catalytic assay of IMAC pure scFv from clone 18.

Figure 15B:
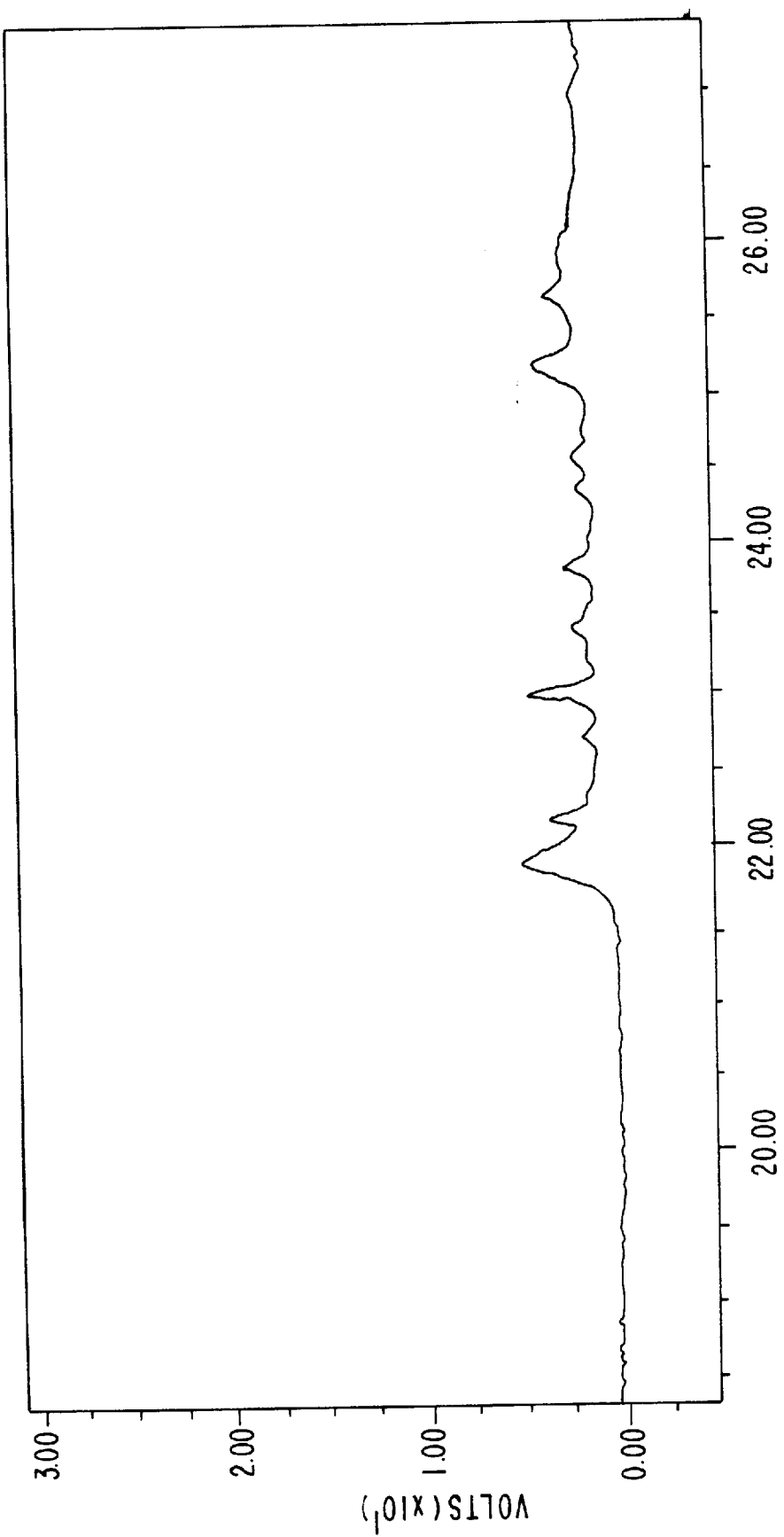

FIG. 15B shows an HPLC chromatogram of a catalytic assay +RT3 hapten of IMAC pure scFv from clone 18

Figure 15C:
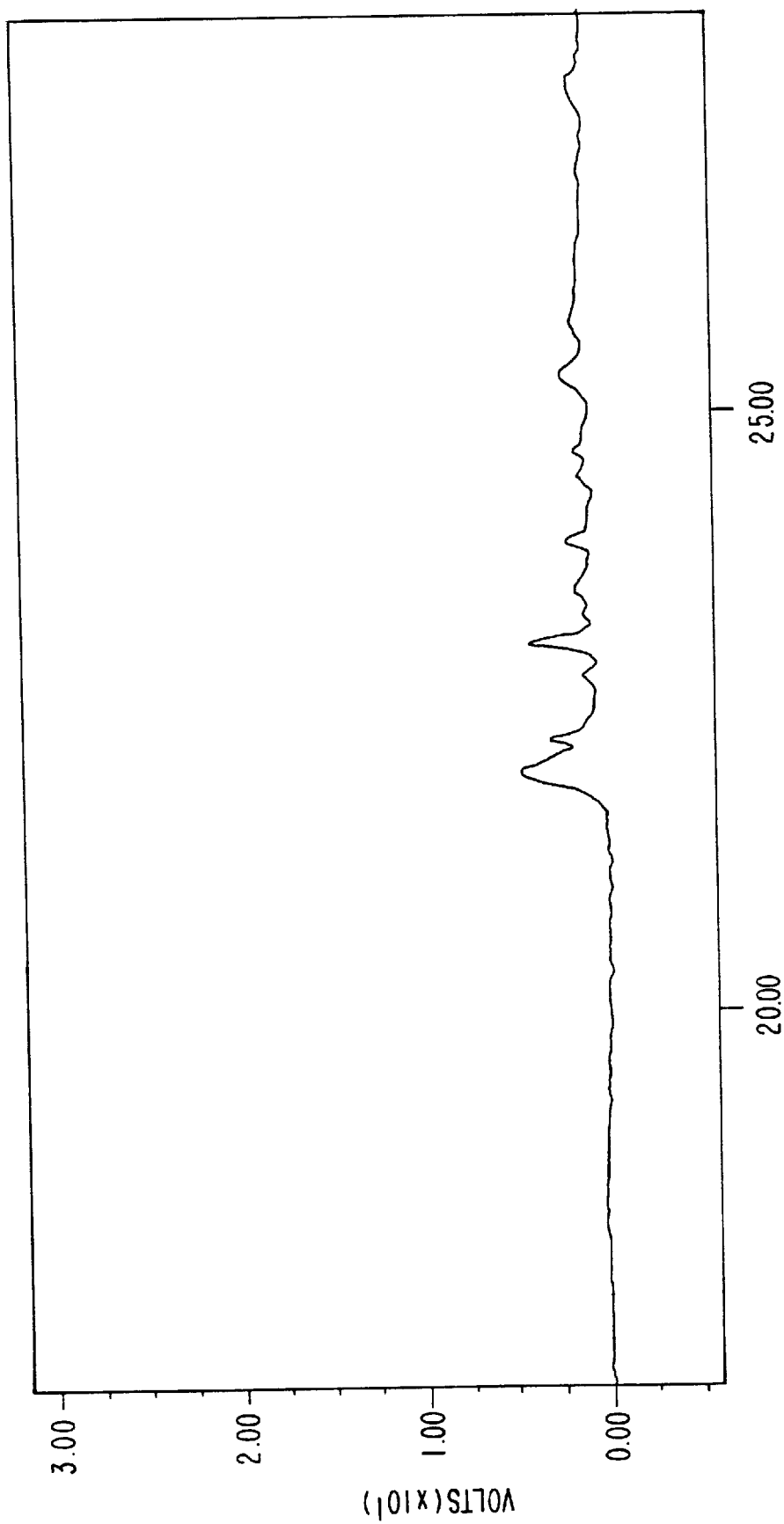

FIG. 15C shows an HPLC chromatogram of a catalytic RT3 assay blank at pH 9.0

Figure 16:
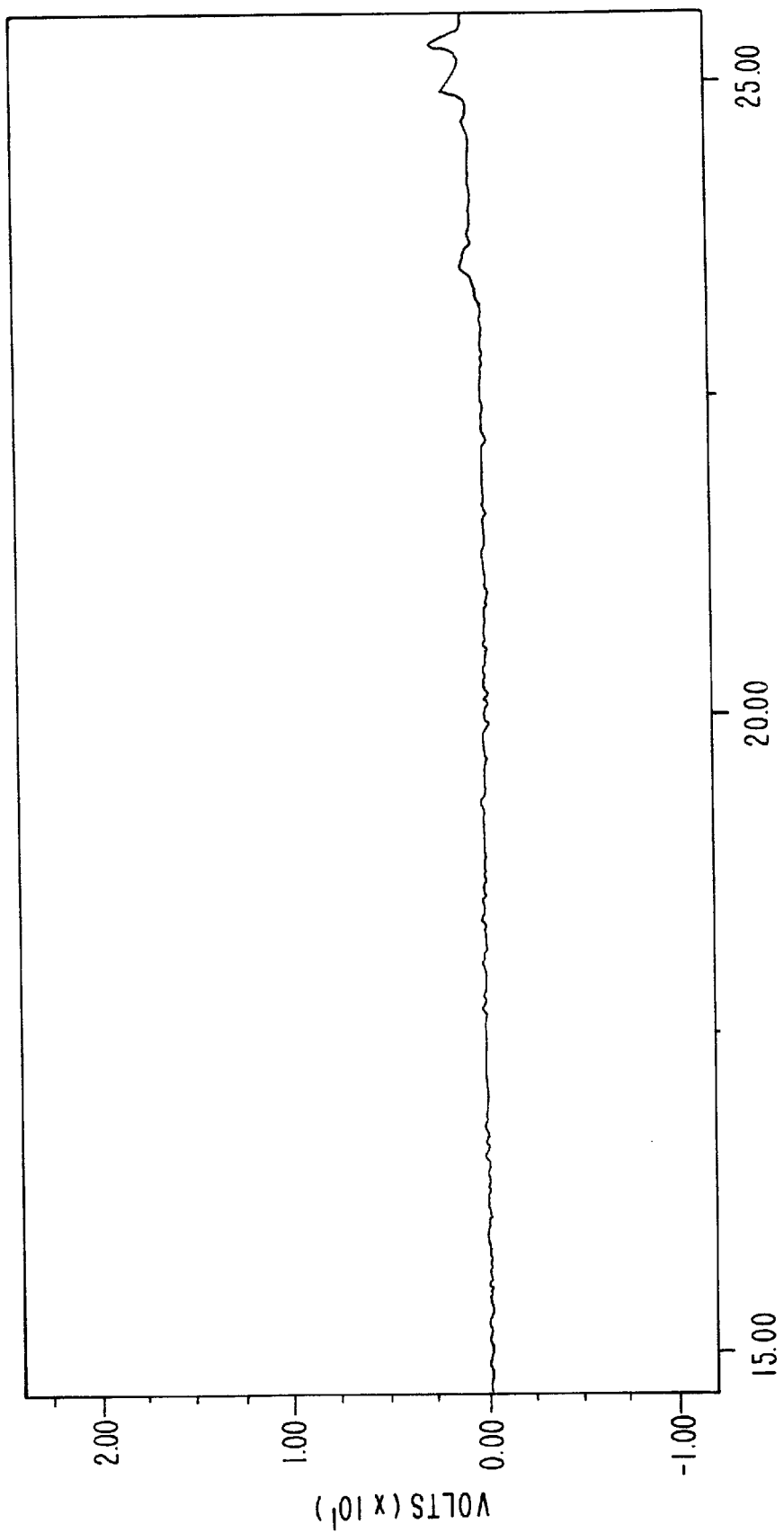

FIG. 16 shows an HPLC chromatogram of a catalytic assay of HIC pure scFv from clone 18.

Figure 17A:
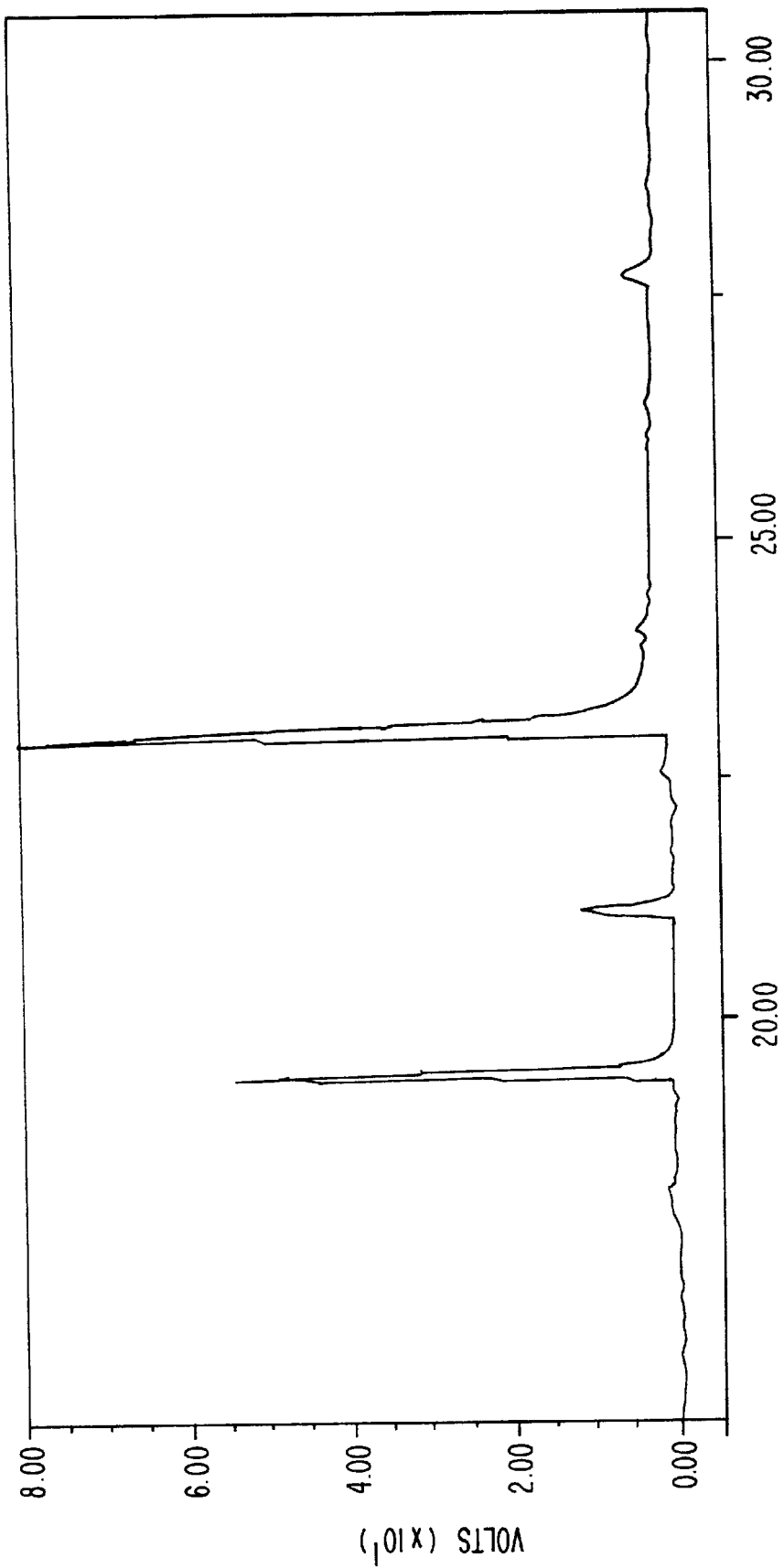

FIG. 17A shows an HPLC chromatogram of a catalytic assay of IMAC pure scFv from clone 83.

Figure 17B:
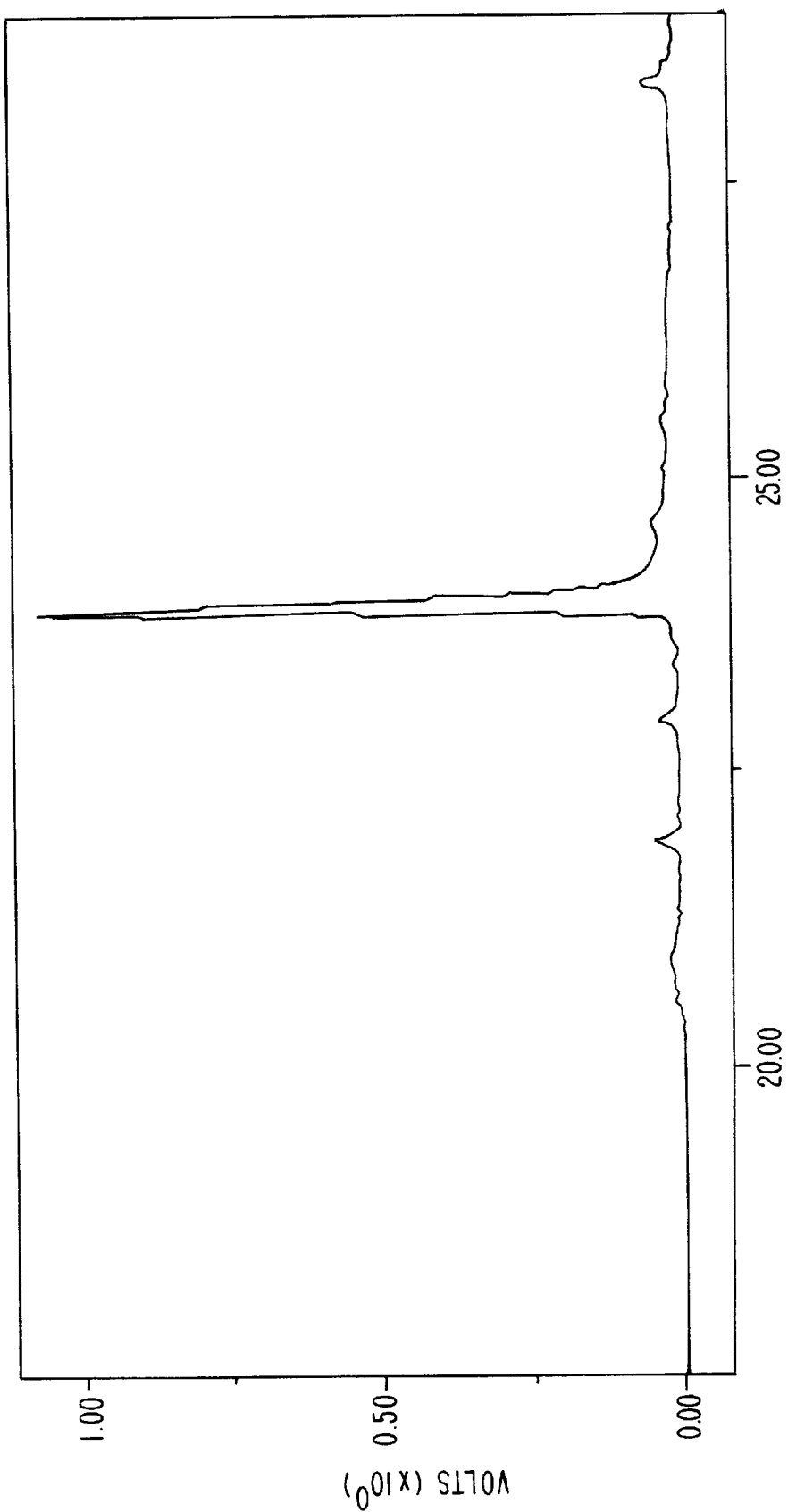

FIG. 17B shows an HPLC chromatogram of a catalytic assay +RT3 hapten of IMAC pure scFv from clone 83

Figure 18:
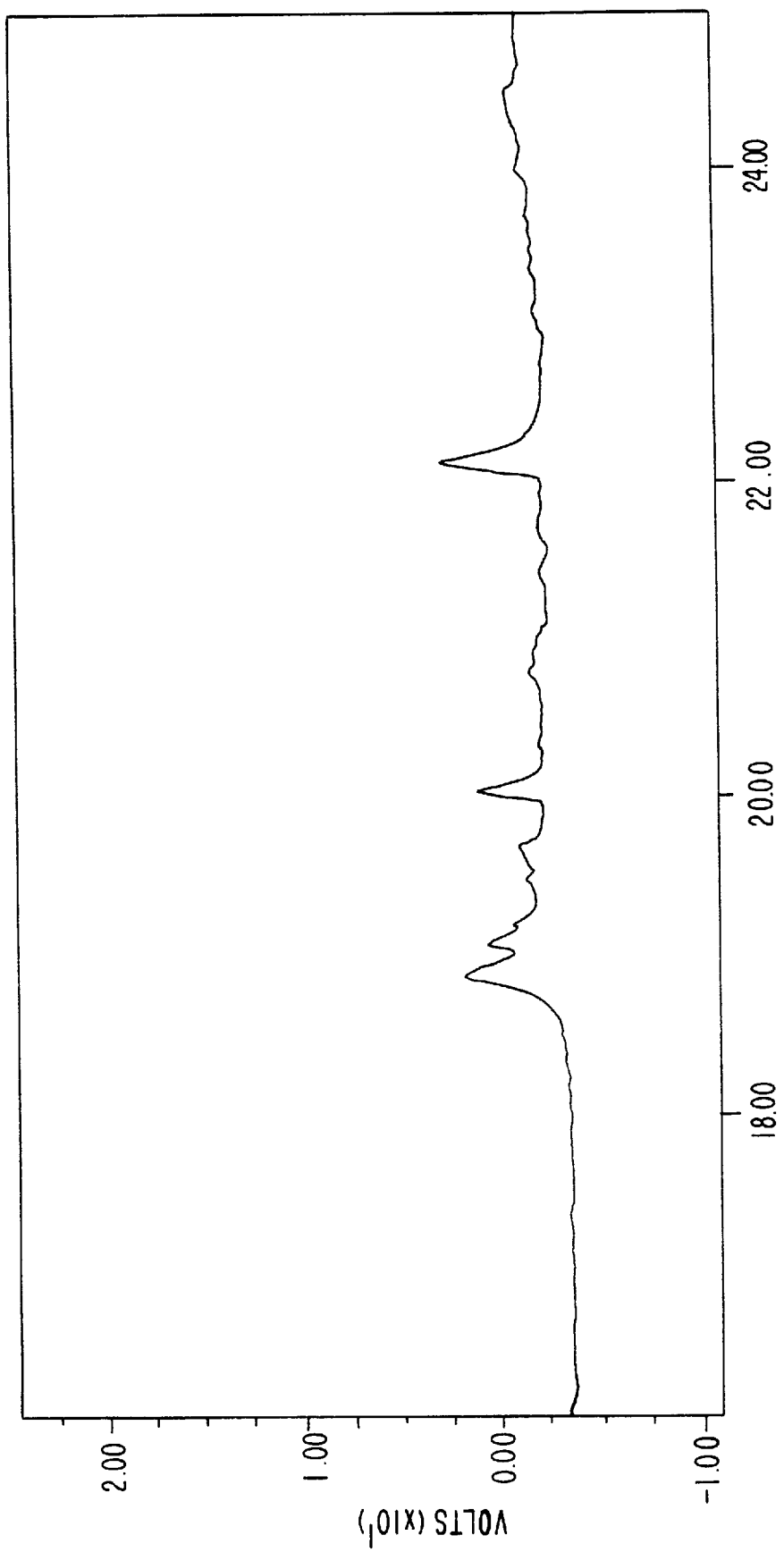

FIG. 18 shows an HPLC chromatogram of a catalytic assay of HIC pure scFv from clone 83

FIG. 19A shows binding pattern of clones to RT3 obtained after 3 rounds of panning of a naive human-derived phage antibody library.

Figure 19B:
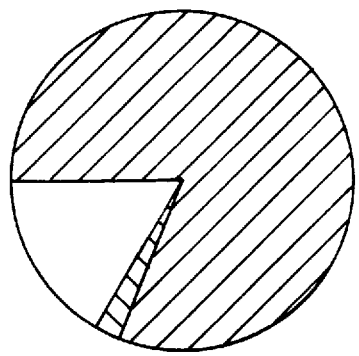

FIG. 19B shows binding pattern of clones to RT3 after 4 rounds of panning of a naive human-derived phage antibody library.

FIGS. 20A through 20F shows genetic sequences of heavy and light chains of RT3 specific phage antibodies selected from a naive human phage antibody library.

Figure 21:
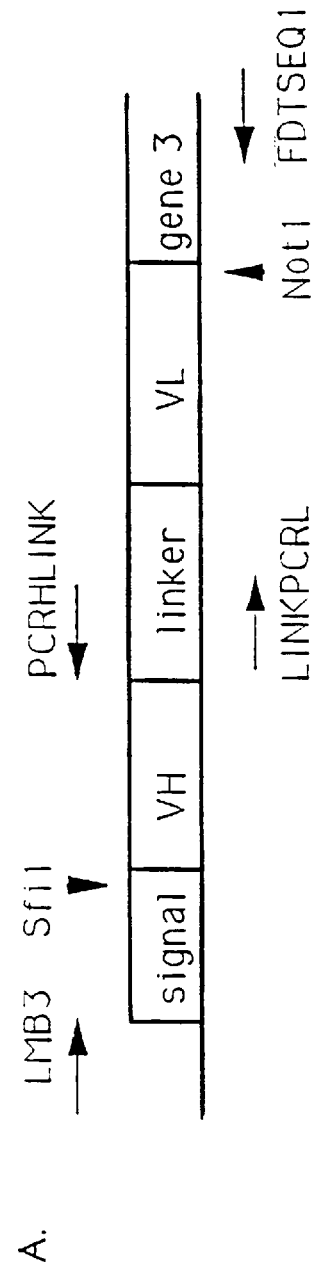

FIG. 21 shows the general scheme for VH and VL chain shuffling.

FIG. 22 shows RT3-BSA ELISA assay with polyclonal phage derived from human shufflid libraries after PAN0, PAN1, and PAN2.

FIG. 23A shows inhibitoin of phage antibody bidning to RT3-BSA by left hand portion of RT3 hapten (RT3A) or substrate (Product A).

Figure 23B:
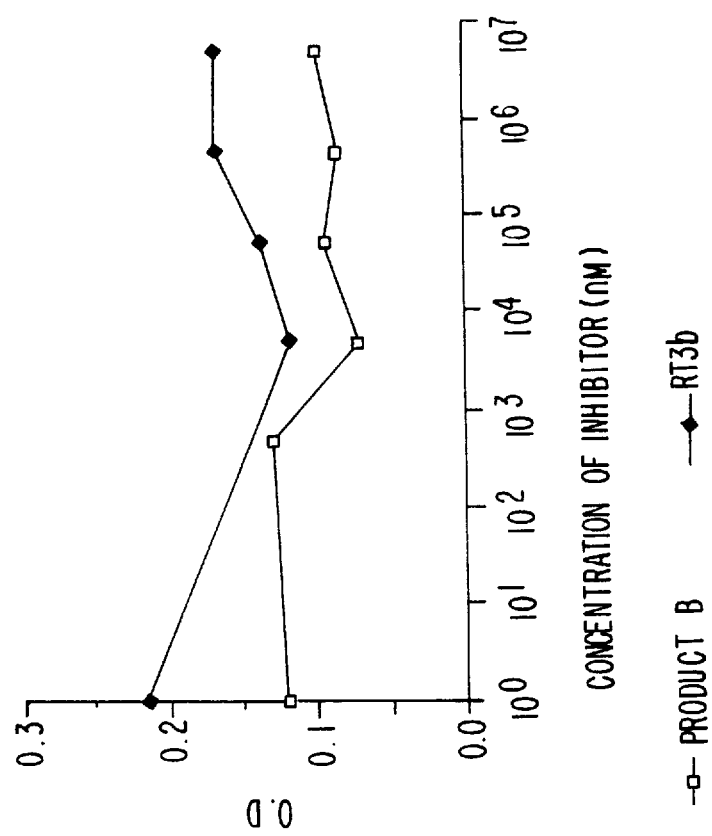

FIG. 23B shows inhibition of phage antibody binding to RT3-BSA by right hand portion of RT3 hapten (RT3B) or substrate (Product B).

Figure 24A:
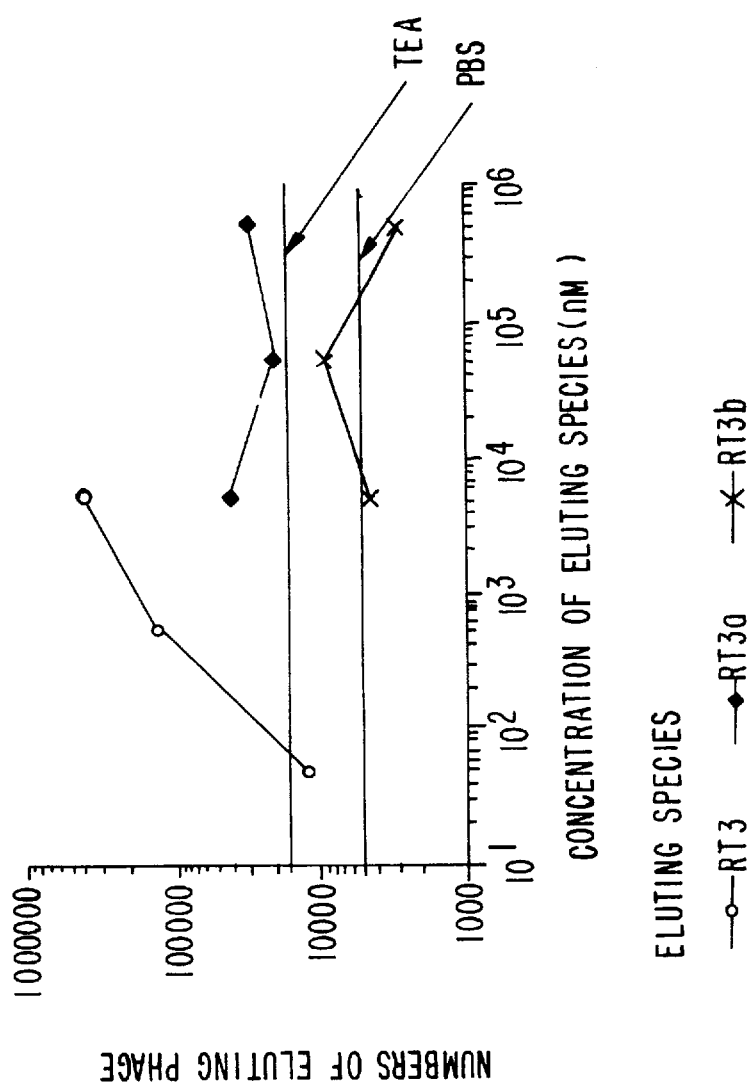

FIG. 24A shows yield of phage eluted with RT3, RT3A, RT3B, TEA and PBS from ELISA wells coated with 0.3 μg of RT3-BSA.

Figure 24B:
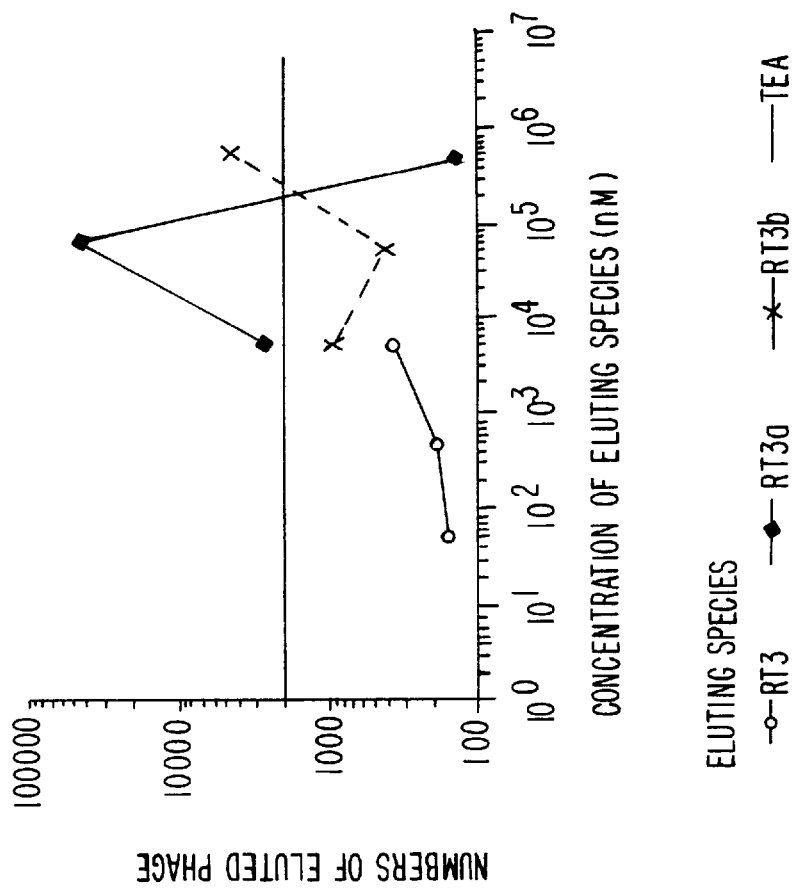

FIG. 24B shows yield of phage eluted with RT3, RT3A, RT3B, and TEA from ELISA wells coated with 15 μg of RT3-BSA.

In order that the invention herein described may be more fully understood, the following detailed description is set forth. This description, while exemplary of the present invention, is not to be construed as specifically limiting the invention and such variations which would be within the purview of one skilled in this art are to be considered to fall within the scope of this invention.

DETAILED DESCRIPTION OF THE PREFERRED EMBODIMENTS

For the sake of convenience and ready reference, the following definitions will be used in describing the instant invention.

Analog encompasses isomers, homologs, transition states or other compounds sufficiently resembling the reactant in terms of chemical structure such that an antibody raised against an analog may participate in an immunological reaction with the reactant but will not necessarily catalyze a reaction of the analog.

Antibody describes an immunoglobulin whether natural or partly or wholly synthetically produced. The term also covers any protein having a binding domain which is homologous to an immunoglobulin binding domain. These proteins can be derived from natural sources, or partly or wholly synthetically produced. Example antibodies are the immunoglobulin isotopes and the Fab, F(ab1)$_2$, scFv, fV, dAb, Fd fragments.

An antibody-derived domain refers to a sequence derived from an antibody molecule.

Antigen is a substance, frequently a protein, that can stimulate an animal organism to produce antibodies and that can combine with the antibodies these produced.

A domain is a part of a protein that is folded within itself and independently of other parts of the same protein and independently of a complementary binding member.

Homologs indicate polypeptides having the same or conserved residues at a corresponding position in their primary, secondary, or tertiary structure. The term also extends to two or more nucleotide sequences encoding the homologous polypeptides. Examples of homologous peptides are the immunoglobulin isotopes.

Isolating refers to the separation of a specific phage from the library.

Library is a collection of oligo or polynucleotides, e.g., DNA sequences within clones.

A naive library is a phage display library of immunoglobulin sequences derived from an animal which has not been immunized with the following: the reactant; the reactant bound to a peptide or other carrier, a reaction intermediate; an analog of the reactant; an analog of the product in which the antibody so generated is capable of binding to the reactant or a reaction intermediate; and an analog of a reaction intermediate or transition state.

A package describes a replicable genetic display package in which the particle is displaying a member of a sbp at its surface. The package may be a bacteriophage which displays an antigen binding domain at its surface. This type of package has been called a phage antibody (pAb).

A phage vector is a vector derived by modification of a phage genome, containing an origin of replication for a bacteriophage, but not one for a plasmid.

A phagemid vector is a vector derived by modification of a plasmid genome, containing an origin of replication for a bacteriophage as well as the plasmid origin of replication.

A vector is a DNA molecule, capable of replication in a host organism, into which a gene is inserted to construct a recombinant DNA molecule.

An Overview of the Method

The invention describes methods to generate and isolate phage particles which express on their surface an antibody with catalytic properties. In the practice of the invention the antibody domains encoding the catalytic functionality can be prepared from either specifically immunized or non-immunized animal or human sources as defined below. Additionally, the invention describes methods of generating or improving binding and/or catalytic function by one of several methodologies including but not limited to chain shuffling, CDR grafting, and mutagenesis. In a further embodiment of the invention, a method is disclosed for converting a catalytic antibody encoded entirely by mouse-derived VH and VL domains into one encode by human-derived VH and VL domains The first step in generating antibodies with specific catalytic function requires, but is not necessarily limited to, a chemical hapten (e.g., transition state analog (TSA) that is related to, but distinct from the substrate of the reaction to be catalyzed). The structure, synthesis, and use of said TSA(s) as a means to generate antibodies with catalytic function has been described in U.S. Pat. No. 4,196,265 issued Apr. 1, 1980, which is hereby incorporated by reference. As described in the prior art, the traditional route for producing and isolating catalytic antibodies has been through a monoclonal antibody approach (hybridoma technology).

Figure 1B:
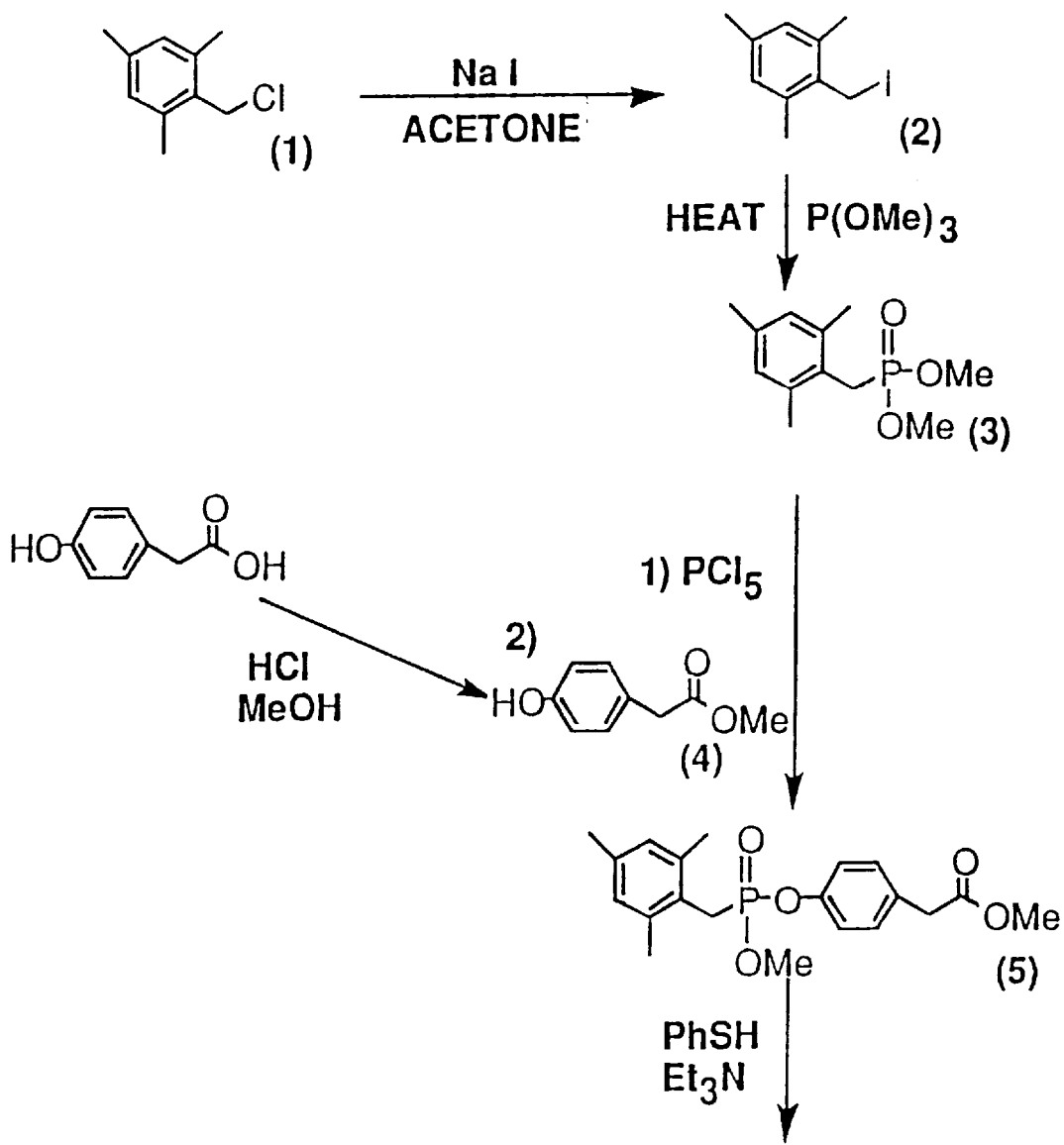

The present invention utilizes a phosphonate transition state analog as either an immunogen or immobilized on a solid phase to allow generation and selection of antibodies which bind said TSA and which may have catalytic properties (see FIG. 1). Unlike previous inventions in which catalytic antibodies are produced via hybridoma methods, the unique embodiment of the invention is the ability to express antibody domains, including those with catalytic function, on the surface of a bacteriophage. Methods for generating libraries of phage with the potential for displaying catalytic antibody domains on their surface are described in detail below.

1. Production of Binding and/or Catalytic Phage Antibodies From an Immunized Source The TSA is bound to a carrier molecule or peptide and immunized into BALB/C mice. After an appropriate amount of time spleens are removed from the mice and mRNA isolated from the cells. The RNA serves as a starting source material for amplifying immunoglobulin variable domains for cloning into bacteriophage expression vector and subsequent expression on the surface of bacteriophage particle. In the embodiment of this invention the variable domains are typically linked by a short peptide to produce a scFv as described in the background to the present invention. It should be noted that alternative phage expression vectors could be used for expression of the antibody as Fab. Techniques for creating said phage antibody libraries have been described previously and the details of the process are well known to those skilled in the art. (see, e.g., WO 92/01047; McCafferty et al., *Nature* (1990):552–564.; Hoogenboom et al., *Nucl. Acids. Res.* (1991):4133–4137; Marks et al., *J. Mol. Biol.* (1991):581–597).

Phage antibodies which specifically bind and recognize the TSA are isolated from the library by one of several methods as described below:

a) Panning—TSA is immobilized directly on a solid surface (i.e., tube or plate) or alternatively coupled to a carrier protein prior to coating the solid phase surface. A suspension containing the library of phage antibodies is allowed to react with the coated surface for some time after which unbound phage antibodies (those that do not bind the TSA) are removed by washing.

b) Affinity Chromatography—TSA is coupled to a suitable column matrix (i.e., Sepharose). Phage antibody suspension is passed over the column and unbound phage are washed through the column with buffer.

Phage antibodies that bind and are immobilized on the solid phase surface can be removed by one of several methods including:

a) Non-specific elution by using buffers of either low (acidic) or high (basic) pH.

b) Specific elution with free hapten such as the original phosphonate TSA or substrate or product of the reaction c) Specific elution with portions of the TSA, or substrate or product.

In addition to specific elution of phage antibodies bound to the TSA, it may be desirable to control the binding of the phage antibodies during the initial panning or affinity chromatography step. One method would be to use competitive inhibition in which the phage antibodies are first preincubated with reactants, reaction products or portions of the TSA (see Example 9). The purpose of such "preselection" would be to eliminate from the population of binding antibodies those least likely to be catalytic. In the context of the present example, those eliminated would be phage antibodies that do not substantially bind the phosphonate portion of the TSA. The type of preselection of the phage antibody library would need to be determined experimentally, but ultimately could lead to methods to enrich within the population of TSA binding phage antibodies the proportion of catalytic over non-catalytic phage. A greater degree of flexibility could be exerted if such procedures were carried out in ELISA wells. Thus, following a particular procedure, the eluate could be collected and the whole plate carried through a detection procedure. Based on the results, the eluate from specific wells could be selected for further analysis/pannings.

Following elution of phage antibodies by any or all of the above methods, phage are collected and can be subjected to additional pannings (2, 3, 4, 5, etc.) simply by collecting the eluted phage from the previous panning and reincubating on TSA solid phase. Since, a certain percentage of phage that do not specifically bind to the TSA are carried through each panning step (i.e., non-specific binders), pools of phage clones or individually isolated phage clones are typically rescreened for binding to the TSA by a solid phase ELISA assay. The ELISA assay can be done with antibody expressed on the bacteriophage surface or expressed in a soluble form as described below. Other formats of the ELISA assay, for example competitive inhibition with free hapten, substrate or product or various halves or portions of said hapten, substrate or product can be employed to further characterize the binding specificity of the pools of phage clones or individual binding clones.

Individual phage antibody clones or pools of clones which have the appropriate binding specificity are then assayed for catalytic activity. Assay for catalysis is most conveniently done using soluble antibody and methods for producing soluble antibody from a phage antibody expressing *E. coli* clone have been described previously (Marks et al, *J. Mol. Biol.* (1991):581–597). A criteria for attributing catalytic activity to the antibody active site is rigorous purification of the antibody away from contaminating proteins or enzymes. In this invention, purification of the soluble antibody is facilitated by incorporation of specific peptides at the 3' carboxyl terminus of the expressed antibody. Examples of such peptides currently used and as reported in the prior art include:

a) histidine peptide—allows purification of antibody on metal immobilized on a column matrix (IMAC, Hochuli et al., *Bio/Technology* (1988):1321–1325).

b) myc peptide—allows purification on a column matrix on which antibody that binds specifically to the myc peptide has been immobilized (Clackson et al. *Nature* (1991):624–628).

Figure 5A:
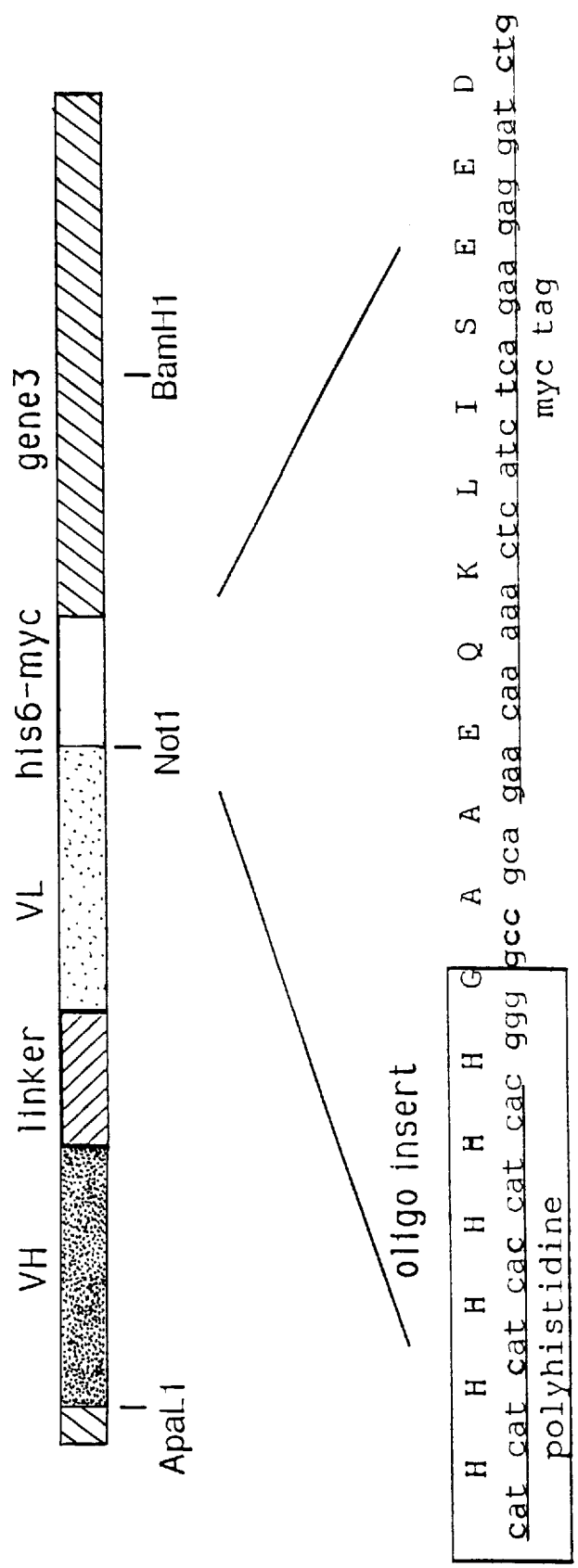

Previous vectors utilized for display of antibody fragments contained only the myc peptide (see FIG. 5). The vectors described and disclosed in this application represent the first example of incorporation of the histidine peptide in tandem with the myc peptide. This represents an improvement over the previous art because it allows purification of the soluble antibody using two uniquely different formats and purification conditions.

Additional purification of antibody can be achieved by utilizing specific properties unique to the antibody of interest such as hydrophobicity, charge, and size. Purification is affected by any of a number of standard protein purification techniques as described previously (Deutscher, *Methods in Enzymology*, Vol. 182, Guide to Protein Purification (1990).

Antibodies isolated by phage antibody techniques described above can be screened for the ability to catalyze the desired reaction by a number of methods well known in the art. In its simplest form screening is accomplished by incubating antibody and reactant (substrate) under appropriate conditions and measuring the formation of product by any of a number of means such as spectrophotometric methods or high pressure liquid chromatography.

2. Production of Binding and/or Catalytic Phage Antibodies from a Non-Immunized Source In this embodiment of the invention source material for generating a phage antibody library is from a non-immunized animal or mammal such as human. Non-immunized in this example means not specifically immunized with a specific reactant (either bound to a carrier protein or as free reactant), reaction intermediate, analog of a reactant or expected products of a particular reaction. As demonstrated in the prior art, low and moderate affinity human antibodies have been generated to specific antigens using phage antibody libraries generated from a non-immunized source. Such an approach provides a method for generating animal or human antibodies that bind to a TSA simply by panning the naive animal or human derived phage antibody library on TSA as described above. Phage clones which specifically bind and recognize the TSA can then be assayed for the desired catalytic function as described. Such an approach provides a method to isolate directly an entirely human derived catalytic antibody.

3. Production of Binding and/or Catalytic Phage Antibodies by Chain-Shuffling

A chain-shuffling approach for generating phage antibody libraries takes advantage of the promiscuity of binding between VH and VK pairs. In this embodiment of the invention, the VH or VK domain from one, several or many different phage antibody clones is recombined with a library of VK or VH domains. The phage clones and libraries of VH and VK domains can be obtained from an immunized source as described in Section 1 above or an non-immunized source as described in Section 2 above. In addition, the phage clones chosen for chain shuffling can be, but is not necessarily limited to, those that have previously been selected for binding to a particular TSA. Following the chain shuffling procedure the recombined chains (i.e., shuffled chains) are cloned back into the phage antibody expression vector. The expressed phage antibody library is repanned on the TSA and individual binding clones screened for catalytic activity as earlier described.

4. Production of Binding and/or Catalytic Phage Antibodies by CDR Shuffling

It is well known that antibody specificity and antigen binding affinity are specified by the six CDR's encoded by the VH and VL domains. It follows then that altering any or all of the CDR's from a given antibody will have dramatic effects on the binding properties of that antibody. CDR shuffling as it relates to phage antibodies describes a process for replacing a region encoding a CDR or CDR's within a VH or VL domain with a library of CDR or CDR's. As with the chain shuffling approach described in Section 3 above, the VH or VK domain used for CDR shuffling can be from one, several or many different phage antibody clones. The phage clones and libraries of CDR regions used for shuffling can be obtained from either immunized or non-immunized sources. Following CDR shuffling the recombinant VH and VL domains are recloned into the phage antibody expression vector. The expressed phage antibodies are repannned against the TSA and individual binding clones assayed for catalytic activity as described above.

5. Production of Binding and/or Catalytic Phage Antibodies by Mutagenesis

As described above for CDR shuffling binding specificity of an antibody can be altered by changing amino acids encoded within CDRs. CDR mutagenesis for the purposes of this invention can be defined as:

a) site-directed in which one or a few specific amino acids within a particular CDR are mutagenized. This process normally results in alteration of the wild-type amino sequence to several different amino acids dependent upon the nucleotide sequence of the region being mutagenized and the sequence of the mutagenic primer.

b) random mutagenesis in which some or all of the amino acids within a CDR or CDRs is replaced with a random nucleotide sequence such that the wild type sequence is replaced by all possible combinations of amino acids.

A number of different methodologies for both site-directed and random mutagenesis have been described in the literature and are well known to those in the art. As with the other methodologies, the phage antibody clone or clones chosen for mutagenesis could be, but is not limited to, ones already selected for binding to the TSA. In addition, the chosen binding clones could be ones isolated from phage antibody libraries derived from either immunized or non-immunized animal or human sources.

Recent successes in modelling antigen binding sites augurs well for de novo design. The approach is especially attractive for making, catalytic antibodies, particularly for small substrates. Here side chains or binding sites for prosthetic groups might be introduced, not only to bind selectively to the transition state of the substrate, but also to participate directly in bond making and breaking.

6. Derivation of Human Catalytic Antibodies by "imprinting"

The process of "imprinting" involves using an existing antibody with desired binding characteristics, to derive new antibodies, with similar characteristics. This is done by recombining original antibody chains, or parts thereof, with a library of complementary parts. When new antibody elements are found, which complement the original antibody binding characteristics, these are recombined with a library which replaces the original antibody binding characteristics, these are recombined with a library which replaces the original antibody part, to give an entirely new antibody which mimics the binding of the original antibody (PCT/GB/92/01755).

For example, an imprinting approach would have value for humanizing a mouse catalytic antibody isolated using phage antibody technology as described in Section 1 above. Once isolated, the mouse encoded VH or VL domain of the catalytic antibody could be recombined with a library of the complimentary human derived VL or VH domains. The half mouse-half human phage antibodies are then reselected for binding to the TSA used originally to generate the catalytic activity. The remaining mouse VH or VL domain of the selected binders is now replaced with a library of the complimentary human derived VL or VH domains. The resulting phage antibodies which now are encoded entirely by human derived sequences entirely are again reselected for binding to the TSA. Individual clones selected for binding to the TSA are then assayed as described above for catalytic activity.

Having now generally described this invention, the following examples are included for purposes of illustration and are not intended as any form of limitation.

EXAMPLE 1.1

Synthesis of RT3 Phosphonate Transition State Analog Hapten

The reaction scheme for the synthesis of the RT3 phosphonate transition state analog is shown in FIG. 1. α2-Chloroisodurene (1) by halogen exchange using sodium iodide in acetone gave α2-Iodoisodurene (2). Michaelis-Arbusov reaction with trimethylphosphite yielded the dimethoxy phosphonate compound (3). Activation by heating with phosphorus pentachloride and subsequent reaction with Methy 4-Hydroxyphenylacetate (4) afforded compound (5). Demethylation using thiophenol and triethylamine produced compound (6) which under strong basic conditions of lithium hydroxide was fully deprotected to the derised product (7).

More specifically, α2-Iodoisodurene (Compound 2) was prepared as follows:

α2-Chloroisodurene (Compound 1) (2.28 g) was dissolved in acetone (45 ml) and NaI (2.25 g) was added. The reaction mixture was stirred vigorously at 75° C. in the dark for 16 hours. The reaction mixture was concentrated, redissolved in ethyl acetate (100 ml), washed with water and concentrated to a solid. The solid was redissolved in ethyl acetate (5 ml) and purified by flash chromatography using 100 g of silica and eluting with hexane to give α2-Iodiosodurene (2) (2.717 g). This was confirmed by spectroscopy $^1$H NMR ($CDCl_3$) δ2.25 (s,3 H), 2.33 (s, 6 H), 4.48 (s, 2 H), 6.85 (s, 2 H).

Preparation of Compound 3

Freshly distilled Trimethoxyphosphite (5 ml) and α2-Iodoisodurene (2) (0.765 g) were heated together at 110° C. for 16 hours. Te reaction mixture was concentrated to a small volume and purified by flash chromatography using 50 g of silica and eluting with ethyl acetate-hexane (2:8 volume by volume) to give compound 3 (0.550 g). This was confirmed by spectroscopy—$^1$H NMR ($CDCl_3$) δ 2.25 and 2.27 (2s, 3 H), 2.40 (1s, 6 H), 3.25 (d, 2 H), 3.65 (d, 6 H), 6.88 (s, 2 H).

Methyl 4-Hydroxyphenylacetate (Compound 4)

4-Hydroxyphenylacetic acid (1.75 g) was dissolved in methanol (30 ml) and 10M aqueous hydrochloric acid (0.15 ml) was added and heated to reflux for 15 hours. After cooling to room temperature, triethylamine (1 ml) was added, the mixture concentrated, purified by flash chromatography using silica gel (30 g) and eluted with ethyl acetate-hexane (2:8 volume by volume) to give Methyl 4-Hydroxyphenylacetate (4) (1.693 g). This was confirmed by spectroscopy—$^1$H NMR ($CDCl_3$) δ 3.58 (s, 2 H), 3.73 (s, 3 H), 6.75 (d, 2 H), 7.10 (d, 2 H).

Preparation of Compound 5

Compound 3 (0.243 g) was dissolved in dry chloroform (3 ml) and a solution of phosphorus pentachloride (0.240 g ) in dry chloroform (3 ml) added followed by heating at 60° C. for 3 hours. The reaction mixture was concentrated to an oil which was left to stir under high vacuum for 16 hours. The resultant phosphorochloridate was redissloved in dry dichloromethane (3 ml) and added to a solution of Methyl 4-Hydroxyphenylacetate (4) (0.150 g) and 4-Dimethylaminopyridine (0.146 g) in dry dichloromethane (3 ml) at 0° C. The reaction mixture was stirred at room temperature for 16 hours. Saturated aqueous ammonium chloride (15 ml) was added and products were extracted into dichloromethane (40 ml). The organic layer was washed with water (10 ml), dried over anhydrous $MgSO_4$, filtered and concentrated then purified by flash chromatography using silica (30 g) and eluting with ethyl acetate-hexane (4:6 volume by volume) to give compound 5 (0.20 g). This was confirmed by spectroscopy—$^1$H NMR ($CDCl_3$) δ 2.27 and 2.30 (2s, 3 H), 2.40 and 2.42 (2s, 6 H), 3.40 (d, 2 H), 3.58 (s, 2 H), 3.67 (d, 3 H), 3.69 (s, 3 H), 6.88 (s, 2 H), 7.05 (d, 2 H), 7.20 (d, 2 H).

Preparation of Compound 6

Compound 5 (0.19 g) was dissolved in dioxane (1.5 ml). Thiophenol (0.575 g) and triethylamine (0.70 ml) were added and the reaction mixture was stirred for 16 hours. The mixture was concentrated, redissolved in water (30 ml) and washed with dichloromethane ( 5×25 ml). The aqueous layer was adjusted to pH 1 with aqueous HCl and extracted with ethyl acetate (5×30 ml). The organic layers were combined, dried over anhydrous $MgSO_4$, filtered and concentrated to give compound 6 (0.176 g). This was confirmed by spectroscopy—$^1$H NMR ($CDCl_3$) δ 2.15 (bs, 3 H), 2.28 (bs, 6 H), 3.13 (d, 2 H) 3.40 (bs, 2 H), 3.60 (bs, 3 H), 6.68 (bs, 2 H), 6.85 (bs, 2 H), 7.00 (bs, 2 H).

Preparation of Compound 7

Compound 6 (0.087 g) was treated with a solution of lithium hydroxide monohydrate (0.025 g) in methanol (1.4 ml) and water (0.30 ml) with vigorous stirring for 50 hours. The reaction mixture was concentrated to a third of its volume, water (10 ml) was added and the aqueous layer was washed with dichloromethane (3×10 ml). The aqueous layer was adjusted to pH 1 with concentrated HCl and was extracted with ethyl acetate (7×20 mL). Organic layers were combined, dried over anhydrous $MgSO_4$, filtered and concentrated to give compound 7 (0.063 g). This was confirmed by spectroscopy—$^1$H NMR ($d_6$ DMSO) δ 2.170 and 2.175 (2 s, 3 H), 2.30 (s, 6 H), 3.20 (d, 2 H), 3.50 (s, 2 H), 6.80 (s, 2 H), 7.00 (d, 2 H), 7.20 (d, 2 H).

EXAMPLE 1.2

Synthesis of Left Hand Portion (Compound 8) of RT3 Phosphonate Transition State Analog (RT3A) (see FIG. 2)

Preparation of Compound 8 from the Demethylation of Compound 3 using Thiophenol and Triethylamine.

Compound 3 (0.122 g) was dissolved in dioxane (1.5 ml) and with stirring a solution of thiophenol (0.55 g) in dioxane (1.5 ml) was added. Triethylamine (0.70 ml) is then added and the solution is stirred for 24 hours at room temperature. Reaction mixture was transferred to a separating funnel, water (50 ml) was added, the aqueous layer was adjusted to pH 7 with aqueous HCl and then it was washed with dichloromethane (5×50 ml). The aqueous layer was acidified to pH 1 with 1M aqueous HCl and extracted with ethyl acetate (2×75 ml). The organic layers were combined and washed with water (5 ml), dried over anhydrous $MgSO_4$, filtered and concentrated. Purification using silica (10 g) and eluting with methanol-dichloromethane (8:92 volume by volume–15:85 volume by volume) gave compound 8 (0.055 g). This was confirmed by spectroscopy—$^1$H NMR ($d_6$ DMSO) δ 2.10 (bs, 3 H), 2.28 (bs, 6 H), 3.2 (d, 2 H), 3.30 (d, 3 H), 6.85 (s, 2 H).

EXAMPLE 1.3

Figure 3:
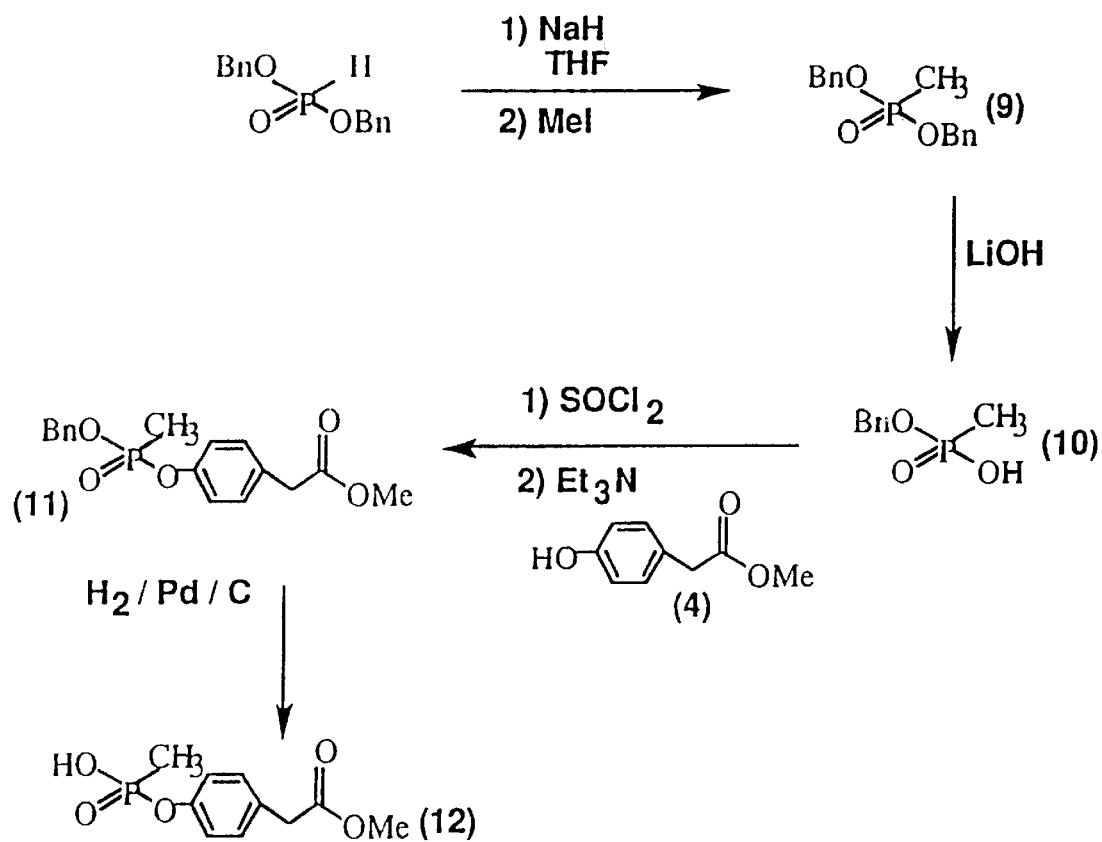

Synthesis of Right Hand Portion (Compound 12) of RT3 Phosphonate Transition State Analog (RT3B) (see FIG. 3)

Preparation of Dibenzylmethylphosphorate (Compound 9)

Sodium hydride (60% dispersion in mineral oil) (0.16 g) was washed with dry hexane (2×10 ml). To the decanted solid, dry THF (5 ml) was added and the stirred suspension was cooled to 0° C. A solution of Dibenzyl phosphite (1.048 g) in dry THF (5 ml) was added and the mixture warmed to room temperature. After 30 minutes, methyl iodide (0.32 ml) was added and the reaction mixture stirred for 2 hours. The reaction mixture was concentrated, redissolved in ethyl acetate (75 ml), washed with saturated aqueous ammonium chloride solution (50 ml) and water (10 ml). The organic layer was dried over anhydrous $MgSO_4$, filtered, concentrated then purified by flash chromatography using silica (10 g) and eluting with ethyl acetate-hexane (1:1 volume by volume) which gave Dibenzylmethylphosphonate (9) (0.750 g). This was confirmed by spectroscopy—$^1$H NMR (CDCl$_3$) δ 1.48 (d, 3 H), 5.00 (m, 4 H), 7.40 (s, 10 H).

Preparation of Benzylmethylphosphoric Acid (Compound 10)

Dibenzylmethylphosphonate (9) (0.277 g) was dissolved in dioxane (1 ml) and water (0.5 ml). Aqueous 2M LiOH (1 ml) was added and the mixture was vigorously stirred for 48 hours. Water (25 ml) was added and the aqueous layer was washed with ethyl acetate (25 ml). The aqueous layer was acidified to pH 1 with concentrated HCl and extracted with ethyl acetate (2×35 ml). Organic layers were combined, dried over anhydrous $MgSO_4$, filtered and concentrated to give Benzylmethylphosphoric acid (10) (0.183 g). This was confirmed by spectroscopy—$^1$H NMR (CDCl$_3$) δ 1.53 (d, 3 H), 5.08 (d, 2 H), 7.40 (m, 5 H), 11.90 (s, 1 H).

Preparation of Compound 11

Benzylmethylphosphoric acid (10) (0.118 g) was dissolved in thionyl chloride (1 ml) and stirred for 4 hours. The reaction mixture was concentrated to dryness and was left under high vacuum for 16 hours. This was redissolved in dry dichloromethane (1 ml) and DMF (1.5 ml). With stirring Methyl 4-Hydroxyphenyl acetate (4) (0.083 g) and triethylamine (0.170 mL) was added. After 16 hours, saturated aqueous ammonium chloride (30 ml) was added and the mixture was extracted with ethyl acetate (2×50 ml). Organic extracts were combined, dried over anhydrous $MgSO_4$, filtered and concentrated. Purification was achieved using preparative tlc plates (1 mm) and using ethyl acetate-hexane (4:6 volume by volume) as the solvent to give compound (11) (0.068 g). This was confirmed by spectroscopy—$^1$H NMR (CDCl$_3$) δ 1.67 (d, 3 H), 3.60 (s, 2 H), 3.73 (s, 3 H), 5.15 (m, 2 H), 7.13 (d, 2 H), 7.25 (d, 2 H), 7.40 (s, 5 H).

Preparation of Compound 12

Methylation of dibenzyl phosphite using methyl iodide gave Dibenzyl methyl phosphonate (9) which on lithium hydroxide hydrolysis afforded the phosphoric acid 10. Activation with thionyl chloride and subsequent reaction with Methy 4-Hydroxyphenylacetate (4) produced compound 11. Final product 12 was obtained by the catalytic hydrogenation of 11.

Compound 11 (0.060 g) was dissolved in ethyl acetate (10 ml) and 10% palladium on charcoal (0.03 g) was added. The mixture was stirred under an atmosphere of hydrogen for 3 hours. It was then filtered through a bed of celite and ethyl acetate (2×10 ml) added to wash products from the celite. All washings and filtrates were combined and concentrated to give compound 12 (0.038 g). This was confirmed by spectroscopy—$^1$H NMR (CDCl$_3$) δ 1.48 (vbs, 3 H), 3.60 (bs, 2 H), 3.68 (bs, 3 H), 7.15 (m, 4 H), 8.20 (vbs, 1 H).

EXAMPLE 1.4

Figure 4:
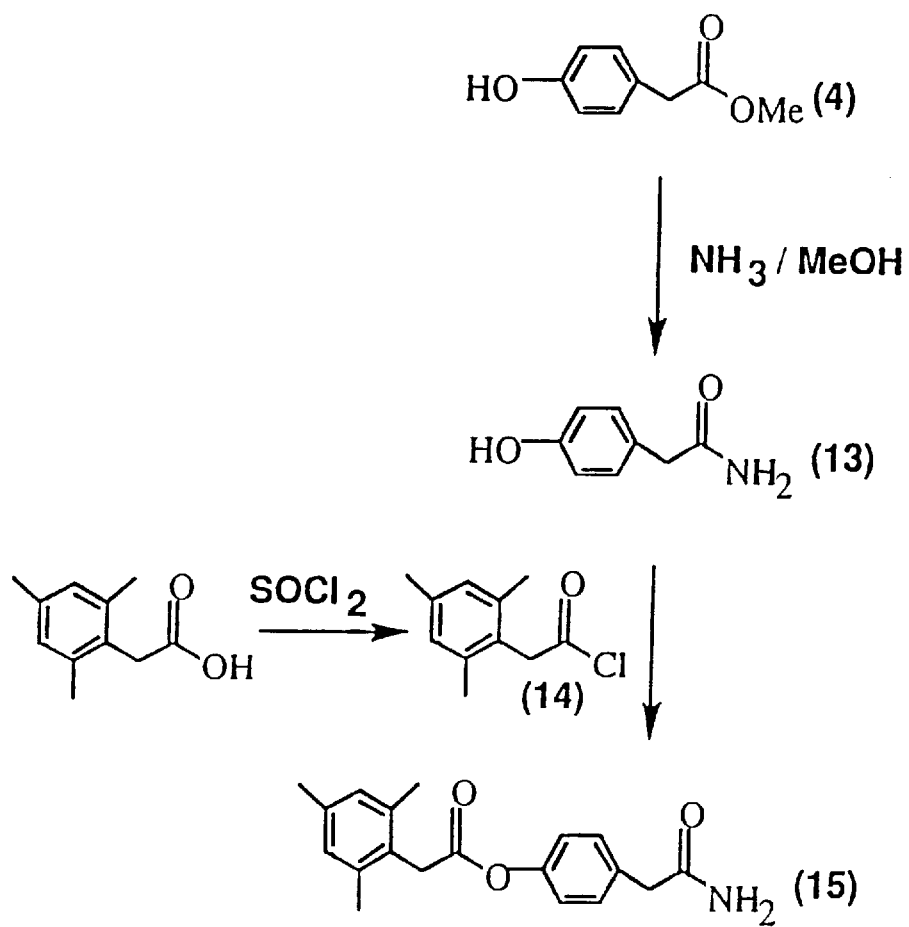

Synthesis of RT3 Substrate (see FIG. 4)

Preparation of 4-Hydroxyphenylacetamide (Compound 13)

Methyl 4-Hydroxyphenylacetate (4) (0.83 g) was dissolved in saturated methanolic ammonia (30 ml) and placed in a thick walled tube with Teflon screw cap. The solution was stirred in this sealed tube at room temperature for 72 hours. Reaction mixture was concentrated and redissolved in methanol-chloroform (2:8 volume by volume, 75 ml). No crystallization occurred so the solution was concentrated to half its volume and hexane was added with heating. Cooling to 0° C. gave crystals of 4-Hydroxyphenylacetamide (13) (0.524 g). This was confirmed by spectroscopy—$^1$H NMR ($d_6$ DMSO+CF$_3$CO$_2$D) δ 3.23 (s, 2 H), 6.63 (d, 2 H), 7.00 (d, 2 H).

Preparation of Compound 15

The amide 13 was prepared by the ammonolysis of the methyl ester 4. Activation of mesitylacetic acid with thionyl chloride and subsequent reaction with amide 13 gave the final compound 15.

Mesitylacetic acid (0.10 g) was dissolved in thionyl chloride (1 ml) and stirred for 4 hours. The reaction mixture was concentrated to dryness and placed under high vacuum for 16 hours. The resultant mesitylacetylchloride (14) was dissolved in dry dichloromethane (1 ml) and added to a solution of 4-Hydroxyphenylacetamide (13) (0.076 g) and triethylamine (0.077 mL) in dry DMF (1 ml). The reaction mixture was stirred for 90 minutes then concentrated, redissolved in ethyl acetate (30 ml) and washed with saturated aqueous sodium bicarbonate (25 ml) and water (5 ml). The organic layer was dried over anhydrous $MgSO_4$, filtered and concentrated. Purification was acheived by preparative silica tlc (1 mm) using ethyl acetate as solvent to give compound 15 (0.055 g). This was confirmed by spectroscopy—$^1$H NMR ($d_6$ DMSO+CF$_3$CO$_2$D) δ 2.13 (s, 3 H), 2.23 (s, 6 H), 3.35 (s, 2 H), 3.83 (s, 3 H), 6.80 (s, 2 H), 6.93 (d, 2 H), 7.23 (d, 2 H).

EXAMPLE 2

Hapten Conjugations

RT3 hapten, 4-(carboxymethyl) phenyl-(2,4,6-trimethylphenyl)-methyl phosphonate (compound 7, FIG. 1), was conjugated to bovine serum albumin (BSA) and keyhole limpet hemocyanin (KLH), via the free carboxyl group on the hapten.

5.4 mg of RT3 was dissolved in phosphate buffer at 37° C., and then mixed with 6 mg EDC, 1-ethyl-3-(3- dimethylaminopropyl) carbodiimide-HCl, and N-hydroxysulfosucccinimide (S—NHS), at a molar ratio of 1:2:2, respectively. 10 mg of BSA was dissolved in water and then added to the hapten. The molar ratio of hapten to BSA was 100:1, using a BSA molecular weight of 64,000. The mixture was stirred at room temperature for 3 hours and then dialyzed against 2 changes of phosphate buffered saline (PBS) at 4° C. over 2 days.

The RT3-KLH conjugate was made in a similar manner to RT3-BSA except that the pH of the hapten, EDC, S—NHS mixture was adjusted to 6.0 with NaOH before the addition of the KLH. The hapten to protein ratio was 100:1 using a protein molecular weight of 64,000. The reaction mixture was stirred for 2 hours at room temperature, and then dialyzed against PBS at 4° C. over 2 days.

After the dialysis, the protein concentrations were determined by the micro-bicinchonic acid assay using BSA as the protein standard (Pierce, Rockford, Ill.).

EXAMPLE 3

Immunizations And MRNA Isolation

BALB/c female mice, 14-weeks-old, were injected intraperitoneally with 50 μg of RT3-KLH emulsified in complete Freund's adjuvant. The mice were boosted with 10 μg of RT3-KLH emulsified in incomplete Freund's adjuvant at weeks 4 and 7. The mice were sacrificed three days after the last injection and the spleen removed and used as a source of mRNA. The immune response after the second injection was measured by ELISA. The titer of the antiserum against RT3-BSA was 1:100,000.

Preparation of mRNA—mRNA was isolated from 105 mg of spleen obtained from a mouse immunized with RT3-KLH as described above. mRNA was purified using a FastTrack mRNA isolation kit (Invitrogen Corp, San Diego, Calif.) following manufacturers instructions. The mRNA yield was 5.4 ug as determined spectrophotometrically using the following formula:

[mRNA]=($A_{260}$) (0.04 ug/ul) D where D is the dilution factor

EXAMPLE 4

Materials and Methods for Construction Of Phage Display Libraries

Protocols used in the following procedures were described in Sambrook et al., Molecular Cloning: A Laboratory Manual, Cold Spring Harbor Laboratory Press (1989).

Restriction digestion, analysis of restriction enzyme digestion products on agarose gels, purification of DNA using phenol/chloroform, preparation of 2×TY medium and plates, preparation of tetracycline and ampicillin stock solutions, PAGE of proteins, Preparation of phosphate buffered saline, preparation of plasmid DNA by alkaline lysis, cesium chloride purification of plasmid DNA.

All enzymes were supplied by New England Biolabs (Beverly, Mass.) and were used according to manufacturer's instructions unless otherwise stated.

Ligations were done using an Amersham (Arlington Heights, Ill.) ligation kit. DNA purifications using glass milk (Bio 101, La Jolla, Caolf. ) or magic minipreps or magic PCR preps (Promega, Madison, Wis.) were done according to manufacturers conditions.

Preparation of competent cells and transformation were done according to the method described in the Bio-Rad (Hercules, Calif.) electro-transformation protocols.

The following are described in McCafferty et al., 1992, Patent No. W092/01047: preparation of phage, phagemid particles, single stranded DNA, expression of soluble single chain Fv antibodies, the procedures for panning and ELISA, analysis of diversity by PCR and BstN1 digestion.

DNA was transformed into competent TG1 cells (genotype: K12d(lac-pro), sup E, thi, hsdD5/F'traD36, pro A+B+, Lac Iq, lac ZdM15) or HB2151 cells (genotype: K12d(lac-pro), thi/F' pro A+B+, Lac IqZ dM15).

The mouse PCR primers, the vector pCANTAB 3 and pCANTAB 5, and anti-M13 antibodies are available from Pharmacia (Piscataway, N.J.) (Cat. No. 27-9400-01, 27-9401-01, 27-9402-01 respectively).

EXAMPLE 4.1

Preparation Of Vectors Facilitating Rapid/Multiple Isolations Of Soluble Single Chain Fv (scFv) Antibodies Using "Immobilized Metal Affinity Chromatograph Procedure" (IMAC)

In screening for catalytic antibodies, it would be advantageous to have a means of readily purifying/concentrating bacterially expressed antibodies from phagemid vectors. The following changes were incorporated into the phagemid vectors pHEN, pCANTAB (see McCafferty et al., (1992) Patent Application WO 92/01047, Hoogenboom H. R. et al., Nucli. Acid Res. 19, (1991):4133–4137, Pharmacia product literature Cat. No. 27-9401-01):

i) sequences encoding six histidine residues at the C terminus of the antibody were introduced.

ii) sequences encoding a myc tag peptide at the C terminus of the antibody were included for sensitive detection/alternative purification of SCFv's. By incorporating these changes, a very simple and rapid procedure for concentrating and purifying bacterially expressed antibodies has been developed.

Two pairs of oligonucleotides were synthesised to generate the double stranded inserts shown below. These have 5' overhangs compatible with the Not1 site and so can be cloned into this site in pHEN, pCANTAB, regenerating the Not1 site at the 5' end as shown below.

His-6 1/2

|  | ala | ala | his | his | his | his | his | his | amb |  |  |
|---|---|---|---|---|---|---|---|---|---|---|---|
| 5' G | GCC | GCA | CAT | CAT | CAT | CAC | CAT | CAC | TA |  | 3' (see SEQ ID NO:1) |
| 3' |  | CGT | GTA | GTA | GTA | GTG | GTA | GTG | ATC | CGG | 5' (see SEQ ID NO:2) |

His-6 3/4

|  | ala | ala | his | his | his | his | his | his | gly |  |  |
|---|---|---|---|---|---|---|---|---|---|---|---|
| 5' G | GCC | GCA | CAT | CAT | CAT | CAC | CAT | CAC | GG |  | 3' (see SEQ ID NO:3) |
| 3' |  | CGT | GTA | GTA | GTA | GTG | GTA | GTG | CCC | CGG | 5' (see SEQ ID NO:4) |

(amb = amber codon)

His-6 ¾ was cloned into pHEN-OX16 which consists of the high affinity oxazalone binding clone described in Clackson et al., Nature 352 (1991):624–628, cloned into the Pst1/Not1 site of pHEN1. This construct will give rise to a product consisting of [aOX antibody-his-6-myc tag-amber codon- gene3] which can be detected with the 9E10 antibody 9 (the cell line producing 9E10 antibody 9 is available from ATCC, Rockville, Md., CRL1729 designated MYC1-9E10.2). The new construct is called pOX16his-11 and is shown in FIG. 5.

This clone was used to work out the "immobilized metal affinity chromatography procedure" (IMAC) purification regime described below. An additional construct, was made by inserting His-6 ½ into the clone scFv4, which consists of the lysozome binding D1.3 scFv antibody cloned into pCANTAB3. This construct will give rise to a product consisting of (D1.3 antibody-his-6-amber codon- gene 3) which can be detected with anti-D1.3 antiserum.

All cloning manipulations were carried out in TG1 and the correct clones introduced into the non-suppressor strain HB2151 for expression as single chain Fvs.

All volumes are for an initial culture volume of 50 mls and all bacterial growth was at 30° C. in the host HB2151. E. coli cells carrying the plasmid of interest were grown to 0.7–1.0 O.D./ml in 2xTY medium supplemented with 2% glucose, 100 µg/ml ampicillin. The culture was centrifuged in a 50 ml Falcon tube at 3500 rpm for 10 minutes at room temperature, resuspended in 2xTY/100 µg/ml ampicillin/1 mM IPTG and grown for 3 hours. The culture was centrifuged in a 50 ml Falcon tube at 3500 rpm for 15 minutes at a temperature of 4° C. and is resuspended in 1 ml of cold buffer A (PBS/1M NaCl/1 mM EDTA) and left on ice for 15 minutes. The sample was centrifuged 2x10 minutes, the supernatant carrying the periplasmic contents collected and $MgCl_2$ added to 1–2 mM.

400 µl of a 1:1 slurry of Ni-NTA agarose:buffer 1 (Qiagen, Chatsworth, Calif.) which had been pre-equilibrated with buffer A was added to the periplasmic preparation and incubated for 10 minutes on an inverting platform at room temperature. The mixture was centrifuged at low speed on a microfuge for 10–15 seconds and the pellet resuspended in 1 ml of buffer A. This process was repeated another 2 times before resuspending in 100 µl of either PBS or buffer A carrying 250 mM imidazole. After 10 minutes the supernatant was collected and the pellet re-extracted with another 100 µl of the same buffer and pooled.

Figure 6:
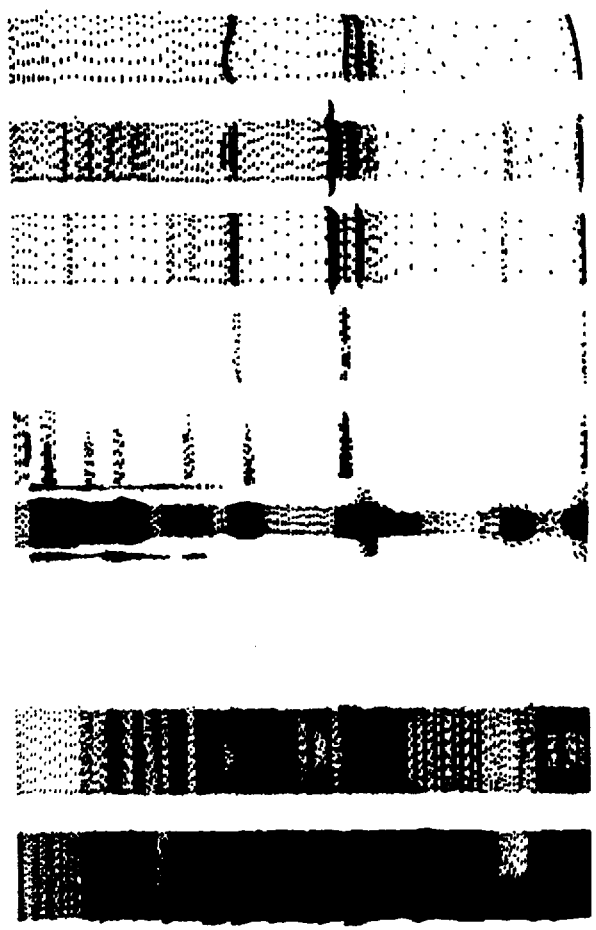
FIG. 6 shows an SDS polyacrylanide gel starved with coomassie are.

Results are shown in FIG. 6, in lanes marked with the capital letters A, B, C, D, E and F. Lane A, FIG. 6 shows abundant accumulation of scFv in the periplasm after 3 hours induction. As expected scFv was only found in the culture supernatant after overnight incubation (data not shown). Isolation of antibody from the periplasm not only has the advantage that it can be prepared after a shorter induction, with the potential for a better quality product, but also the initial centrifugation step itself effectively concentrates the antibody, when working from the periplasm. Lanes B and C show that the antibody fragment is efficiently bound and recovered after incubating the Ni-NTA matrix with periplasmic extract (see Lane A) and eluting bound scFv with Buffer A/250 mM Imidazole as described above. Lanes D and E shows that elution can be carried out in PBS/250 mM imidazole, without added NaCl. This may be a more useful buffer for subsequent use of the antibody. Lane F shows that the clone scFv4his-6 produces an antibody fragment which can be recovered in the same way.

This procedure is a very simple means of concentrating/purifying antibodies which will facilitate the preparation of multiple samples simultaneously as required for screening for catalysis.

Vector forms of the above construct were prepared by cleavage with Not1 and Bam H1 to isolate DNA extending from the Not1 cloning site through to the BamH1 site in the middle of gene III. This was used to replace the equivalent Not1/BamH1 site within PCANTAB 3 and pCANTAB5 to give the vectors PCANTAB 3 his-6 and pCANTAB5 his-6. This transfers the myc tag and the his-6 tag to the new backbone (FIG. 7).

EXAMPLE 4.2

Preparation Of A Phage Library Derived From Mice Immunized With RT3

Sequences of all primers used for the construction, PCR and sequence analysis of mouse derived phage display libraries are shown below:

SEQUENCE OF BK PRIMARY PRIMERS.

| | |
|---|---|
| VKA BACK | 5' GAT GTT TTG ATG ACC CAA ACT CCA 3' (see SEQ ID NO:5) |
| VKB BACK | 5' GAT ATT GTG ATA ACC CAG GAT GAA 3' (see SEQ ID NO:6) |
| VKC BACK | 5' GAC ATT GTG CTA/G ACC CAG TCT CCA 3' (see SEQ ID NO:7) |
| VKD BACK | 5' GAC ATC CAG ATG ACN CAG TCT CCA 3' (see SEQ ID NO:8) |
| VKE BACK | 5' CAA ATT GTT CTC ACC CAG TCT CCA 3' (see SEQ ID NO:9) |
| VKF BACK | 5' GAA AAT GTG CTC ACC CAG TCT CCA 3' (see SEQ ID NO:10) |
| MJK1FONX | 5' CCG TTT GAT TTC CAG CTT GGT GCC 3' (see SEQ ID NO:11) |
| MJK2FONX | 5' CCG TTT TAT TTC CAG CTT GGT CCC 3' (see SEQ DI NO:12) |
| MJK4FONX | 5' CCG TTT TAT TTC CAA CTT TGT CCC 3' (see SEQ ID NO:13) |
| MJK5FONX | 5' CCG TTT CAG CTC CAG CTT GGT CCC 3' (see SEQ ID NO:14) |

SEQUENCE OF VH PRIMARY PRIMERS.

| | |
|---|---|
| VH1FOR-2 | 5' TGA GGA GAC GGT GAC CGT GGT CCC TTG GCC CC 3' (see SEQ ID NO:15) |
| VH1BACK | 5' AGG TSM ARC TGC AGS AGT CWG G 3' (see SEQ ID NO:16) |

SEQUENCE OF VK LINKER PRIMERS.

| | |
|---|---|
| VKALINKFOR | TGG AGT TTG GGT CAT CAA AAC ATC CGA TCC GCC ACC GCC AGA GCC (see SEQ ID NO:17) |
| VKBLINKFOR | TTC ATC CTG GGT TAT CAC AAT ATC CGA TCC GCC ACC GCC AGA GCC (see SEQ ID NO:18) |
| VKCLINKFOR | TGG AGA CTG GGT T/CAG CAC AAT GTC CGA TCC GCC ACC GCC AGA GCC (see SEQ ID NO:19) |
| VKDLINKFOR | TGG AGA CTG XGT CAT CTG GAT GTC CGA TCC GCC ACC GCC AGA GCC (see SEQ ID NO:20) |
| VKELINKFOR | TGG AGA CTG GGT GAG AAC AAT TTG CGA TCC GCC ACC GCC AGA GCC (see SEQ ID NO:21) |
| VKFLINKFOR | TGG AGA CTG GGT GAG CAC ATT TTC CGA TCC GCC ACC GCC AGA GCC (see SEQ ID NO:22) |

SEQUENCE OF VH LINKER PRIMER.

| | | |
|---|---|---|
| LINK BACK | 5' GGG ACC ACG GTC ACC GTC TCC TCA 3' (see SEQ ID NO:23) | |
| PULL THROUGH PRIMERS | | |
| HBKAPA10 | 5' CAT GAC CAC AGT GCA CAG GTS MAR CTG CAG SAG TCW GG 3' (see SEQ ID NO:24) | |
| JK1NOT10 | 5' GAG TCA TTC TGC GGC CGC CCG TTT GAT TTC CAG CTT GGT GCC 3' (see SEQ ID NO:25) | |
| JK2NOT10 | 5' GAG TCA TTC TGC GGC CGC CCG TTT TAT TTC CAG CTT GGT CCC 3' (see SEQ ID NO:26) | |
| JK4NOT10 | 5' GAG TCA TTC TGC GGC CGC CCG TTT TAT TTC CAA CTT TGT CCC 3' (see SEQ ID NO:27) |
| JK5NOT10 | 5' GAG TCA TTC TGC GGC CGC CCG TTT CAG CTC CAG CTT GGT CCC 3' (see SEQ ID NO:28) |
| PCR SCREEN PRIMERS | | |
| KSJ28 | 5' GTC ATT GTC GGC GCA ACT ATC GGT ATC 3' (see SEQ ID NO:29) | |
| FDTSEQ1 | 5' GTC GTC TTT CCA GAC GTT AGT 3' (see SEQ ID NO:30) | |

Spleen mRNA was used from a mouse immunized with RT3-KLH (see Example 3) and cDNA was prepared using random hexamers (Pharmacia, Piscataway, N.J.) as primers. PCR reaction conditions are essentially as in McCafferty et al., Patent application WO 92/01047, using Taq polymerase according to manufacturers conditions.

The primary heavy chain product (VH) was made using the primer VH1FOR-2 and VH1BACK. The primary light chain PCR product (VL) was made in 5 separate reactions using an equimolar amount of the 4 MJKFONX primers with one of the 5 VKBACK primers (VKABACK, VKCBACK, VKDBACK, VKEBACK, VKFBACK). PCR conditions for VL's were 25 cycles of 94° C. for 1 minute, 55° C. for 1 minute and 72° C. for 2 minutes, followed by a 72° C. incubation for 10 minutes. For the VH's 60° C. was used as the hybridization temperature rather than 55° C. as this gave better results.

Linker fragments were prepared using the template pscFvNQ11 (McCafferty, J. et al., WO 92/01047) with the primer LINKBACK with 5 separate reactions each containing one of primers VKALINKFOR, VKCLINKFOR, VKDLINKFOR, VKELINKFOR, VKFLINKFOR.

Primary products were gel purified and linked together in 5 separate linkage reactions using linker fragments complementary with the 3' end of VH and with the 5' end of the various VL's. Linkage was done in a "mock" PCR reaction using the three fragments and no added primers. The linkage was carried out in duplicate in a 25 μl volume with approximately 10 ng of each fragment present. This linkage was taken through 25 temperature cycles of 94° C. for 1 minute, 60° C. for 2 minutes and 72° C. for 2 minutes followed by a 72° C. incubation for 10 minutes. 25 μl of assembly reaction was run on a gel and after de-staining the assembled product was just visible on the gel (data not shown)

The material for cloning was prepared in a secondary PCR reaction using primers which introduce cloning sites (VH1BACKAPA10 and a mix of JK1NOT10, JK2NOT10, JK4NOT10, JK5NOT10). A small amount of product from the linkage reaction was used as template (1 μl into a 50 μl PCR reaction). PCR conditions were 25 cycles of 94° C. for 1 minute, 55° C. for 1 minute and 72° C. for 2 minutes followed by a 72° C. incubation for 10 minutes.

The secondary PCR product was cut with the enzymes ApaL1/Not1, gel purified, cloned into the ApaL1 and Not1 sites of pCANTAB3his-6 and transformed into electrocompetent TG1 cells. (Transformation efficiencies were 5×10⁸/μg for pUC19 and 1×10⁶–10⁷/μg for ligated vector). A library of 1.2×10⁶ clones was generated and 18/20 clones were found to have insert. Analysis by PCR and BstN1 digestion indicate that these are all different.

EXAMPLE 4.3

Panning The Mouse Anti-RT3 Library Against RT3-BSA

The panning procedure was essentially as described in Marks, J. D. et al., *Biotechnology* 10 (1992):779–783. The RT3 hapten (compound 7, FIG. 1) was conjugated to BSA as described in example 2. Nunc (Kamstrup, Denmark) immunosorb tubes were coated with 1 ml of RT3-BSA at 20 mg/ml. The tubes were blocked to the top with 4 mls PBS/2% milk powder for 2 hours at 37° C. and 0.8–1.0 ml of concentrated phage (equivalent to 10–50 mls of culture supernatant) was used for binding. Tubes were not inverted. Binding of phage and washing was done using MOPS buffered saline (MBS which is 50 mM MOPS pH7.4, 150 mM NaCl).

Washing was done ten times with MBS/0.1% Tween 20 and ten times with MBS. Bound phage were eluted using 800 ml of 100 mM triethylamine, neutralized with 400 ml of 1M Tris pH 7.4 and infected into exponentially growing TG1-tr cells (T phage resistant TG1 cells). The cells infected with the eluate were plated onto large (22×22 cm) TY plates supplemented with 2% glucose/100 mg/ml ampicillin. Bacterial stocks were prepared next day, liquid cultures were inoculated from them and rescued with M13 helper phage and the panning procedure was repeated a second time with the concentrated phage.

The panning process was repeated and concentrated phage was used in a polyclonal ELISA. No signal was achieved from the unpanned library but increasing signal was achieved through successive pannings (not shown). The numbers of phage eluting after PAN 1, PAN2 and PAN3 increased each time as expected (0.12, 50 and 2200×10⁶ infectious phage respectively).

Eluted phage from PAN1 and PAN2 was introduced into HB2151 cells (a non-suppressor line producing soluble SCFv). Individual colonies were picked into 96 well plates containing TY medium with 100 mg/ml ampicillin supplemented with 2% glucose (TY/G/A) and grown for 4–16 hours (stock plate). These cultures were used to inoculate a second 96 well plate containing TY/A and 0.1% glucose. This plate was incubated for 2–4 hours at 30° C. before inducing by adding IPTG to 1 mM and growing overnight. Next day culture supernatants were added to ELISA plates previously coated with 2 mg/ml RT3-BSA and blocked with 2% milk powder. Binding was carried out in 1 X MBS/2% milk powder and binding was detected using the mouse 9E10 antibody followed by goat anti-mouse-peroxidase (Sigma, St. Louis, Mo.). The 9E10 antibody used to detect the myc tag peptide is available from the ATCC, Rockville, Md. (CRL1729, Name given is MYC1-9E10.2).

Screening for binding from PAN1 using RT3-BSA as antigen and MBS buffer throughout the procedure identified 47 positives from 364 clones. In a similar way, 115/184 positives were identified from PAN2. The diversity of the clones was analyzed by BstNI digestion of PCR amplified single chain DNA insert from each clone as described in Example 4.0.

The results are summarized in Table 1 on a group-by-group basis as shown below. 17 of 48 binders analysed from PAN1 (35%) had pattern A. A total of 78 binding clones from 115 from PAN 2 (68%) had PCR pattern A. (22 of these were restreaked and analyzed further and these are presented in Table 1). Pattern B was found in 2 of 48 (4.1%) clones from PAN1 and 24 of 115 (21%) from PAN2. 2 of 48 from PAN1 had pattern C (4.1%), while 3 of 115 from PAN 2 (2.6%) had this pattern. Pattern D was found in 3 of 48 clones from PAN1 (6.2%) and 3 of 115 from PAN 2 (2.6%). Thus, the proportion of positives from each group appears to alter from PAN1 to PAN2. This could result in the loss of potentially catalytic clones after several rounds of panning if selection is based solely on strength of binding to RT3.

TABLE 1

Grouping Of Mouse RT3 Binders According To PCR Pattern

| PCR Pattern | Sample No. |
|---|---|
| A | PAN1–3, 4, 6, 8, 9, 14, 17, 18, 24, 25, 27, 30, 35, 36, 45, 46, 47. |
|  | PAN2–60, 62, 63, 64, 65, 66, 67, 70, 72, 74, 77, 78, 79, 84, 85, 86, 87, 88, 91, 92, 96, 97. |
| B | PAN1–12, 20. |
|  | PAN2–49, 50, 51, 52, 53, 54, 55, 56, 57, 58, 59, 69, 82, 90, 93, 94, 99, 100, 101, 102, 103, 104, 105, 106. |
| C | PAN1–5, 48 |
|  | PAN2–75, 76, 80. |
| D | PAN1–10, 26, 43. |
|  | PAN2–68, 83, 89. |
| a | PAN1–2, 13. |
| e | PAN1–11, 19. |
| q | PAN1–7, 15. |
| i (small insert) | PAN1–23, 38, 44. |
| j (small insert) | PAN1–31, 40, 42. |
| E | PAN2–71, 73 |
| 10 unique patterns from PAN1 | b-21, d-41, f-1, g-33, h-16, k-28, I-39, n-34, p-32, G-22. |
| 4 unique patterns from PAN2 | F-61, H-81, I-95, J-98. |

At least 15 other patterns were found in PAN1 with many appearing only once. Many other patterns present in PAN1 were not identified in PAN2. In addition, some patterns appeared in PAN2 which had not been identified in PAN 1. This argues that there is much greater diversity in the library than is indicated by the PCR pattern groups which we have identified.

EXAMPLE 4.4

Binding Analysis of Selected Clones from Mouse RT3 Phage Antibody Library

Several mouse RT3 phage antibody clones isolated from PAN 2 (see Table 1, Example 4.3) were characterized further in terms of binding specificity. Analysis was done using a competitive inhibition format, in which the antibody is first reacted with free hapten or product or portions of hapten and product, prior to addition to RT3-BSA coated wells as described in detail below.

The clones selected for analysis and their corresponding PCR pattern (see Table 1, Example 4.3) were: 50 (PCR B), 64 (PCR A), 68 (PCR D), 71 (PCR E), 80 (PCR C), 84 (PCR A), 95 (PCR I), 96 (PCR A), and 97 (PCR A). Soluble scFv was purified from 50 ml cultures of each clone using the IMAC protocol described in Example 4.1, except bound antibody was eluted with 50 mM EDTA, 0.5M NaCl. The scFv concentration for each clone was estimated from silver stained SDS polyacrylamide gels by running a portion of the eluted protein on a gel containing appropriate scFv concentration standards. The scFv protein was diluted to 4 ug/ml and then serially diluted 1:2 across 11 wells of RT3-BSA coated ELISA plate. The concentration of scFv giving 50% of the maximum ELISA signal was determined from the titration. This concentration of scFv was used for a subsequent competitive inhibition assay described below.

Figure 2:
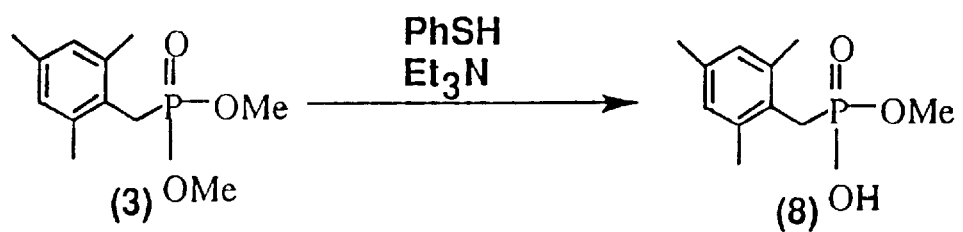

A competitive inhibition ELISA assay was performed by incubating scFV (at a concentration as determined by titration above) with 100 uM of each of the following compounds: RT3 hapten (Compound 7, FIG. 1), left hand portion of RT3 hapten (designated RT3A, Compound 8, FIG. 2), right hand portion of RT3 hapten (designated RT3B, Compound 12, FIG. 3), The left and right hand portions of the expected products from the esteriolytic cleavage of substrate (Compound 15, FIG. 4) designated Product A (Mesitylacetic acid, FIG. 4) and Product B (Compound 13, FIG. 4). The scFv was preincubated with the the inhibitor compound in tubes at room temperature for 1 hour prior to addition to RT3-BSA coated ELISA wells. The results of the assay are shown in FIG. 8. The $OD_{4415}$ nm readings have been normalized to a value of 1, which represents the ELISA signal seen for the corresponding scFv in the absence of added competitive inhibitor. The results show all of the clones with the exception of 68 and 71 are inhibited in their binding to RT3-BSA with free RT3 hapten. The clones which did not show inhibition with free RT3 were shown to have cross reactivity with BSA. Clones 64, 84, 96, 97 and 50 also show binding inhibition with RT3A and to a lesser extent with Product A. No inhibition is seen for any of the clones tested with RT3B or Product B.

EXAMPLE 4.5

Sequencing Of Mouse Anti-RT3 SCFv(s)

Although a large proportion of clones from PAN1 and PAN2 fall into the PCR A pattern group, it was not clear whether clones in this group were identical or diverse, and so a number of these clones were sequenced. Furthermore, in an attempt to determine whether the same heavy and light chains were being used within other major pattern groups, some representative clones from the other major groups were sequenced.

Single stranded DNA was prepared from those clones which are emboldened in Table 1 and sequencing was carried out using the Sequenase kit (USB, Cleveland, Ohio). Sequence alignments to Genbank germline sequences and between clones were done using the "MacVector™" (IBI, New Haven, Conn.) program. Since the sequences at the 5' and 3' ends were encoded and enforced by PCR primers, these were "removed" for alignments. In the presentation of light chain sequences, the primer encoded sequences are not shown but the primers which were used are indicated in the right hand column. For the heavy chains, since the 5' primer is a single but degenerate primer, the sequence introduced by this primer is shown in each case. For comparison, the actual heavy chain primer sequence is shown at the 5' and 3' ends of each clone. The sequence of one clone is presented on the top line and the differences from this sequence are indicated for the other clones. All PCR A mutations shown, which give rise to amino acid, changes were re-checked on the sequencing gels. For the heavy chains of pattern A, all unique changes were re-checked on the sequencing gel, and changes which occured in a number of clones were checked on at least one of the clones carrying that change.

Light Chain Sequences of Mouse RT3 Binders

As shown in FIG. 9, eight different light chains have been used with the 15 different clones from pattern A. The chain associated with clones mR6 and mR8, differs from the germline V gene by a single silent nucleotide change. The chain used in mR9, mR18 and mR27 differs from mR6 and mR8 by an additional single silent mutation. Thus, these 5 clones share the same protein sequence as the germline. Clones mR9 and mR27 have used different primers to derive the same sequence, indicating that they are independant isolates of this same sequence.

Clones mR3 and mR25 are identical in the sequence which has been amplified but have also used different primers from each other. The sequence which mR3 and mR25 share in common, differs from mR6 and mR8 by 2 silent nucleotide changes and 2 changes resulting in 2 amino acid changes in FR3 and CDR3. Most changes have occurred in the light chain shared by clones 14, 30, 36, 84, and 96. In these and in all the others light chains of this group, most amino acid changes are clustered in FR3, CDR3, and FR4.

One can envisage the basic germline clone represented in mR6/8 or mR9/25, changing S to N in CDR2 and then changing in 3 different ways to give the clones represented by 4, 97 and 14 (+4 others). Similarly, there may have been a change of Y to F in CDR 3 from the same starting point, giving rise to mR3 and mR25. A third series of changes may have given rise to mR24.

The light chain associated with pattern C (clone mR80) is also shown in FIG. 9 aligned with the germline sequence used in pattern A clones. The pattern C light chain appears to be a more highly mutated form, derived from the same germline as used in pattern A.

Clones representing the other PCR patterns appear to use different germline derived sequences. The relationship of these other clones to their nearest germline is shown in FIG. 10. In pattern B (50, 69), 2 nucleotide changes from germline give rise to 1 amino acid change. In pattern D (10, 43, and 68, and 83), 8 nucleotide changes from germline give rise to 5 amino acid changes. In pattern 1 (95), 2 nucleotide changes from germline give rise to 1 amino acid change.

FIG. 11 shows the relationship of the different light chain sequences to that of pattern A (for mR6, 8). There is a great deal of difference between them. For patterns D and I, only the protein sequence is shown, since the nucleotide sequences have many differences. The latter two groups have longer CDR2s than the others.

Heavy Chain Sequences of Mouse RT3 Binders

Analysis of the heavy chain sequences associated with PCR pattern A, reveals that, as for the light chain, they are all closely related but in most cases are different from each other (FIG. 12). The alignment to germline is less clear in these samples. The closest germline belongs to sub-group VH-II, but there are numerous differences from this germline, in the isolated clones. In addition, there appears to be a greater number of amino acid changes between clones. As expected the changes are clustered in the CDR(s).

The heavy chains of pattern B (FIG. 13), align to a different germline and again shows numerous changes from this. All 4 clones in this group appear to be identical. Thus it appears that the clones sequenced from pattern B are multiple isolates of the same antibody. The clones represented by pattern D are all identical to each other and, excluding the sequence of CDR3, differ from the closest germline by 4 amino acids (FIG. 13 ).

The alignment of all the different heavy chain patterns with that of pattern B is shown in FIG. 14. The heavy chains of pattern C (80) and pattern I (95) are closely related to that of pattern B. Pattern C differs by 4 amino acids. Pattern I differs by one silent mutation and one amino acid change. Interestingly, the heavy chain associated with patterns B, C, and I has a CDR of only 3 amino acids.

The amino acid change in mR95 appears to introduce an amber codon. This would introduce an amino acid at this position when the suppressor line TG1 is used in the preparation of phage, but would be expected to act as a stop codon, in the non-suppressor line HB2151 used in the screening of soluble antibodies.

Diversity of Clones In Pattern A

Table 2 collates the information derived from sequencing the clones in PCR pattern A. Each different light chain sequence in the group is given a label ai-aviii. Each different heavy chain sequence in the group is given a label Ai-Ax.

TABLE 2

Chain usage of mouse RT3 binders-PCR pattern A)

| HEAVY CHAINS | LIGHT CHAINS | | | | | | | |
|---|---|---|---|---|---|---|---|---|
| | ai | aii | aiii | aiv | av | avi | avii | aviii |
| Ai | | | | | | | | 14, 30, 36, 84, 96 |
| Aii | | 3 | | | | | | |
| Aiii | | | | 4 | | | | |
| Aiv | | | | 24 | | | | |
| Av | | | 9 | | | | | |
| Avi | 6, 8 | | | | | | | |
| Avii | | | | | | 64 | | |
| Aviii | | | | | | | | 97 |
| Aix | | 27 | | | | | | |
| Ax | | | 25 | | | | | |

Clones 14, 30, 36 (PAN1) 84, 96 (PAN) 2 are identical and probably represent duplicate isolates of the same initial clone. Clones 6 and 8 are also identical to each other. Otherwise, every clone is different. There are two cases where the same light chain has been used with two different heavy chains (aii in mR 9/mR27 and aiii in mR3 and mR25). As described earlier, the light chains in each pairing used different primers. Apart from the duplicate isolates, there are no cases here, of the same heavy chain being used in different clones.

These PCR and sequencing experiments suggest that there is indeed a great diversity in the mouse library both at the gross scale, as judged by PCR analysis, and at a more subtle level, as judged by sequencing.

EXAMPLE 5.1

Screening of scFv Molecules for Catalytic Activity

1. Initial Selection

An early screen protocol was used to rapidly select a subset of potentially catalytic scFv molecules from the large number of scFv fragments that had been selected on the basis of hapten affinity.

a) Immobilization: The scFv fragments that bound to hapten in an ELISA assay were selected for screening to detect catalytic activity. A 96-well Millititer GV filtration plate (Millipore) was pre-wetted and washed in PBS containing 0.05% Tween-20. Suspensions of scFv fragments immobilized on anti-myc antibody Protein A agarose (vide infra, also see Example 6.1) were each transferred to separate wells in the 96 well filter plate. Residual supernatant was removed by aspiration through the filter plate. The immobilized scFv fragments were washed in the wells by filtration at 4° C. with PBS/Tween (5×200 μL), PBS (3×200 μL), and 25 mM HEPES, pH 7.0, 140 mM NaCl, 0.01% NaN3 (3×200 μL).

b) Incubation of scFv and substrate: To immobilized washed antibody was added 200 μl of approximately 50 μM RT3 substrate (Compound 15, FIG. 4) in 25 mM Hepes, pH 7.0,140 mM NaCl, 0.01% NaN$_3$ was added. Following incubation at room temperature (approximately 22° C.) for approximately 24 hours after which substrate solution (but not beads) was withdrawn and frozen (−20° C.) until analyzed by high performance liquid chromatography (HPLC). The same 96 well plate, still containing immobilized scFv, was washed with 4×200 μL/well with 10 mM Tris, pH 9.0, 140 mM NaCl, 0.01% NaN$_3$. Again, 200 μL of 35–50 μM of RT3 substrate (Compound 15, FIG. 4) was added, this time in the pH 9.0 buffer described above. The scFv fragments were incubated with compound 1 for 3 hours and, as at pH 7.0, substrate solution was withdrawn frozen for later analysis of product formation.

c) Analysis of Reaction Mixtures for Product Formation: To reduce the number of samples, pools of generally two or three reaction mixtures (50 μL of each reaction mixture) were subjected to HPLC analysis. Mixtures (100 or 150 μL) were centrifuged in an Eppendorf centrifuge to prevent any carry-over of the agarose onto the HPLC system. Samples were then injected onto a Waters HPLC system equipped with a Vydac C-18 analytical reverse phase column. Components of the eluent were separated using a linear gradient over 30 minutes from 0.1% TFA in water to 0.1% TFA in acetonitrile. Product was detected and quantitated spectrophotometrically using a Waters spectral detection system, typically set at 215 or 270 nm.

Early screen analysis of 46 hapten-binding scFv fragments was carried out at pH 7.0 and 9.0 to detect catalytic activity. HPLC analysis was carried out and peak areas determined for those sample pools which gave a peak at the expected retention time for the product. The results are summarized in Table 3 below. HPLC analyses of the reaction mixtures (as pools of 2 or 3) indicated that at pH 7.0, one pool of three samples and one pool of two samples appeared to have substantial product formation. At pH 9.0 a number of pools showed product peak areas above background. Three pools of three samples showed large product peaks with peak areas greater than 0.6 and these were scored as being positive. Thus, early screen assays narrowed the number of potentially catalytic scFv fragments from 46 to 5 at pH 7.0 and from 46 to 9 at pH 9.0. Three of the candidates at pH 7.0 were the same scFv fragments as three of the candidates at pH 9.0.

TABLE 3

HPLC Assay Results of Early Screen Phage Antibody Pools at pH 7.0 and 9.0

| SAMPLE | PEAK AREA |
|---|---|
| ph 7.0 | |
| BLANK | .18 |
| 1, 2, 3 | — |
| 4, 5, 6 | — |
| 8, 11, 12 | — |
| 14, 16, 17 | — |
| 18, 19, 20 | 0.52 |
| 21, 24, 25 | — |
| 27, 28, 29 | — |
| 30, 31, 32 | — |
| 33, 34, 35 | — |
| 36, 37, 38 | — |
| 39, 40, 41 | — |
| 42, 44, 45 | 0.455 |
| 46, 47, 48 | 0.476 |

TABLE 3-continued

HPLC Assay Results of Early Screen Phage Antibody Pools at pH 7.0 and 9.0

| SAMPLE | PEAK AREA |
|---|---|
| 50, 65, 76 | 0.559 |
| 83, 97 | 0.571 |
| ph 9.0 | |
| BLANK | — |
| 1, 2, 3 | 0.572 |
| 4, 5, 6 | — |
| 8, 11, 12 | 0.674 |
| 14, 16, 17 | 0.581 |
| 18, 19, 20 | 0.79 |
| 21, 24, 25 | 0.522 |
| 27, 28, 29 | 0.504 |
| 30, 31, 32 | 0.627 |
| 33, 34, 35 | 0.496 |
| 36, 37, 38 | 0.492 |
| 39, 40, 41 | 0.492 |
| 42, 44, 45 | 0.470 |
| 46, 47, 48 | 0.471 |
| 50, 65, 76 | 0.511 |
| 83, 97 | 0.407 |

Individual clones from each of the active pools identified as above were reassayed for catalytic activity. Since the scFv remains bound to the anti-Myc agarose the same material used for the pool assays was reused for the assay of the individual clones. The results of the catalytic assays are shown in Table 4 below. The catalytic assay identified 6 clones: 11, 12, 18, 19, 30, and 83, which gave a product peak on HPLC. Clone 83 was active at pH 7.0, but not pH 9.0. Clones 18 and 19 were active at both pH 7.0 and 9.0. Clones 11, 12, and 30 were active only at pH 9.0.

TABLE 4

HPLC Assay Results of Individual Page Ab Clones at pH 7.0 and 9.0

| SAMPLE | PEAK AREA |
|---|---|
| pH 7.0 | |
| 18, 19 | 0.556 |
| 83 | 2.04 |
| 97 | — |
| ph 9.0 | |
| 8 | — |
| 11 | 1.5 |
| 12 | 1.21 |
| 18 | 1.09 |
| 19 | — |
| 30 | 0.96 |
| 31 | – |
| 32 | – |

EXAMPLE 5.2

1. Secondary Screening for Catalytic Activity

To further examine the scFv fragments for catalytic activity, the potentially-catalytic proteins identified in the early screen described above were individually grown and purified. Purification of the scFv was acheived as described in Example 6.1 using either IMAC or affinity chromotagraphy on anti-Myc-Protein A agarose. Assays were performed in the same buffer systems and pH values as in the early screen but the antibodies were tested individually and they were not immobilized but free in solution.

From these secondary assays, two scFv molecules, designated 18 and 83, catalytic activity was found. Clone 18 appeared to be active at pH 9.0 but not at pH 7.0 while clone 83 appeared to be active at pH 7.0 but not at pH 9.0 or 5.0. Both activities were significantly inhibited by the RT3 phosphonate transition state analog hapten (Compound 7, FIG. 1) when 10 μM antibody was assayed with 40 μM substrate and 30 μM hapten. These two clones were selected as candidates for large scale purifcation of scFv as described below. The results of these assays are presented in Example 6.4.

EXAMPLE 6.1

Large Scale Purification of scFv from Catalytic mRT3 Phage Antibody Clones 18 and 83

Preparation of Periplasmic Lysates-E. coli HB2151 clones expressing soluble anti-RT3 scFv were grown overnight in 2XYT containing 2% Glucose and 100 ug/ml ampicillin. Overnight cultures were used to inoculate 500 ml of 2XYT at a starting OD600 of 0.1 and cultures were shaken at 28° C. for 3 to 5 hours until OD600 of 1.2 to 1.8. IPTG was added to 1 mM final concentration and shaking incubation was continued at 25° C. for 2.5 hours. Cells were pelleted at 4,000 XG for 10 minutes and pellets were resuspended in 6 ml of periplasmic lysate buffer (10 mM phosphate buffer, 1M NaCl, 1 mM EDTA, pH 7.5. Following incubation on ice for 30 minutes, lysates were centrifuged at 6,000 XG to remove cellular debris. PMSF was added to the cleared lysate at a final concentration of 5 μg/ml and lysate was stored on ice until purification as described below.
Immobilized Metal Affinity Chromotagraphy (IMAC)

$MgCl_2$ was added to the periplasmic lysate to 1 mM final concentration and lysate was passed through a 1 ml bed volume $Ni^{+2}$ charged sepharose column (Probond Metal binding Resin, Invitrogen Corp., San Diego, Calif.) washed and equilibrated with 10 mM phosphate buffer,1M NaCl. Column was washed with 10 bed volumes of 10 mM phosphate, 1M NaCl, pH 7.5 and bound scFv was eluted with 50 mM EDTA, 0.5M NaCl. Column eluate was concentrated and dialyzed into 7 mM phosphate buffer, 0.15M NaCl, pH 8.0 using a Centricon 10 microconcentrator (Amicon, Beverly, Mass.) following manufacturers instructions. (see Mol. Cell. Biol. 5 (1985):3610–3616). For some preperations of scFv concentration of the IMAC eluate was not required.

Anti-myc Peptide Affinity Purification—Monoclonal antibody 9E10 that recognizes a 13 amino acid peptide tag at the C-terminus of the scFV was cross-linked to Protein A agarose using an Affinica Antibody Orientation Kit (Schleicher and Schull, Keene, N.H.) following manufacturers instructions. A 1 ml bed volume column was pre-washed with 0.23M Glycine, 0.3M NaCl, pH 2.5 and reequilibrated with 10 mM Phosphate buffer, 0.5M NaCl, pH 7.5. Periplasmic lysates were diluted with an equal volume of 10 mM phosphate buffer, pH7.5 and then passed through column. Column was washed with 10 bed volumes of 10 mM phosphate buffer, 0.5M NaCl and bound scFv was eluted with 0.23M glycine, pH25, 0.3M NaCl. For some preparations the column eluate was dialyzed and concentrated using a Centricon 10 microconcentrator as described above.

EXAMPLE 6.2

Purification Of ScFv Fragments from Phage Antibody Catalytic Clones 18 and 83 By Hydrophobic Interaction Chromatography Following IMAC or anti-myc peptide Protein A agarose purification of scFv derived from lysates of E. coli clones 18 and 83 (see Example 6.1), further purification of the scFv was accomplished on an alkyl superose 5/5 column attached to an FPLC system (Pharmacia).

Chromatography was performed using a linear reverse gradient of $(NH_4)2SO_4$ in 0.1 M Na phosphate pH 7.0. This was formed from two buffers:

Buffer A: 2M $(NH_4)_2SO_4$ in 0.1M Na phosphate pH 7.0
Buffer B: 0.1M Na phosphate pH 7.0
Gradient conditions were:
0–3 ml: 10% Buffer B
3–39 ml: Linear gradient, 10%–70% Buffer B
39–42 ml: Linear gradient, 70%–100% Buffer B
42–44 ml: 100% Buffer B
44–46 ml: Linear gradient, 100%–10% Buffer B
46–49 ml: 10% Buffer B Samples were adjusted to a final concentration of 1.8M $(NH_4)_2SO_4$ by the addition of 0.783 vols of a saturated solution of $(NH_4)2SO4$ in 0.1M Na phosphate (4.1M $(NH_4)_2SO_4$) and dilution with an appropriate volume of 10% Buffer B: 90% Buffer A to increase the volume to a value suitable for injection onto the column. Fractions were collected and the peak(s) corresponding to ScFv identified by SDS PAGE as described below. These were pooled, concentrated and used in assays for binding or catalytic activity as appropriate. Elution of protein from the column was monitored by $OD_{280}$ and plotted automatically. A typical chromatogram for IMAC pure scFv from clone 18 shows the bulk of the protein elutes in two distinct peaks. Fractions corresponding to each of the peaks were pooled as indicated. Peak 1 consisits of a broad shoulder eluting at 17.25 to 21.90% Buffer B (Pool 1) followed by a sharp peak at 24.2% Buffer B (Pool 2). Peak 2 is a sharp peak eluting at 48.10% buffer B (Pool 3). Purification of the scFv was monitored by silver stained SDS/PAGE with the following results. Load material for the HIC column (IMAC pure scFv +$(NH_4)_2SO_4$) showed>90% of the protein was scFv. At least four additional bands were also visible. Analysis of Pool 1 and Pool 2 obtained following HIC showed the majority of the scFv that was loaded was distributed equally in these pools and no substantial purification of the scFv was acheived. Pool 3 contained a small amount of scFv and an additional low molecular weight band.

The chromatogram for clone 83 shows the bulk of the scFv protein elutes in a single sharp peak at 54.7% Buffer B. A second minor peak of protein elutes during the final wash with 100% Buffer B. Fractions corresponding to these peaks were pooled and analyzed by SDS/PAGE followed by silver staining. The column load material for HIC (IMAC purified material+$(NH_4)_2SO_4$) contained>90% scFv. After HIC the majority of the scFv is recovered in the single main peak eluting at 54.7% Buffer B. As with clone 18, no substantial purification of the scFv was acheived by HIC. A small amount of scFv is found in the late eluting minor peak.

EXAMPLE 6.3

Binding Assays of IMAC and HIC Pure scFv from Phage Antibody Catalytic Clones 18 and 83

Fractions or pools of fractions from the purification protocols described above (see Example 6.1 or 6.2) were analyzed for RT3 binding activity using an RT3-BSA solid phase ELISA assay essentially as described in example 4.4. The fraction or fraction pools were first diluted 1:5 or 1:10 in PBS/Tween-20 and then serially diluted 1:2 with PBS/Tween-20 across 11 wells of the RT3-BSA coated ELISA plate. The titer which gave the 50% maximal ELISA signal was determined for each sample analyzed. By multiplying this titer by the volume of the pool or fraction analyzed, an estimate of the number of binding units in each sample could be determined. This analysis showed that for clone 83 even though majority of the scFv loaded on the HIC column was recovered it had less than 10% of the binding activity compared to the column load. This result suggests that HIC may be unsuitable for purification of the scFv, since it may result in perturbations of the scFv protein structure resulting in loss of binding and presumably catalytic activity.

EXAMPLE 6.4

Catalytic Assays of IMAC and HIC Purified scFv from Phage Antibody Clones 18 and 83

For clone 18 a typical catalytic assay was set up as follows: 50 μl of scFv was added to 145 μl of RT3 substrate (Compound 15, FIG. 4) and 5 μl of water or for some assays 5 μl of RT3 hapten. A blank consisting of 50 μl of water and 147 μl of RT3 substrate was set up to monitor the background hydrolysis of the RT3 substrate. The reaction was allowed to proceed for 6 hours after which samples were frozen at −20° C. to stop the reaction. Samples were analyzed by HPLC as described in example 5.1. The amount of scFv added to an assay typically ranged from 1 to 5 ug and protein was buffered in 10 mM Hepes, 150 mM NaCl, pH 7.3. The typical RT3 substrate concentration was 50 uM buffered in 25 mM Tris-Cl, pH 9.0, 140 mM NacL and 0.01% $NaN_3$.

An HPLC profile showing a typical positive catalytic assay result for IMAC pure 18 scFv is shown in FIG. 15A. FIG. 15B shows the HPLC profile of the same assay but done in the presence of RT3 hapten (Compound 5, FIG. 1). Finally, FIG. 15C shows the HPLC profile of the blank (no added scFv).

In a similar manner assays of the fraction pools obtained following MC purification of 18 scFv (see Example 6.2) were also performed. A typical result for the assay of the main scFv-containing pool (Pool 2 as described in Example 6.2 above) is shown in FIG. 16. Similar results were obtained from assays of Pool 1 and Pool 3 (data not shown).

Assay of IMAC or HIC purified scFv from clone 83 was done in a similar manner as described for clone 18 with the following exceptions. Substrate was buffered in 25 mM HEPES, pH 7.0, 140 mM NaCl and 0.01% $NaN_3$. Due to the lower background hydrolysis of RT3 substrate at neutral pH, reactions were typically run for 24 hours. An HPLC profile of a positive catalytic assay result for IMAC pure 83 scFv is shown in FIG. 17A. The same assay repeated in the presence of RT3 hapten is shown in FIG. 17B. A blank was also analyzed and gives a profile similar to the that in FIG. 17B (data not shown). A catalytic assay of the main scFv containing pool obtained following HIC (see Example 6.2) is shown in FIG. 18.

It should be noted that the retention times of the expected product peak as well as non-product related peaks varied from run to run on the HPLC. The reason for this variation is not known. Test runs of the RT3 product (Compound 13, FIG. 4) alone on HPLC and monitoring at 215 nM showed a distinct peak profile was produced. This 215 nM profile was used as an internal control to accurately determine the position of the product peak on the 270 nM profile for each HPLC run.

Conclusions from the results of the catalytic assays performed as described above are as follows. IMAC pure scFv from both clone 18 and 83 is able to hydrolyze the RT3 substrate and produces a product peak that elutes from the HPLC column at the correct retention time. In the presence of RT3 hapten, catalysis is completely abrogated presumably due to the much tighter binding of the RT3 hapten in the antibody pocket compared to the RT3 substrate. This is further evidence that the scFv is responsible for catalysis since it is unlikely that natural esterase exists which is capable of specifically recognizing and binding the RT3 substrate or hapten with high affinity.

Following HIC purification of scFv for either clone 18 or 83 no catalytic activity was observed in the scFv containing fractions. Loss of activity could possibly be due to instability of the scFv resulting in unfolding or aggregation. Instability of the scFv for clone 83 was clearly demonstrated by the loss of binding in the assays performed on HIC purified scFv as described in Example 6.3

EXAMPLE 7.1

Isolation of Binders to the Transition State Analogue, RT3 from a Naive Human Library It has been demonstrated that immunization schemes can be by-passed and that low and moderate affinity human antibodies (Kds down to 86 nM) can be isolated directly from human antibody libraries derived from non-immunized sources (Marks et al., *J. Mol. Biol.* 222 (1991):581–597). This approach could provide a starting clone (or clones) which could be improved by a number of approaches as described by example below (for related examples see Marks et al., *BioTechnology* 10 (1992):779–783). These approaches could, therefore, lead to the isolation of entirely human catalytic antibodies which could prove extremely valuable, particularly in the area of therapeutic catalytic antibodies.

The non-immunized human library described in Marks et al., *J. Mol. Biol.* 222 (1991):581–597, was panned against RT3-BSA, coated onto tubes as described for the immunized mouse library except 100–200 μg/ml RT3-BSA coating concentration was used. The progress of the purification schemes was monitored by ELISA(s) using polyclonal phage. Polyclonal phage derived from 2 rounds of panning against RT3-BSA (RT3BSA:2) gives a signal which is visible after overnight incubation with substrate. Polyclonal phage derived from 3 rounds of panning against RT3-BSA (RT3BSA:3) gives a strong signal on ELISA (1 O.D. in 5 minutes). No binding to BSA was observed and binding to RT3-BSA was inhibited by pre-incubation with 10–100 μg/ml of soluble, unconjugated RT3 suggesting that it was specific for RT3 (not shown).

Individual clones derived from 3 and 4 rounds of panning were examined for binding using methods as described in example 4.3. Before beginning to screen on a large scale, the minimum ELISA coating concentration was determined. Reducing antigen concentration from 100 μg/ml to 1.6 μg/ml (100 μl/well) causes only a 30% reduction in signal (data not shown) 2 μg/ml concentration was, therefore, used in all subsequent ELISA screenings 144 clones derived from 3 rounds of panning were examined by ELISA assay for specific binding to RT3-BSA using 100 μl of culture supernatant from IPTG induced HB2151 clones. As shown in FIG. 19A, 40 clones gave strong ELISA signals (0.7 to 2.5 O.D. after overnight incubation with substrate) and 27 gave moderate signals (0.2–0.5 O.D. after overnight incubation with substrate). FIG. 19B shows the results for 48 clones derived from 4 rounds of panning against RT3-BSA. From this 39 clones showed strong ELISA signal (0.7–2.5 O.D.) and 1 moderate ELISA signal (0.34 O.D.).

PCR analysis and Bst N1 digestion revealed that all the the good binders examined from both rounds of panning shared a common PCR pattern and all but one of the weaker binders examined shared a common PCR pattern which is different to that of the high binders. One additional pattern was found associated with one of the weak binders. It is interesting to see enrichment with successive rounds of panning of the clone associated with high ELISA signal relative to that for moderate signal, as previously described by Clackson et al., Nature 352 (1991):624–628.

EXAMPLE 7.2

Sequence Analysis of Human RT3 Binders

Sequencing was carried out on various members of each PCR pattern group as shown below:

PCR1 = RT3:1, 4, 5, 41, 63, 80.
PCR2 = RT3:47, 54
PCR3 = RT3:61 nucleotide and deduced amino acid sequences of each group FIG. 20.

EXAMPLE 8.1

Chain Shuffling of Human RT3 Binders

The scheme used for chain shuffling is shown in FIG. 21. All of the scFv clones in the human or mouse libraries share certain common sequences including the plasmid sequences upstream of the heavy chain, the linker sequences between the heavy and light chains and gene 3 sequences downstream of the light chain. Primers were selected/synthesized from these areas to provide a general means of ampifying cloned heavy or light chain V regions. Thus, PCR using the primers LMB3 and PCRHLINK will give rise to a heavy chain product while the primers FDTSEQ1 and LINKPCRL will give rise to a light chain product. LINKPCRL and PCRHLINK are complementary and so provide a means of linking the products. In this way, the separate heavy or light chains from each clone can be linked to a whole population of complementary chains derived from the initial library. The linked product acts as a template for a secondary PCR using the primers LMB3 and FDTSEQ1 and the secondary product is digested with Sfi1 and Not1 for cloning. The primers were chosen to enable a change in fragment size to be observed following each digestion step. In addition, the efficiency of digestion is probably improved by having a relatively large overhang upstream of the restriction site.

Method for Chain Shuffling

The following primers are used:

| FDTSEQ1 | 5' GTC | GTC | TTT | CCA | GAC | GTT | AGT 3' (see SEQ ID NO:30, also appearing at page 34, line 43) |
| LMB3 | 5' CAG | GAA | ACA | GCT | ATC | AC 3' (see SEQ ID NO:31) | |
| PCRHLINK | 5' ACC | GCC | AGA | GCC | ACC | TCC | GCC 3' (see SEQ ID NO:32) |
| LINKPCRL | 5' GGC | GGA | GGT | GGC | TCT | GGC | GGT 3' (see SEQ ID NO:33) |

Primary heavy and light chain PCR products are prepared in the following reactions:

| HEAVY | | LIGHT | |
|---|---|---|---|
| LMB3 primer (10 pmoles/ml) | 2.5 μl | FDTSEQ1 primer (10 pmoles/ml) | 2.5 μl |
| PCRHLINK Primer (10 pmoles/ml) | 2.5 μl | LINKPCRL primer (10 pmoles/ml) | 2.5 μl |
| 10× PCR reaction buffer | 5.0 μl | 10× PCR reaction buffer | 5.0 μl |
| 5 mM each dNTP's | 2.5 μl | 5 mM each dNTP's | 2.5 μl |
| Taq polymerase (5 U/ml) | 0.3 μl | Taq polymerase (5 U/ml) | 0.3 μl |
| water | 37 μl | water | 37 μl |

PCR conditions are 25 cycles of 94° C. 1 minute, 60° C. 1 minute, 72° C. 2 minutes with a final 10 minutes at 72° C. For isolated clones template can be most simply provided as a toothpick innoculum from a bacterial colony. For library material, DNA was prepared from a frozen bacterial stock and 2–10 ng added to the reaction. Primary PCR products were purified on agarose gels and purified using 5 μl of Geneclean "glass milk" (Bio 101, La Jolla, Calif.) with two elutions in water of 10 μl each.

Assembly is carried out as follows:

| purified heavy | 2.5 μl (20–50 ng) |
| purified light | 2.5 μl (20–50 ng) |
| 10× reaction buffer | 2 μl |
| 5 mM each dNTP(s) | 1.0 μl |
| Taq polymerase | 0.2 μl |
| water | 37 μl |

PCR conditions are 25 cycles of 94° C. 1 minute, 65° C. for 4 minutes with a final 10 minutes at 72° C.

For secondary PCRs, 1 μl of the linked material was used as template. The reaction was set-up as follows:

| linked PCR product | 1 μl |
| LMB3 primer (10 pmoles/ml) | 2.5 μl |
| FDTSEQ1 primer (109 pmoles/ml) | 2.5 μl |
| 10× PCR reaction buffer | 5.0 μl |
| 5mM each dNTP(s) | 2.5 μl |
| Taq polmerase (5 U/ml) | 0.3 μl |
| water | 37 μl |

PCR conditions are 25 cycles of 94° C. 1 minute, 60° C. 1 minute, 72° C. 2 minutes with a final 10 minutes at 72° C. (5 μl can easily be seen on a gel).

The secondary product was extracted with phenol:chloroform and precipitated with ethanol, to remove Taq polymerase. The PCR product was digested overnight at 50° C. with Sfi1 according to manufacturers instructions. Next day 1/10th volume of 1M NaCl was added to give a final concentration of 150 mM NaCl and Triton-X100 added to a final concentration of 0.01% before digesting with Not1 for 3 hours at 37° C. The digest was treated with phenol:chloroform, precipitated, dissolved in $H_2O$ and purified by running on a 1.5% agarose gel and purified with "Geneclean"(Bio 101, La Jolla, Calif.). The DNA was eluted into a final volume of 10–15 µl and cloned into the Sfi1/Not1 site of pCANTAB5 his-6.

Plasmid DNA of pCANTAB5 his-6 was prepared by the alkaline lysis method and was purified by cesium chloride centrifugation. The purified DNA was digested at a DNA concentration of 100 µg/ml with Sfi1 according to manufacturers instructions (50° C. for Sfi1, overnight ) followed by a 3 hour digestion with Not1. The digestion product was loaded on directly on to a Chromaspin 1000 column ( Clontech, Palo Alto, Calif.) to remove the stuffer fragment and spun for 3 minutes at 2200 rpm in a bench top centrifuge. The DNA was then phenol:chloroform extracted and dissolved at 100 µg/ml for use.

Ligations are carried out using an Amersham (Arlington Heights, Ill.) ligation kit as follows:

| | |
|---|---|
| Vector DNA | 1 µl (100 ng) |
| insert DNA | 2 µl (10–50 ng) |
| 10 mM MgCl, | 3 µl |
| 200 mM Tris pH 7.4 | 3 µl |
| buffer A | 24 µl |
| buffer B | 6 µl |

Incubate for 30–60 minutes at 16° C. For library preparation, 5 times the volumes shown above were used. The ligation product was concentrated and purified using Geneclean and eluted into a volume of 10–15 µl of water. This was introduced into electrocompetent T phage resistant TG1 cells using a Bio-Rad (Hercules, Calif.) electroporator, according to manufacturers instructions.

Three clones, hRT3-1, hRT3-47, and hRT3-61 isolated after four rounds of panning of the naive human library (see Example 5.1) were used as templates for the chain shuffling protcol described above. As described in Example 5.2, sequence analysis showed each of the three clones were unique from each other in terms of VH and VL gene usage. Six different libraries were prepared. In each case, the name of the library refers to the fixed chain and the clone number from which it was derived. Thus, H47 is a library with a fixed heavy chain from RT3:47 combined with a library of human light chains.

The library sizes obtained were as follows:

TABLE 3

| Library | Size (x 10⁶) | Proportion with insert |
|---|---|---|
| H1 | 7.8 | 9/10 |
| H47 | 6.2 | 8/10 |
| H61 | 6.8 | 9/10 |
| L1 | 9.6 | 9/10 |
| L47 | 9.8 | 9/10 |
| L61 | 8.4 | 8/10 |

PCR using the primers FDTSEQ1 and LMB3 was carried out on 10 co.lonies from each library to determine the proportion with insert. The results are shown in the table above. In addition the PCR products were digested with BstN1 to determine the diversity. It should be remembered, however, that approximately ⅔ of the sequence (of any given clone) in the chain shuffled library, is now fixed and that different members of the same V gene family may give the same "BstN1 signature". Despite this, none of the library members had the pattern associated with the original clone. In some cases, patterns were found in duplicate within some libraries and one pattern may have appeared 3 times in the H1 library.

EXAMPLE 8.2

Panning Human Chain Shuffled Library

Phage particles were rescued from the libraries as described in Marks et. al., *Biotechnology* 10 (1992) :779–783. Phage from pairs of libraries derived from the same starting clone were pooled and panned against RT3-BSA (e.g., H1 and L1). Panning and rescue were done essentially as described in Marks et al., *J. Mol. Biol.* 222 (1991):581–597). except Nunc (Kamstrup, Denmark) immunosorb tubes were coated overnight with 1 ml of RT3-BSA at 20 µg/ml. Coating and blocking were done in phosphate buffered saline (PBS) as before. The equivalent of 20 mls of phage was used in a final volume of 800 µl of MOPS buffered saline (MBS) with 2% dried milk powder. Washing, elution, infection, and rescue with M13 helper phage were as described above. "Polyclonal" phage derived from either the unpanned libraries (PAN0), from the first round of panning (PAN1), or from 2 rounds of panning (PAN2) were used in an ELISA to determine the progress of the panning process for each pair of libraries.

As shown in FIG. 18, no signal was observed from PAN0 samples. Low level signal is observed in PAN1 samples derived from RT3:1 and RT3:47 and there is a marked improvement in PAN2 samples. With libraries derived from RT3:61, ELISA signal is still relatively low after two rounds of panning. The ELISA results are mirrored when the eluate from each round of panning is quantitated as shown in Table 4. Increasing numbers of phage are eluted from the second panning. The numbers of phage yielded from PAN1 and PAN2 on the H61/L61 libraries is lower than the corresponding yield from H1/L1 and H47/L47 libraries.

TABLE 4

Yield of phage from pannings (x 10⁶)

| | shuffled RT3:1 | shuffled RT3:47 | shuffled RT3:61 |
|---|---|---|---|
| eluate of PAN1 | 1.4 | 2.9 | 0.34 |
| eluate of PAN2 | 1300 | 1600 | 200 | input phage approximately 2–10 x 1012

Table 5 shows the proportion of positives derived from panning the reshuffled human binders. For reshuffled RT3:1 and RT3:47, even after one round of panning the majority scored positive. Since polyclonal phage from reshuffled RT3:61 was negative after PAN1, and positive after PAN2, individual colonies were only analyzed from PAN2 from this library.

TABLE 5

Proportion Of Positives From Reshuffled Human Libraries

| POPULATION | PROPORTION POSITIVE | NUMBERS RESTREAKED |
|---|---|---|
| RT3:1 Reshuffle | | |
| PAN1 | 39/44 | 28 |
| PAN2 | 42/44 | 15 |
| RT3:47 Reshuffle | | |
| PAN1 | 29/44 | 25 |
| PAN2 | 35/48 | 28 |
| RT3:61 Reshuffle PAN2 | 44/96 | 37 |

Positive clones were restreaked and retested for RT3 and BSA binding. All reshuffled human libraries gave rise to a high proportion of binders after 1–2 rounds of panning. These have been grouped by PCR/BstN1 digestion (using FTDSEQ1 and LMB3) into 9 PCR pattern groups for the RT3:1 reshuffled library, 4 PCR pattern groups for the RT3:47 reshuffled library and 8 PCR pattern groups for the RT3:61 reshuffled library as shown in Table 6 below.

There is a strong possibility that a heavy chain shuffled, with a library of light chains, will pull out different light chains, which are related to each other, and so the potential for PCR pattern diversity is reduced. Conversely, it is likely that a degree of diversity will be found by sequencing, even within a given PCR grouping.

TABLE 6

Grouping Of Human RT3 Binders According To PCR

PCR Pattern    Sample No.

A. RESHUFFLED CLONES ARISING FROM HU RT3:1

| | |
|---|---|
| A | PAN1–1, 5, 6, 9, [10], 12, 21, 27. |
|   | PAN2–31, 34, 35, 36, [38], 41, 42, 43. |
| B | PAN1–2, 3, 4, 8, 11, 13, 22, 24 [25]. |
|   | PAN2–30, 39. |
| C | PAN1–[7], 14, [15], [19], 23. |
|   | PAN2–29, 33. |
| D | PAN1–17, [18], [26]. |
|   | PAN2–[44]. |
| E | PAN2–32, 40. |
| F | PAN1–[20]. |
| G | PAN1–28. |
| H | PAN1–16. |
| I | PAN1–37. |

3/ All samples from RT3:1 were negative for BSA binding apart from a very low level in sa

B. RESHUFFLED CLONE ARISING FROM HU RT3:47

| | |
|---|---|
| A | PAN1–2, 4, 12, 17, 20, 21, 22. |
|   | PAN2–4, 5, 6, 7, 27, 28, 29, 31, 33, 40, 41, 42, 44, 48, 49, 51, 52, 53. |
| B | PAN1–9, 10. |
| C | PAN1–1. |
|   | PAN2–37. |
| D | PAN1–3, [26]. |
| Pattern | Negative on re-screening |
| Unknown | PAN1–13, 14, 15, 16, 18, 19, 23, 24, 25. |
|   | PAN2–30, 32, 34, 35, 36, 38, 39, 43, 45, 46, 47, 50. |
|   | Binder to BSA |
|   | PAN1–11 |

C. RESHUFFLED CLONE ARISING FROM HU RT3:61

| | |
|---|---|
| A | PAN2–2, 8, 10, 11, 13, 14, 15, 17, 18, 20, 21, 23, 24, 25, 26, 28, 29, 32, 34, 35. |
| B | PAN2–16, 30, 33. |
| C | PAN2–4. |
| D | PAN2–6. |
| E | PAN2–12. |
| F | PAN2–9. |
| G | PAN2–22. |
| H | PAN2–31. |
| Pattern | Negative on re-screening. |
| Unknown | PAN2–1, 3, 5, 27, 36, 37. |
|   | Positive on re-screening. |
|   | PAN2–7. |
|   | Binder to BSA. |
|   | PAN2–19. |

Footnote:
1/ Samples are all labelled hu(original clone number):reshuffled clone number e.g. hu47:12 human clone derived from chain shuffling clone RT3:47 from the first panning and numbering derivative 12. For presentation here, only the clone number is given.
2/ The use of the same letters for pattern groups derived from different starting clones, is not meant to imply that they are the same.

TABLE 6-continued

Grouping Of Human RT3 Binders According To PCR

PCR Pattern    Sample No.

3/ Samples in brackets had been scored positive first time round but the clones picked after restreaking did not come up positive. This is either due to mixed colonies in the original were variable expression from different preparation or initial false positives. Sequencing was carried out on a number of clones derived from huRT3:47 and these are emboldened in Section B.

In an attempt to determine which antibody chain was derived from the original human clone, separate PCR of the heavy and light V genes was carried out on individual clones (using either FDTSEQ1 or LMB3 in conjunction with primers located in the sequence encoding the flexible linker peptide between the chains (PCRHLINK and LINKPCRL). Pairs of clones from each PCR group were analyzed (printed in bold print in Table 6). This result indicates that all heavy chains, with the exception of hu61:16 and hu61:33 (pattern B) had the same heavy chain as the original isolate. These two clones now have a heavy chain pattern similar to RT3:47 and a light chain pattern which may be similar to the parent clone, RT3:61. Reshuffled clones which had been described as having the same PCR pattern (from PCR/digest of whole SCFv, run on 3% gel) now show subtle differences (from PCR/digest of individual light chains, run on 4% gel). Thus, differences were found between hu1:11 and hu1:22 (pattern B), hu1:17 and hu1:26 (pattern D), hu1:32 and hu1:40 (pattern E). For clones derived from RT3:47, differences were found between light chains of hu47:9 and hu47:10 (pattern B), hu47:37 and hu47:1 (pattern C). For clones derived from RT3:61, differences were found between light chains of hu61:13 and hu61:24 (pattern A). This analysis, therefore, reveals even greater diversity between the clones.

Sequencing was carried out on clones derived by shuffling RT3:47. (printed in bold print in Table 6). Analysis of the heavy chains shows that with the exception of hu47:7, the sequence is identical to the original heavy chain. (Clones analysed were hu47:1, 2, 3, 5, 6, 8, 9, 10, 12, 20, and 22.). In hu47:7 a valine in CDR2 is converted to an alanine by a T to C change. Sequencing of the light chain was carried out on the clones printed in bold print in Table 6.

EXAMPLE 9.0

Directed Selection Using Specific Elution/Competitive Binding

It is hoped that panning procedures using competition for binding (e.g., with reaction products) or specific elution (e.g., with smaller phosphonates) can be used to control the panning process. A greater degree of flexibility could be exerted if such procedures were carried out in ELISA wells. Thus, following a particular procedure, the eluate could be collected and the whole plate carried through a detection procedure. Based on the results, the eluate from specific wells could be selected for further analysis/pannings.

In an experiment to examine the elution from 96 well plates using 100 mM triethylamine, it was found that the overnight ELISA signal following elution, went from 0.289 to 0.019. (Using $2.5 \times 10^{11}$ polyclonal phage/well derived from one round of panning the shuffled human RT3:47 library (47PAN1 phage). Titration of the eluate showed that $7.5 \times 10^7$ infectious phage were collected, i.e., 0.03% of input. This compares favorably with elution from Nunc immunosorb tubes where $1.6 \times 10^9$ infectious phage were yielded from an input of $1 \times 10^{13}$ for the same sample, i.e., 0.016% (see Table 3). By this type of approach, a range of specific elution procedures could be compared and the most suitable samples infected into *E. coli* for further work.

The minimal transition state analogues, equivalent to the left and right hand of the RT3 molecule, will be referred to as RT3a (Compound 8, FIG. 2) and RT3b (Compound 12, FIG. 3). The left and right hand products of substrate cleavage will be referred to as product A (Mesitylacetic acid, FIG. 4) and product B (Compound 13, FIG. 4). In order to determine the optimal concentrations of the various components required for panning/elution of the original mouse library, a dilution series was prepared for RT3, RT3a, RT3b, and both reaction products (product A and product B). These were pre-incubated with 100 µl of 10×polyclonal phage derived from one round of panning the mouse RT3 library (using triethylamine elution).

The results of this analysis are presented in FIG. 23A and 23B. The most effective inhibition occurs with RT3 itself. It is clear that binding of this selected phage population is inhibited to a far greater extent by the left hand TSA and product (FIG. 23A) than by the right hand portions (FIG. 23B). Indeed, it is not at all clear if any inhibition occurs at the concentrations tested with right hand TSA or product. Furthermore, it appears that there is greater inhibition by the left hand TSA than the left hand product.

Specific elution was attempted using the original unpanned mouse library. This was carried out by binding 200 µl of 10×phage concentrate to ELISA wells coated with 150 µl of 2 µg/ml RT3-BSA and blocked with 200 µl of 2% Marvel. Phage were allowed to bind for 1 hour and were eluted by adding 200 µl of the following:

0.05 µM, 0.5 µM or 5 µM RT3

5 µM, 50 µM or 500 µM RT3a

5 µM, 50 µM or 500 µM RT3b 100 mM triethylamine

Phage derived from two 15 minute elutions were pooled and reintroduced into TG1 or HB2151 cells. FIG. 24A plots the yield of phage under each set of conditions. Triethylamine gives approximately $10^4$ phage from an input equivalent to 2 ml of culture supernatant. This is in line with the successful panning described in the previous report, which has given rise to all the mouse clones described earlier. In that experiment, approximately $10^5$ phage were derived from an input, equivalent to 20 ml of culture supernatant. Elution with RT3 and RT3a gives rise to a greater number of phage than triethylamine. RT3b gives a level of elution equivalent to or just greater than that achieved in a "buffer only" control.

This experiment was repeated, but a higher coating concentration of RT3-BSA was used (100 µg/ml), and volumes were adjusted to ensure that coating and blocking volumes exceeded the volume of input phage (to prevent any background problems associated with non-specific sticking of phage up the side of the well). In this experiment (FIG. 24B), the overall yield of eluted phage in all samples was reduced from before.

Polyclonal phage and soluble antibody was prepared from the various populations and tested in ELISA. Positive signals were achieved with soluble and phage ELISA, from sample derived by elution with 500 µM RT3a where. Individual colonies from this population were screened and 22/144 of the clones were found to be positive.

Panning was also carried out in the original immunosorb tubes (Nunc). Elution was carried out using either 100 mM triethylamine or 500 µM RT3a. Binding was carried out in the presence or absence of product A. (50, 500, 5000 µM). The results are summarized below:

| ELUTION REGIME | CONCENTRATION OF COMPETING PRODUCT | YIELD (× $10^6$) |
|---|---|---|
| 1/ 100 mM triethylamine | 0 µM product a | 52 |
| 2/ 500 µM RT3a | 0 µM product a | 42 |
| 3/ 500 µM RT3a | 50 µM product a | 0.59 |
| 4/ 500 µM RT3a | 500 µM product a | 0.85 |
| 5/ 500 µM RT3a | 5000 µM product a | 47 |

In this experiment, the yield of phage by triethylamine and RT3a elution (42–52×$10^6$) is higher than previous experiments. The yield of phage from RT3a elution is reduced by 70 fold when 50 µM product A is present during binding (suggesting binding is specific). There is a similar reduction with 500 µM product A, but when 5000 µM product A is used, the yield returns to 47×$10^6$. (This may be an effect of DMS, used to dissolve the product, which was present at 7.2% in this particular sample). Thus, it is possible to elute phage from either 96 well plates or immunosorb tubes using hapten elution with minimal TSA molecules. Furthermore, the binding profile may be altered by competing with reaction products, thereby tailoring the binding profile of the eluted population according to the desired requirements.

EXAMPLE 10

CDR Shuffling Of Human RT3 Binders

The scheme used for shuffling CDR fragments is a modification of the chain shuffling scheme described in Example 8.1.

The primers VHCDR3BACK and REV VHCDR3BACK are complementary to each other and to a conserved sequence in the framework region of human VH genes immediately upstream of CDR3. A population of DNA fragments which includes both CDR1 and CDR2 of the heavy chain from the library described by Marks et al., (1991) can be amplified using REV VHCDR3BACK (see below for sequence) and LBM3 (described in Example 4.2) and the remainder of the scFV from the chosen clone can be amplified using VHCDR3BACK (see below for sequence) and FDTSEQ1 (described in Example 4.2). This permits the linkage of a population of CDRs 1 and 2 with the remaining portion of a single clone by a two-fragment assembly reaction.

Similarly, a library of DNA fragments containing the CDR3 region of the heavy chain may be amplified using VHCDR3BACK and the linker located primer, PCRHLINK (see example 4.2). The remaining portion of the heavy chain from the chosen clone was amplified with REV VHCDR3BACK and LMB3 and the light chain was amplified with LINKPCRL (see example 4.2) and FDTSEQ1. Thus, a population of CDR3 fragments may be introduced into a single clone by two sequential two-fragment assembly reactions; the first invovling assembly of CDR 1 and 2 from the clone with the population of CDR3s. This is followed by a secondary PCR reaction using the flanking primers of this fragment LMB3 and PCRHLINK. the product of this was gel purified for subsequent assembly of this with the light chain from the clone.

For both CDR shuffling regimes, a final PCR reaction using the scFV-flanking primers LMB3 and FDTSEQ1 is performed. The CDR shuffled material is then digested with Not1 and Sfi1 for cloning into pCANTAB5-his 6 (see FIG. 7).

Method For CDR Shuffling

The primers FDTSEQ1, LMB3, PCRHLINK and LINK-PCRL are described in Example 4.2. In addition, the following primers are used:

| | |
|---|---|
| VHCDR3BACK 5' GAC ACG GC(TC) GT(AG) TAT TAC TGT 3' (see SEQ ID NO:34) | |
| REV VHCDR3BACK 5' ACA GTA ATA (CT)AG (GA)GC CGT GTC 3' (see SEQ ID NO:35) | |

(Nucleotides in paraentheses indicate introduced "wobbles" in the primer design to ensure universal amplification.)

Primary PCR products are prepared in the following reactions:

CD 1 and 2 Fragment

| | |
|---|---|
| LBM3 primer | 2.5 µl |
| (10 pmoles/µl) | |
| REV VHCDR3BACK primer | 2.5 µl |
| (10 pmoles/µl) | |
| 10× PCR | 5.0 µl |
| Reaction Buffer | |
| 5 mM each dNTP(S) | 2.5 µl |
| Taq polymerase | 0.3 µl |
| (5 U/µl) | |
| Water to | 50 µl |

CDR3 Fragment

| | |
|---|---|
| PCRHLINK Primer | 2.5 µl |
| (10 pmoles/µl) | |
| VHCDR3BACK primer | 2.5 µl |
| (10 pmoles/µl) | |
| 10× PCR | 5.0 µl |
| Reaction Buffer | |
| 5 mM each dNTP(s) | 2.5 µl |
| Taq polymerase | 0.3 µl |
| (5 U/µl) | |
| Water to | 50 µl |

VHCDR3-Linker-VL Fragment

| | |
|---|---|
| FDTSEQ1 primer | 2.5 µl |
| (10 pmoles/µl) | |
| VHCDR3BACK primer | 2.5 µl |
| (10 pmoles/µl) | |
| 10× PCR | 5.0 µl |
| Reaction Buffer | |
| 5 mM each dNTP(s) | 2.5 µl |
| Taq polymerase | 0.3 µl |
| (5 U/µl) | |
| Water to | 50 µl |

Linker-VL Fragment

| | |
|---|---|
| FDTSEQ1 primer | 2.5 µl |
| (10 pmoles/µl) | |
| LINKPCRL primer | 2.5 µl |
| (10 pmoles/µl) | |
| 10× PCR | 5.0 µl |
| Reaction Buffer | |
| 5 mM each dNTP(s) | 2.5 µl |
| Taq polymerase | 0.3 µl |
| (5 U/µl) | |
| Water to | 50 µl |

Miniprep DNA was prepared from the library described by Marks et al. (1991) as template for PCR. PCR produced from the clone was prepared by innoculating from a bacterial colony.

PCR conditions were 25 cycles of 94° C. 1 minute, 55° C. 1 minute, 72° C. 2 minutes with a final 10 minutes at 72° C.

Primary PCR products were gel purified using the Promega Magic PCR Prep System except for the CDR3 fragment which requires Mermaid purification (Bio 101) due to its maller size.

CDR1+2 Shuffling
Assembly Of Library CDR1+2 Fragments With The VH CDR3-Linker VL Fragment From An Isolated Clone

| | |
|---|---|
| Purified library CDR1+2 DNA | 20–50 ng |
| Purified VHCDR3-Linker-VL Fragment | 20–50 ng |
| from an isolated clone | |
| 10× PCR Buffer | 5.0 µl |
| 5 mM each dNTP(s) | 2.5 µl |
| Taq polymerase | 0.3 µl |
| (5 U/µl) | |
| Water to | 50 µl |

PCR conditions as for primary PCRs.
Secondary PCR Of Assembled CDR1+2 Shuffled DNA

| | |
|---|---|
| Assembly product | 1.0 µl |
| FDTSEQ1 primer | 2.5 µl |
| (10 pmoles/µl) | |
| LMB3 primer | 2.5 µl |
| (10 pmoles/µl) | |
| 10× PCR | 5.0 µl |
| Reaction Buffer | |
| 5 mM each dNTP(s) | 2.5 µl |
| Taq polymerase | 0.3 µl |
| (5 U/µl) | |
| Water to | 50 µl |

CDR3 Shuffling
Assembly Of Library CDR3 Fragments With The CDR1+@ Fragment From An Isolated Clone

| | |
|---|---|
| Purified library CDR 3 DNA | 20–50 ng |
| Purified CDR1+2 | 20–50 ng |
| from an isolated clone | |
| 10× PCR Buffer | 5.0 µl |
| 5 mM each dNTP(s) | 2.5 µl |
| Taq polymerase | 0.3 µl |
| (5 U/µl) | |
| Water to | 50 µl |

Second PCR Of Assembled Library CDR3-CDR1+2 From An Isolated Clone

| | |
|---|---|
| Assembly product | 1.0 µl |
| PCRHLINK primer | 2.5 µl |
| (10 pmoles/µl) | |
| LMB3 primer | 2.5 µl |
| (10 pmoles/µl) | |
| 10× PCS | 5.0 µl |
| Reaction Buffer | |
| 5 mM each dNTP(s) | 2.5 µl |
| Taq polymerase | 0.3 µl |
| (5 U/µl) | |
| Water to | 50 µl |

PCR conditions as for primary PCRs.
The library CDR3-CDR1+2 from an isolated clone secondary PCR product was gel purified using the Promega Magic PCR Prep system.
Assembly of CDR3 Shuffled DNA

| | |
|---|---|
| Purified library CDR3-CDR1+2 single | 20–50 ng |
| clone secondary PCR product | |
| Purified Linker-VL fragment | 20–50 ng |
| from an isolated clone | |
| 10× PCR Buffer | 5.0 µl |
| 5 mM each dNTP(s) | 2.5 µl |
| Taq polymerase | 0.3 µl |
| (5 U/µl) | |
| Water | |

PCR conditions as for primary PCRs.
Secondary PCR Of Assembled CDR3 Shuffled DNA

| | |
|---|---|
| Assembly product | 1.0 µl |
| FDTSEQ1 primer | 2.5 µl |
| (10 pmoles/µl) | |

| -continued | |
|---|---|
| LMB3 primer | 2.5 μl |
| (10 pmoles/μl) | |
| 10× PCR Reaction Buffer | 5.0 μl |
| 5 mM each dNTP(s) | 2.5 μl |
| Taq polymerase | 0.3 μl |
| (5 U/μl) | |
| Water to | 50 μl |
| PCR conditions as for primary PCRs. | |

The CDR3 shuffled secondary PCR product was gel purified using the Promega Magic PCR Prep system and digested and cloned as described in Example 4.0. Transformation, phage rescue, panning, and screening were as described above.

Colonies were screened after one or two rounds of panning against RT3-BSA and RT3 binders identified.

EXAMPLE 11

Derivation Of Human Catalytic Antibodies By "Imprinting"

The process of "imprinting" involves using an existing antibody with desired binding characteristics, to derive new antibodies, with similar characteristics. This is done by recombining original antibody chains, or parts thereof, with a library of complementary parts. When new antibody elements are found, which complement the original antibody binding characteristics, these are recombined with a library which replaces the original antibody binding characteristics, these are recombined with a library which replaces the original antibody part, to give an entirely new antibody which mimics the binding of the original antibody (PCT/GB/92/01755). This approach might be used to derive human catalytic antibodies from an existing mouse catalytic antibody.

This example describes a "two-step conversion". This, of course, may be done over multiple steps or in a single step, if a hybrid molecule consisting of part of the original antibody is sufficient.

This is a useful method for deriving human antibodies with similar binding activities to an existing mouse antibody for example.

The catalytic phage antibody clones 18 and 83 (see Example 5.2) in pCANTAb vectors, (cloned in pCANTAB vectors), were used as template for PCR amplification of separate heavy and light chains. Heavy chains were amplified with LMB3 and PCRHLINK and light chains were amplified with LINKPCRL and FDTSEQ1 as described above. Libraries of human heavy and light chains were also amplified by PCR using the samer primers and with DNA prepared from the human scFv library described by Marks et al., J. Mol. Biol. 222 (1991):581–597 as described above.

The individual mouse heavy chains from each clone were then recombined with the library of human light chains by PCR linkage as described above. Similarly, the individual light chains were recombined with the library of heavy chains in the same way.

The resulting linked products were cleaved with ApaL1 (for mouse heavy chains) or Sfi1 (for human heavy chains) along with Not1, ligated into the appropriate pCANTAB vector and transformation into E. coli TG1 cells. All steps were as described above.

Individual populations of TG1 cells carrying each separate library, were grown for 2–3 hours at 30° C. and rescued by infection with VCSM13 helper phage at 37° C. After overnight growth phage particles were collected and concentrated. Each population was panned several times against RT3-BSA and indivdual binding clones identified by ELISA.

Binding clones were selected and the human chain of each clone was amplified by PCR as before. This chain was recombined with the PCR product of the human library of complementary chains. PCR linkage, cleavage with SFi1 and Not1, ligation, transformation, phage rescue, panning and screening were as before.

In this way, a new population of RT3 binders were derived whose binding profile was directed by the original mouse clone but which were entirely human. The above example covers imprinting by shuffling separate chains but could equally apply to shuffling parts of chains in a single or multiple rounds (as above). The library material was derived from the library of Marks et al. J. Mol. Biol. 222 (1991):581–597 but could equally come from PCR products of human blood, spleen, etc., or could be partially or totally derived from synthetic DNA.

The example given above involves shuffling chains within a single chain Fv on a single replicon. A similar result can be achieved by using non-linked VH/VL or VH-CHG/VL-CL fragments displayed on phage (McCafferty et al. WO 92/01047). These again may be on the same replicon or may be on different replicons. For example, the heavy chain of the original mouse antibody may be cloned into pUC19 or other plasmid, in frame with appropriate promoters, signal peptide and stop codon(s) enabling it to be expressed as a soluble VH or VH-CHI fragment in the bacterial periplasm (Better et al., 1989; Skerra et al., 1989). A growing culture of cells carrying this plasmid could then be infected with helper phage derived from a library of human light chains (either VL or VL-CL, as appropriate), cloned as fusions with gene III in fd-CAT1 or fd-DOG1 (McCafferty et al., supra. 1991) for example. This will give rise to a population of phage expressing indivudal human light chain fused to gene III, with a heavy chain partner derived from the mouse clone. Those human chains, which complement the binding activity of the mouse chain, will be enriched by panning (McCafferty, et al., supra. 1991) and the gene encoding this chain will be present in the phage particle.

Light chains derived in this way can be recloned into a vector for soluble expression of the single chain in the periplasm, as was done for the original mouse chain. As before, a growing culture of cells expressing these individual human light chains could be infected with helper phage derived from a library of human heavy chains, cloned as fusions with gene III in fd-CAT1 or fd-DOG1 (McCafferty et al., supra. 1991) for example. As before panning against antigen with enrich those clones with the appropriate binding activity. This will result in a pair of human clones which mirror the binding of the original mouse clone.

A similar process can be carried out by shuffling with the human heavy chain first and then the light chain. Alternatively, the enriched population or clones derived from one round of separate shuffling of heavy and light chains can be recombined with each other in the same way as described above for either SCFv(s) or separate chains.

What is claimed is:

1. A method for producing catalytic antibodies displayed on phage comprising the steps of:
   (a) generating a gene library of antibody-derived domains;
   (b) inserting coding for said domains into a phage expression vector;
   (c) isolating said catalytic antibodies; and
   (d) wherein said phage expression vector incorporates therein a histidine peptide in tandem with a myc peptide.

2. A method as recited in claim 1 wherein said catalytic antibodies are single chain antibodies.

3. A method as recited in claim 1 wherein the antibodies isolated in step (c) are produced in quantity by culturing *E. coli* cells.

4. Catalytic antibodies prepared by the method of claim 1.

5. A method as recited in claim 1 wherein said gene library of antibody-derived domains is generated from one or more of the following groups:
(a) gene fragments obtained from lymphocytes from an immunized animal;
b) gene fragments obtained from lymphocytes from a non-immunized animal;
(c) gene fragments obtained by shuffling of VH and VL chains;
(d) gene fragments obtained by shuffling of CDR regions;
(e) gene fragments obtained by mutagenesis of CDR regions;
(f) imprinting; or (g) synthetic antibody genes.

6. A method for isolating catalytic antibodies displayed on phage comprising the steps:
(a) preparing an antigen;
(b) immunizing with said antigen;
(c) generating a library of VH and VL domains from said immunized animal;
(d) cloning said VH and VL domains into a phage expression vector to generate phage display antibodies;
(e) selecting phage display antibodies which bind specifically to said antigen;
(f) screening said selected phage display antibodies for catalytic activity to substrate;
(g) isolating said catalytic antibodies; and
(h) wherein said phage expression vector incorporates therein a histidine peptide in tandem with a myc peptide.

7. A method as recited in claim 6 wherein said cataltyic antibodies are single chain antibodies.

8. A method as recited in claim 6 wherein said antigen is a transition state analog.

9. A method as recited in claim 6 wherein said antigen is a phosphonate.

10. A method as recited on claim 6 wherein said antigen is

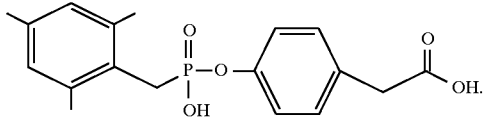

11. Catalytic antibodies prepared by the method of claim 6.

12. A method for isolating catalytic antibodies displayed on phage comprising the following steps:
(a) preparing an antigen;
(b) generating a library of VH and VL domains;
(c) cloning said VH and VL domains into a phage expression vector to generate phage display antibodies;
(d) selecting phage display antibodies which bind specifically to said antigen;
(e) screening said selected phage display antibodies for catalytic activity to substrate;
(f) isolating said catalytic antibodies; and
(g) wherein said phage expression vector incorporates therein a histidine peptide in tandem with a myc peptide.

13. A method as recited in claim 12 wherein said library is mouse-derived.

14. A method as recited in claim 12 wherein said antigen is a transition state analog.

15. A method as recited in claim 12 wherein said antigen is a phosphonate.

16. A method as recited in claim 12 wherein said antigen is

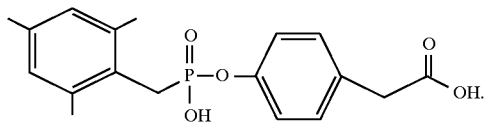

17. Catalytic antibodies prepared by the method of claim 12.

18. A method for producing catalytic antibodies displayed on phage through chain shuffling comprising the following steps:
(a) combining a library of VL genes with VH genes to form a chain shuffled library;
(b) cloning the shuffled chain;
(c) expressing said chain shuffled antibody on phage;
(d) selecting against an antigen;
(e) screening for catalytic activity; and
(f) wherein said phage incorporates therein a histidine peptide in tandem with a myc peptide.

19. A method for producing catalytic antibodies displayed on phage through CDR shuffling comprising the following steps:
(a) isolating VL and VH genes;
(b) isolating a library of CDR regions;
(c) recombining said VL and VH genes with said library of CDR regions to produce a CDR shuffled library;
(d) cloning the CDR shuffled library;
(e) expressing said CDR shuffled library on phage;
(f) selecting against an antigen;
(g) screening for catalytic activity; and
(h) wherein said phage incorporates therein a histidine peptide in tandem with a myc peptide.

20. A method for producing catalytic antibodies displayed on phage through imprinting comprising the following steps:
(a) selecting a set of antibodies;
(b) isolating a set of VH and a set of VL genes from said antibodies;
(c) combining said set of VH with a library of VL and combining said set of VL with a library of VH to form two combinatorial libraries;
(d) cloning said combination libraries;
(e) expressing said libraries on phage;
(f) selecting against an antigen;
(g) isolating selected libraries of VH and VL genes;
(h) combining said libraries of VH and VL genes;
(i) cloning said combined libraries;
(j) expressing said combined libraries on phage;
(k) reselecting against an antigen;
(l) screening for catalytic activity; and
(m) wherein said phage incorporates therein a histidine peptide in tandem with a myc peptide.

21. A method for enhancing the rate of cleavage or formation of a specific bond within a molecule in vivo which comprises introducing into an animal an effective amount of a phage-derived catalytic antibody; and wherein said phage incorporates therein a histidine peptide in tandem with a myc peptide.

22. A method for in vivo activation of a prodrug comprising:
   (a) introducing a prodrug into a patient, said prodrug having a chemical bond therein which upon cleavage releases the active form of said drug;
   (b) introducing into said patient an effective amount of a phage-derived catalytic antibody capable of cleaving said bond in said prodrug; and
   (c) wherein said phage incorporates therein a histidine peptide in tandem with a myc peptide.

23. A method for activating or deactivating a biological function in an animal by enhancing the rate of cleavage or formation of a specific bond within a molecule in vivo which comprises introducing into an animal an effective amount of a catalytic antibody, said antibody having been produced by the method of claim 1.

24. A method for activating or deactivating a biological function in an animal by enhancing the rate of cleavage or formation of a specific bond within a molecule in vivo which comprises introducing into an animal an effective amount of a catalytic antibody, said antibody having been produced by the method of claim 18.

25. A method for activating or deactivating a biological function in an animal by enhancing the rate of cleavage or formation of a specific bond within a molecule in vivo which comprises introducing into an animal an effective amount of a catalytic antibody, said antibody having been produced by the method of claim 19.

26. A method for activating or deactivating a biological function in an animal by enhancing the rate of cleavage or formation of a specific bond within a molecule in vivo which comprises introducing into an animal an effective amount of a catalytic antibody, said antibody having been produced by the method of claim 20.

* * * * *